(12) United States Patent
Breault et al.

(10) Patent No.: US 7,176,212 B2
(45) Date of Patent: *Feb. 13, 2007

(54) 2,4-DIAMINO PYRIMIDINE COMPOUNDS HAVING ANTI-CELL PROLIFERATIVE ACTIVITY

(75) Inventors: Gloria Anne Breault, Macclesfield (GB); Janet Elizabeth Pease, Macclesfiled (GB)

(73) Assignee: AstraZeneca AB, Sodertalje (SE)

( * ) Notice: Subject to any disclaimer, the term of this patent is extended or adjusted under 35 U.S.C. 154(b) by 126 days.

This patent is subject to a terminal disclaimer.

(21) Appl. No.: 10/771,118

(22) Filed: Feb. 4, 2004

(65) Prior Publication Data

US 2005/0090493 A1 Apr. 28, 2005

Related U.S. Application Data

(63) Continuation of application No. 09/763,705, filed as application No. PCT/GB99/02790 on Aug. 24, 1999, now abandoned.

(30) Foreign Application Priority Data

Aug. 29, 1998 (GB) .................................. 9818989.7
Dec. 24, 1998 (GB) .................................. 9828433.4

(51) Int. Cl.
*C07D 239/48* (2006.01)
*A61K 31/505* (2006.01)
*C07D 239/42* (2006.01)

(52) U.S. Cl. ...................................... 514/275; 544/323
(58) Field of Classification Search ................. 544/323; 514/275
See application file for complete search history.

(56) References Cited

U.S. PATENT DOCUMENTS

| | | | |
|---|---|---|---|
| 4,983,608 A | 1/1991 | Effland et al. ............... | 514/216 |
| 5,516,775 A | 5/1996 | Zimmermann et al. .. | 514/224.2 |
| 5,610,303 A | 3/1997 | Kimura et al. ............... | 544/326 |
| 5,739,143 A | 4/1998 | Adams et al. ............... | 514/275 |
| 5,859,041 A | 1/1999 | Liverton et al. ............ | 514/396 |
| 6,593,326 B1 | 7/2003 | Bradbury et al. ......... | 514/235.8 |
| 6,632,820 B1 | 10/2003 | Breault et al. ............... | 514/256 |
| 6,649,608 B2 | 11/2003 | Pease et al. ............. | 514/227.8 |
| 6,670,368 B1 | 12/2003 | Breault et al. ............... | 514/269 |
| 6,710,052 B2 | 3/2004 | Pease et al. ................. | 514/272 |
| 6,716,831 B1 | 4/2004 | Breault et al. ............... | 514/183 |

FOREIGN PATENT DOCUMENTS

| | | |
|---|---|---|
| CA | 2231765 | 9/1998 |
| EP | 0 363 002 | 4/1990 |
| EP | 0 379 806 | 8/1990 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |

(Continued)

OTHER PUBLICATIONS

Simone, Oncology: Introduction, Cecil Textbook of Medicine, 20th Edition, vol. 1, pp. 1004-1010, 1996.*

(Continued)

*Primary Examiner*—Deepak Rao
(74) *Attorney, Agent, or Firm*—Morgan Lewis & Bockius LLP

(57) ABSTRACT

A pyrimidine derivative of formula (I) wherein, for example, $R^1$ is hydrogen, (1–6C)alkyl, (3–5C)alkenyl or (3–5C)alkynyl; $Q_1$ and $Q_2$ are independently selected from phenyl, naphthyl, indanyl and 1,2,3,4-tetrahydronaphthyl; and one or both of $Q_1$ and $Q_2$ bears on any available carbon atom one substituent of formula (Ia) [provided that when present in $Q_1$ the substituent of formula (Ia) is not adjacent to the —NH— link]; wherein, for example, X is $CH_2$, O, S or NH; Y is H or as defined for Z; Z is OH, SH, $NH_2$, (1–4C)alkoxy, (1–4C)alkylthio, —NH(1–C)alkyl, —N[(1–4C)alkyl]$_2$ or —NH—(3–8C)cycloalkyl; n is 1, 2 or 3; m is 1, 2 or 3; and $Q_1$ and $Q_2$ may optionally bear other substituents selected, for example, from halogeno, (1–6C)alkyl, cyano and (2–4C) alkenyl; or a pharmaceutically-acceptable salt or in-vivo-hydrolyzable ester thereof; are useful as anti-cancer agents; and processes for heir manufacture and pharmaceutical compositions containing them are described

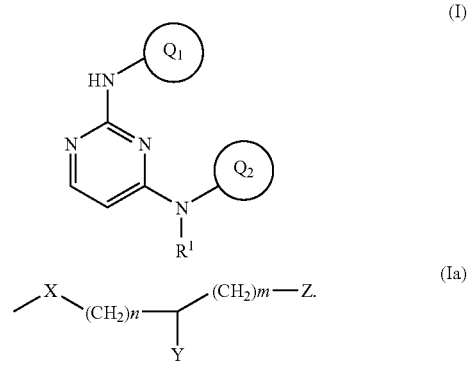

11 Claims, No Drawings

FOREIGN PATENT DOCUMENTS

| | | |
|---|---|---|
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |
| WO | 99/32121 | 1/1999 |
| WO | 99/18942 | 4/1999 |
| WO | 99/31073 | 6/1999 |
| WO | 99/50250 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/25780 | 5/2000 |
| WO | 00/26209 | 5/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/14375 A1 | 3/2001 |
| WO | 01/29009 A1 | 4/2001 |
| WO | 01/30778 A1 | 5/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |

OTHER PUBLICATIONS

Luvalle et al., Cell Cycle Control in Growth Plate Chondrocytes, Frontiers in Biosciences 5, d493-503, May 2001.*

Blain et al., Differential Interaction of the Cyclin-dependent Kinase (Cdk) Inhibitor p27Kip1 with Cyclin A-Cdk2 and Cyclin D2- Cdk4, The Journal of Biological Chemistry, vol. 41, pp. 25863-25872, Oct. 1997.*

El-Kerdawy et al.; "2,4-Bis (Substituted)-5-Nitropyrimidines of Expected Diuretic Action"; Egypt J. Chem. vol. 29, No. 2, 1986, pp. 247-251.

Fiziol Akt Veshchestva, 1975, vol. 7, pp. 68-72.

Ghosh et al.; "2,4-Bis(arylamino)-5-methylpyrimidines as Antimicrobial Agents"; J. Med. Chem., 1967, vol. 10, No. 5, pp. 974-975.

Ghosh, "2,4-Bis(Arylamino)-6-Methyl Pyrimidines as Antimicrobial Agents", J. Indian Chem. Soc., vol. 58, No. 5, 1981, pp. 512-513.

Ghosh, "2,4-Bis(arylamino)-6-methylpyrimidines as an antimicrobial agents", Chemical Abstract No. 97712f, vol. 95, 1981, pp. 648.

Schmidt et al.; "A Convenient Synthesis of 2-substituted 4-Amino-5-pyrimidinecarbonitriles"; J. Heterocycle Chem., 1997, vol. 24, No. 5, pp. 1305-1307.

* cited by examiner

2,4-DIAMINO PYRIMIDINE COMPOUNDS HAVING ANTI-CELL PROLIFERATIVE ACTIVITY

This is a continuation of application Ser. No. 09/763,705, filed Feb. 26, 2001, now abandoned; which is a PCT National Stage of PCT/GB99/02790 filed Aug. 24, 1999.

The invention relates to pyrimidine derivatives, or pharmaceutically-acceptable salts or in-vivo-hydrolysable esters thereof, which possess anti-cancer (such as anti-cell-proliferative, anti-cell migration and/or apoptotic) activity and are therefore useful in methods of treatment of the human or animal body. The invention also relates to processes for the manufacture of said pyrimidine derivatives, to pharmaceutical compositions containing them and to their use in the manufacture of medicaments for use in the production of an anti-cancer (anti-cell-proliferation/migration and/or apoptotic) effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

Furthermore, it is believed that inhibition of focal adhesion kinase (FAK), which is involved in transduction signalling pathways, induces apoptosis (cell-death) and/or inhibits cell migration and an inhibitor of FAK may therefore have value as an anti-cancer agent.

The present invention is based on the discovery that certain 2,4-pyrimidine compounds surprisingly inhibit the effects of cell cycle kinases showing selectivity for CDK2, CDK4 and CDK6, and also inhibit FAK and thus possess anti-cancer (anti-cell-migration/proliferation and/or apoptotic) properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I)

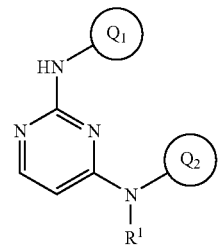

wherein
R$^1$ is selected from hydrogen, (1–6C)alkyl [optionally substituted by one or two substituents independently selected from halo, amino, (1–4C)alkylamino, di-[(1–4C)alkyl]amino, hydroxy, cyano, (1–4C)alkoxy, (1–4C)alkoxycarbonyl, carbamoyl, —NHCO(1–4C)alkyl, trifluoromethyl, phenylthio, phenoxy, pyridyl, morpholino], benzyl, 2-phenylethyl, (3–5C)alkenyl [optionally substituted by up to three halo substituents, or by one trifluoromethyl substituent, or one phenyl substituent], N-phthalimido-(1–4C)alkyl, (3–5C)alkynyl [optionally substituted by one phenyl substituent] and (3–6C)cycloalkyl-(1–6C)alkyl;

wherein any phenyl or benzyl group in R$^1$ is optionally substituted by up to three substituents independently selected from halogeno, hydroxy, nitro, amino, (1–3C)alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C)alkyl]amino, hydroxy and trifluoromethyl], (3–5C)alkenyl [optionally substituted by up to three halo substituents, or by one trifluoromethyl substituent], (3–5C)alkynyl, (1–3C)alkoxy, —SH, —S—(1–3C)alkyl, carboxy, (1–3C)alkoxycarbonyl;

Q$_1$ and Q$_2$ are independently selected from phenyl, naphthyl, indanyl and 1,2,3,4-tetrahydronaphthyl;

and one or both of Q$_1$ and Q$_2$ bears on any available carbon atom one substituent of the formula (Ia) and Q$_2$ may optionally bear on any available carbon atom further substituents of the formula (Ia)

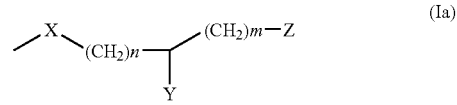

[provided that when present in Q$_1$ the substituent of formula (Ia) is not adjacent to the —NH— link];

wherein
X is CH$_2$, O, S, NH or NRx [wherein Rx is (1–4C)alkyl, optionally substituted by one substituent selected from halo, amino, cyano, (1–4Calkoxy or hydroxy];

Y is H or as defined for Z;

Z is OH, SH, NH$_2$, (1–4C)alkoxy, (1–4C)alkylthio, —NH(1–4C)alkyl, —N[(1–4C)alkyl]$_2$, —NH—(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;

n is 1, 2 or 3; m is 1, 2 or 3;

and $Q_1$ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido (H$_2$N—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino;

and also independently, or where appropriate in addition to, the above substituents, $Q_1$ may optionally bear on any available carbon atom up to two further substituents independently selected from (3–8C)cycloalkyl, phenyl-(1–4C)alkyl, phenyl-(1–4C)alkoxy, phenylthio, phenyl, naphthyl, benzoyl, benzimidazol-2-yl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio and phenyl-(1–4C)alkoxy substituents may optionally bear up to five substituents independently selected from halogeno, (1–4C)alkyl and (1–4C)alkoxy;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido (H$_2$N—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or where appropriate in addition to, the above optional substituents, $Q_2$ may optionally bear on any available carbon atom up to two further substituents independently selected from (3–8C)cycloalkyl, phenyl-(1–4C)alkyl, phenyl-(1–4C)alkoxy, phenylthio, phenyl, naphthyl, benzoyl, phenoxy, benzimidazol-2-yl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C)alkoxy substituents may optionally bear up to five substituents independently selected from halogeno, (1–4C)alkyl and (1–4C)alkoxy; or a pharmaceutically-acceptable salt or in-vivo-hydrolysable ester thereof.

A suitable value for a ring substituent when it is a 5- or 6-membered aromatic heterocycle (linked via a ring carbon atom and containing one to three heteroatoms independently selected from oxygen, sulphur and nitrogen) is, for example, pyrrole, furan, thiophene, imidazole, oxazole, isoxazole, thiazole, pyridyl, pyridazinyl, pyrimidinyl, pyrazinyl or p-isoxazine.

In this specification the term "alkyl" includes both straight and branched chain alkyl groups but references to individual alkyl groups such as "propyl" are specific for the straight chain version only. An analogous convention applies to other generic terms.

Suitable values for the generic radicals (such as in $R^1$ and in substituents on $Q_1$ and $Q_2$) referred to above include those set out below:

when it is halogeno is, for example, fluoro, chloro, bromo and iodo; (2–4C)alkenyl is, for example, vinyl and allyl; when it is (3–5C)alkenyl is, for example, allyl or buten-3-yl; when it is (3–5C)alkynyl is, for example, propyn-2-yl; when it is (2–4C)alkynyl is, for example, ethynyl and propyn-2-yl; when it is (3–6C)cycloalkyl-(1–6C)alkyl is, for example, cyclopropylmethyl; when it is (3–8C)cycloalkyl is, for example, cyclobutyl, cyclopentyl or cyclohexyl; when it is (1–4C)alkanoyl or (1–5C)alkanoyl is, for example, formyl and acetyl; when it is (1–4C)alkoxycarbonyl is, for example, methoxycarbonyl, ethoxycarbonyl, propoxycarbonyl and tert-butoxycarbonyl; when it is (1–3C)alkyl is, for example, methyl, ethyl, propyl, isopropyl; when it is (1–4C)alkyl is, for example, methyl, ethyl, propyl, isopropyl, butyl, isobutyl, sec-butyl or tert-butyl; when it is (1–6C)alkyl is, for example, methyl, ethyl, propyl, isopropyl, butyl, isobutyl, sec-butyl, tert-butyl or 3-methylbutyl or hexyl; when it is hydroxy-(1–3C)alkyl is, for example, hydroxymethyl, 1-hydroxyethyl, 2-hydroxyethyl and 3-hydroxypropyl; when it is hydroxy-(2–4C)alkyl is, for example, 2-hydroxyethyl and 3-hydroxypropyl; when it is fluoro-(1–4C)alkyl is, for example, fluoromethyl, difluoromethyl, trifluoromethyl and 2-fluoroethyl; when it is amino-(1–3C)alkyl is, for example, aminomethyl, 1-aminoethyl and 2-aminoethyl; when it is (1–4C)alkylamino-(1–3C)-alkyl is, for example, methylaminomethyl, ethylaminomethyl, 1-methylaminoethyl, 2-methylaminoethyl, 2-ethylamimoethyl and 3-methylaminopropyl; when it is di-[(1–4C)alkyl]amino-(1–3C)alkyl is, for example, dimethylaminomethyl, diethylaminomethyl, 1-dimethylaminoethyl, 2-dimethylaminoethyl and 3-dimethylaminopropyl; when it is cyano-(1–4C)alkyl is, for example cyanomethyl, 2-cyanoethyl and 3cyanopropyl; when it is (2–4C)alkanoyloxy-(1–4C)-alkyl is, for example, acetoxymethyl, propionyloxymethyl, butyryloxymethyl, 2-acetoxyethyl and 3-acetoxypropyl; when it is (1–4C)alkoxy-(1–3C)alkyl is, for example, methoxymethyl, ethoxymethyl, 1-methoxyethyl, 2-methoxyethyl, 2-ethoxyethyl and 3-methoxypropyl; when it is carboxy-(1–4C)alkyl is, for example carboxymethyl, 1-carboxyethyl, 2-carboxyethyl and 3-carboxypropyl; when it is (1–4C)alkoxycarbonyl-(1–4C)alkyl is, for example, methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; when it is carbamoyl-(1–4C)alkyl is, for example carbamoylmethyl, 1-carbamoylethyl, 2-carbamoylethyl and 3-carbamoylpropyl; when it is N-(1–4C)alkylcarbamoyl-(1–4C)alkyl is, for example, N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; when it is N,N-di-[(1–4C)alkyl]-carbamoyl-(1–4C)alkyl is, for example, N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; when it is pyrrolidin-1-yl-(1–3C)alkyl is, for example, pyrrolidin-1-ylmethyl and 2-pyrrolidin-1-ylethyl; when it is piperidin-1-yl-(1–3C)alkyl is, for example, piperidin-1-ylmethyl and 2-piperidin-1-ylethyl; when it is piperazin-1-yl-(1–3C)alkyl is, for example, piperazin-1-ylmethyl and 2-piperazin-1-ylethyl; when it is morpholino-(1–3C)alkyl is, for example, morpholinomethyl and 2-morpholinoethyl; when it is thiomorpholino-(1–3C)alkyl is, for example, thiomorpholinomethyl and 2-thiomorpholinoethyl; when it is (1–4C)alkoxy is, for example, methoxy, ethoxy, propoxy, isopropoxy or butoxy; when it is cyano-(1–4C)alkoxy is, for example, cyanomethoxy, 1-cyanoethoxy, 2-cyanoethoxy and 3-cyanopropoxy; when it is carbamoyl-(1–4C)alkoxy is, for example, carbamoylmethoxy, 1-carbamoylethoxy, 2-carbamoylethoxy and 3-carbamoylpropoxy; when it is N-(1–4C)alkylcarbamoyl-(1–4C)alkoxy is, for example, N-methylcarbamoylmethoxy, N-ethylcarbamoylmethoxy, 2-(N-methylcarbamoyl)ethoxy, 2-(N-ethylcarbamoyl)ethoxy and 3-(N-methylcarbamoyl)propoxy; when it is N,N-di-[(1–4C)alkyl]-carbamoyl-(1–4C)alkoxy is, for example, N,N-dimethylcarbamoylmethoxy, N-ethyl-N-methylcarbamoylmethoxy, N,N-diethylcarbamoylmethoxy, 2-(N,N-dimethylcarbamoyl)ethoxy, 2-(N,N-diethylcarbamoyl)ethoxy and 3-(N,N-dimethylcarbamoyl)propoxy; when it is 2-(1–4C)alkylaminoethoxy is, for example, 2-(methylamino)ethoxy, 2-(ethylamino)ethoxy and 2-(propylamino)ethoxy; when it is 2-di-[(1–4C)alkyl]aminoethoxy is, for example, 2-(dimethylamino)ethoxy, 2-(N-ethyl-N-methylamino)ethoxy, 2-(diethylamino)ethoxy and 2-(dipropylamino)ethoxy; when it is (1–4C)alkoxycarbonyl-(1–4C)alkoxy is, for example, methoxycarbonylmethoxy, ethoxycarbonylmethoxy, 1-methoxycarbonylethoxy, 2-methoxy-carbonylethoxy, 2-ethoxycarbonylethoxy and 3-methoxycarbonylpropoxy; when it is halogeno-(1–4C)alkoxy is, for example, difluoromethoxy, trifluoromethoxy, 2-fluoroethoxy, 2-chloroethoxy, 2-bromoethoxy, 3-fluoropropoxy, 3-chloropropoxy and 2-chloro-2,1,1-trifluoroethoxy; when it is (2–4C)alkanoyloxy-(2–4C)alkoxy is, for example, 2-acetoxyethoxy, 2-propionyloxyethoxy, 2-butyryloxyethoxy and 3-acetoxypropoxy; when it is 2-(1–4C)alkoxyethoxy is, for example, 2-methoxyethoxy, 2-ethoxyethoxy; when it is carboxy-(1–4C)alkoxy is, for example, carboxymethoxy, 1-carboxyethoxy, 2-carboxyethoxy and 3-carboxypropoxy; when it is (3–5C)alkenyloxy is, for example, allyloxy; when it is (3–5C)alkynyloxy is, for example, propynyloxy; when it is (1–4C)alkylthio is, for example, methylthio, ethylthio or propylthio; when it is (1–4C)alkylsulphinyl is, for example, methylsulphinyl, ethylsulphinyl or propylsulphinyl; when it is (1–4C)alkylsulphonyl is, for example, methylsulphonyl, ethylsulphonyl or propylsulphonyl; when it is N-(1–4C)alkylcarbamoyl is, for example N-methylcarbamoyl, N-ethylcarbamoyl and N-propylcarbamoyl; when it is N,N-di-[(1–4C)alkyl]-carbamoyl is, for example N,N-dimethylcarbamoyl, N-ethyl-N-methylcarbamoyl and N,N-diethylcarbamoyl; when it is (1–4C)alkylamino or (1–3C)alkylamino is, for example, methylamino, ethylamino or propylamino; when it is di-[(1–4C)alkyl]amino or di-[(1–3C)alkyl]amino is, for example, dimethylamino, N-ethyl-N-methylamino, diethylamino, N-methyl-N-propylamino or dipropylamino; when it is (2–4C)alkanoylamino is, for example, acetamido, propionamido or butyramido; when it is phenyl-(1–4C)alkyl is, for example benzyl or 2-phenylethyl; when it is phenyl-(1–4C)alkoxy is, for example benzyloxy; when it is —NHCO(1–4C)alkyl is, for example acetamido; when it is N-phthalimido-(1–4C)alkyl is, for example 2-(N-phthalimido)ethyl or 3-(N-phthalimido)propyl.

A suitable pharmaceutically-acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine, tris-(2-hydroxyethyl)amine, N-methylpiperidine, N-ethylpiperidine, procaine, dibenzylamine, N,N-dibenzylethylamine, N-methyl deglucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

In another embodiment there is provided a compound of formula (a) wherein $R^1$ is selected from hydrogen, (1–6C)alkyl [optionally substituted by one or two substituents independently selected from halo, amino, (1–4C)alkylamino, di-[(1–4C)alkyl]amino, hydroxy, cyano, (1–4C)alkoxy, (1–4C)alkoxycarbonyl, carbamoyl, —NHCO(1–4C)alkyl, trifluoromethyl, phenylthio, phenoxy], benzyl, (3–5C)alkenyl [optionally substituted by up to three halo substituents, or by one trifluoromethyl substituent, or one phenyl substituent], N-phthalimido-(1–4C)alkyl, (3–5C)alkynyl and (3–6C)cycloalkyl-(1–6C)alkyl;

wherein any phenyl or benzyl group in $R^1$ is optionally substituted by up to three substituents independently selected from halogeno, hydroxy, nitro, amino, (1–3C)alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C)alkyl]amino, hydroxy and trifluoromethyl], (3–5C)alkenyl [optionally substituted by up to three halo substituents, or by one trifluoromethyl substituent], (3–5C)alkynyl, (1–3C)alkoxy, —SH, —S—(1–3C)alkyl, carboxy, (1–3C)alkoxycarbonyl;

$Q_1$ and $Q_2$ are both phenyl;

and one or both of $Q_1$ and $Q_2$ bears on any available carbon atom one substituent of the formula (Ia) and $Q_2$ may bear on any available carbon atom further substituents of the formula (Ia) [provided that when present in $Q_1$ the substituent of formula (Ia) is not adjacent to the —NH— link];

wherein; X is $CH_2$, O, NH or S; Y is H or as defined for Z; Z is OH, SH, $NH_2$, (1–4C)alkoxy, (1–4C)alkylthio, —NH(1–4C)alkyl, —N[(1–4C)alkyl]$_2$, pyrrolidin-1-yl, piperidin-1-yl, piperazin-1-yl, morpholino or thiomorpholino; n is 1, 2 or 3; m is 1, 2 or 3;

and $Q_1$ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–3C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkylthio, (1–4C)alkylsulphinyl, (1–4C)alkylsulphonyl, ureido ($H_2N$—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino;

and also independently, or in addition to, the above substituents, $Q_1$ may optionally bear on any available carbon atom up to two further substituents independently selected from phenyl-(1–4C)alkyl, phenyl-(1–4C)alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C)alkoxy substituents may optionally bear one or two substituents independently selected from halogeno, (1–4C)alkyl and (1–4C)alkoxy;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–3C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkoxy, cyano-(1–4C)alkoxy, carbamoyl-(1–4C)alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, ureido ($H_2N$—CO—NH—), (1–4C)alkylNH—CO—NH—, di-[(1–4C)alkyl]N—CO—NI—, (1 4C)alkylNH—CO—N[(1–4C)alkyl]-, di-[(1–4C)alkyl]N—CO—N[(1–4C)alkyl]-, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and also independently, or in addition to, the above substituents, $Q_2$ may optionally bear on any available carbon atom up to two further substituents independently selected from phenyl-(1–4C)alkyl, phenyl-(1–4C)alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C)alkoxy substituents may optionally bear one or two substituents independently selected from halogeno; (1–4C)alkyl and (1–4C)alkoxy; or a pharmaceutically-acceptable salt or in-vivo-hydrolysable ester thereof.

In a further embodiment there is provided a compound of formula (I) wherein $R^1$ is selected from hydrogen, (1–6C)alkyl [optionally substituted by one or two substituents independently selected from halo, amino, (1–4C)alkylamino, di-(1–4C)alkylamino, hydroxy, cyano, (1–4C)alkoxy, (1–4C)alkoxycarbonyl and carbamoyl], benzyl, (2–4C)alkenyl, (2–5C)alkynyl and (3–6C)cycloalkyl-(1–6C)alkyl;

$Q_1$ and $Q_2$ are both phenyl;

and one or both of $Q_1$ and $Q_2$ bears on any available carbon atom that is not adjacent to the —NH— or —NR— link one substituent of the formula (Ia) and $Q_2$ may bear on any available carbon atom that is not adjacent to the —NR$^1$— link further substituents of the formula (Ia) wherein; X is $CH_2$, O, NH or S; Y is H or as defined for Z; Z is OH, SH, $NH_2$, (1–4C)alkoxy, (1–4C)alkylthio, —NH(1–4C)alkyl, —N[(1–4C)alkyl]$_2$, pyrrolidin-1-yl, piperidin-1-yl, piperazin-1-yl, morpholino or thiomorpholino; n is 1, 2 or 3; m is 1, 2 or 3; and $Q_1$ may optionally bear on any available carbon atom up to four substituents independently selected from halogeno, thioxo, nitro, carboxy, cyano, (2–4C)alkenyl, (2–4C)alkynyl, (1–5C)alkanoyl, (1–4C)alkoxycarbonyl, (1–4C)alkyl, hydroxy-(1–3C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C) alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N, N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, (1–4C)alkylthio, (1–4C) alkylsulphinyl, (1–4C)alkylsulphonyl, ureido, carbamoyl, N-[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, phenyl-(1–4C)alkyl, phenyl-(1–4C)alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C) alkoxy substituents may optionally bear one or two substituents independently selected from halogeno, (1–4C) alkyl and (1–4C)alkoxy;

and $Q_2$ may optionally bear on any available carbon atom up to four substituents independently selected from halogeno, hydroxy, oxo, thioxo, nitro, carboxy, cyano, (2–4C) alkenyl, (2–4C)alkynyl, (1–5C)alkanoyl, (1–4C)alkoxycarbonyl, (1–4C)alkyl, hydroxy-(1–3C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C) alkoxy-(1–3C)alkyl, carboxy-(1–4C)alkyl, (1–4C) alkoxycarbonyl-(1–4C)alkyl, carbamoyl-(1–4C)alkyl, N-(1–4C)alkylcarbamoyl-(1–4C)alkyl, N, N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, (1–4C)alkoxy, cyano-(1–4C) alkoxy, carbamoyl-(1–4C)alkoxy, N-(1–4C)alkylcarbamoyl-(1–4C)alkoxy, N, N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C) alkanoyloxy-(2–4C)alkoxy, 2-(1–4C)alkoxyethoxy, carboxy-(1–4C)alkoxy, (2–4C)alkenyloxy, (2–4C)alkynyloxy, (1–4C)alkylthio, (1–4C)alkylsulphinyl, (1–4C) alkylsulphonyl, ureido, carbamoyl, N-[(1–4C)alkyl]carbamoyl, N,N-di-[(1–4C)alkyl]carbamoyl, amino, (1–4C) alkylamino, di-[(1–4C)alkyl]amino, (2–4C) alkanoylamino, phenyl-(1–4C)alkyl, phenyl-(1–4C) alkoxy, phenyl, naphthyl, benzoyl and a 5- or 6-membered aromatic heterocycle (linked via a ring carbon atom and containing one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenyl-(1–4C)alkoxy substituents may optionally bear one or two substituents independently selected from halogeno, (1–4C)alkyl and (1–4C)alkoxy; or a pharmaceutically-acceptable salt or in-vivo-hydrolysable ester thereof.

In the above mentioned embodiments, yet further embodiments are those as described above but in which $Q_1$ does not bear any of the additional substituents that contain a phenyl group, for example a phenyl-(1–4C)alkyl substituent.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (a) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy-(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C) alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and a-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl include chloromethyl, aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification. Further suitable in-vivo hydrolysable esters of a compound of the formula (I) are described as follows. For example, a 1,2-diol may be cyclised to form a cyclic ester of formula (PD1) or a pyrophosphate of formula (PD2):

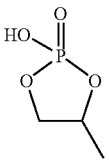
(PD1)

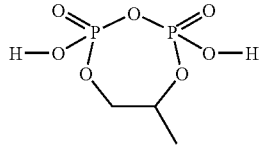
(PD2)

Esters of compounds of formula (I) wherein the HO-function/s in (PD1) and (PD2) are protected by (1–4C)alkyl, phenyl or benzyl are useful intermediates for the preparation of such pro-drugs.

Further in-vivo hydrolysable esters include phosphoramidic esters, and also compounds of formula (I) in which any free hydroxy group independently forms a phosphoryl (npd is 1) or phosphiryl (npd is 0) ester of the formula (PD3):

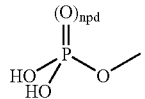
(PD3)

Useful intermediates for the preparation of such esters include compounds containing a group/s of formula (PD3) in which either or both of the —OH groups in (PD3) is independently protected by (1–4C)alkyl, phenyl or phenyl-(1–4C)alkyl (such phenyl groups being optionally substituted by 1 or 2 groups independently selected from (1–4C) alkyl, nitro, halo and (1–4C)alkoxy).

Thus, prodrugs containing groups such as (PD1), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection.

When a compound of formula (I) contains a number of free hydroxy group, those groups not being converted into a prodrug functionality may be protected (for example, using a t-butyl-trimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO-P-functionalites present in the overall molecule, each of which may form an appropriate salt (i.e. the overall molecule may form, for example, a mono-. di-, tri- or tetra-sodium salt).

Some compounds of the formula (I) may have chiral centres and/or geometric isomeric centres (E- and Z-isomers), and it is to be understood that the invention encompasses all such optical, diastereo-isomers and geometric isomers, and mixtures thereof, that possess CDK and/or FAK inhibitory activity.

The invention relates to any and all tautomeric forms of the compounds of the formula (I) that possess CDK and/or FAK inhibitory activity.

It is also to be understood that certain compounds of the formula (I) can exist in solvated as well as unsolvated forms such as, for example, hydrated forms. It is to be understood that the invention encompasses all such solvated forms which possess CDK and/or FAK inhibitory activity.

Particular preferred compounds of the invention comprise a pyrimidine derivative of the formula (I), or pharmaceutically-acceptable salt or in-vivo hydrolysable ester thereof, wherein $R^1$, $Q_1$, $Q_2$, X, Y, Z, m and n have any of the meanings defined hereinbefore, or any of the following values. Such values may be used where appropriate with any of the definitions, claims or embodiments defined hereinbefore or hereinafter.

(a0) When $Q_1$ or $Q_2$ is indanyl or 1,2,3,4-tetrahydronaphthyl, it is linked via the unsaturated ring; preferably $Q_1$ and/or $Q_2$ are phenyl;

(a1) $R^1$ is preferably hydrogen in one embodiment;

(a2) In another embodiment $R^1$ is preferably hydrogen, benzyl, (3–5C)alkynyl (especially propyn-2-yl), (3–6C) cycloalkyl-(1–6C)alkyl (especially cyclopropylmethyl), (1–4C)alkyl [optionally substituted by one or two substituents selected from hydroxy, amino, halo, trifluoromethyl and cyano] or (3–5C)alkenyl substituted by one to three halo groups;

(b) $R^1$ is preferably benzyl, (3–5C)alkynyl (especially propyn-2-yl), (3–6C)cycloalkyl-(1–6C)alkyl (especially cyclopropylmethyl), (1–4C)alkyl [optionally substituted by one substituent selected from hydroxy, amino, halo, trifluoromethyl and cyano] or (3–5C)alkenyl substituted by one halo group;

(c) $R^1$ is more preferably (3–5C)alkynyl (especially propyn-2-yl) or (1–4C)alkyl [optionally substituted by trifluoromethyl or cyano] or (3–5C)alkenyl substituted by one bromo group;

(d) $R^1$ is most preferably propyn-2-yl, (1–4C)alkyl substituted by one trifluoromethyl or one cyano group (especially cyanomethyl or 2-cyanoethyl) or (3–5C)alkenyl substituted by one bromo group (especially —CH$_2$CH=CHBr);

(e) $R^1$ is most especially preferred as —CH$_2$CH=CHBr, —CH$_2$CH$_2$CH$_2$CF$_3$ or —CH$_2$CH=CH-phenyl;

(e1) In another embodiment $R^1$ is preferred as propyn-2-yl, cyanomethyl, 2-cyanoethyl, —CH$_2$CH=CHBr or —CH$_2$CH$_2$CH$_2$CF$_3$ (especially —CH$_2$CH$_2$CH$_2$CF$_3$);

(f) In one embodiment Z is preferably —NH(1–4C)alkyl, —N[(1–4C)alkyl]$_2$, —NH—(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino; or alternatively Z is NH$_2$;

(f1) In one embodiment Y is preferably H, OH, SH, NH$_2$, (1–4C)alkoxy, (1–4C)alkylthio, —NH(1–4C)alkyl, —N[(1–4C)alkyl]$_2$ or —NH—(3–8C)cycloalkyl; especially H or OH;

(f2) In one embodiment X is preferably O or NH or NRx; least preferred is X as S;

(f3) Preferably n+m is less than 5;

(f3) Preferably in the substituent of formula (Ia) X is O, Y is H or OH and Z is —NH(1–4C)alkyl, —N[(1–4C)alkyl]$_2$ or —NH—(3–8C)cycloalkyl; preferably n is 1 and m is 1;

(f4) In another embodiment in the substituent of formula (Ia) X is O, Y is OH and Z is —N[(1–4C)alkyl]$_2$; preferably n is 1 and m is 1;

(g) Most preferably the substituent of formula (Ia) is 3-dimethylamino-2-hydroxypropoxy;

(h) Preferably there is one substituent of formula (Ia), and this substituent is in ring Q$_1$;

(i) When the substituent of formula (Ia) is in Q$_1$ it must be in either the para- or meta-position relative to the —NH—, preferably in the para-position;

(j) Preferably Q$_1$ bears no further substituents (other than (Ia)); preferable further substituents for Q$_2$ include halo, hydroxy-(1–3C)alkyl, fluoro-(1–4C)alkyl (especially trifluoromethyl), morpholino and (1–4C)alkyl (especially methyl);

(k) More preferable further substituents for Q$_2$ include halo, morpholino and (1–4C)alkyl (especially methyl);

(l) Preferably the ring Q$_1$ or Q$_2$ not bearing the substituent of formula (Ia) is substituted by one or two further substituents, preferably halo, morpholino and/or (1–4C)alkyl (especially methyl);

(m) Most preferably the ring Q$_1$ bears the substituent of formula (Ia) and Q$_2$ is substituted by one or two further substituents, selected preferably from halo, hydroxy-(1–3C)alkyl, fluoro-(1–4C)alkyl (especially trifluoromethyl), morpholino and (1–4C)alkyl (especially methyl).

A preferred compound of the invention is a pyrimidine derivative of the formula (I), or pharmaceutically-acceptable salt or in-vivo hydrolysable ester thereof as claimed in any of claims 1 to 5 and wherein (i) Q$_2$ does not bear any optional further substituents of formula (Ia) and/or (ii) there is one substituent of formula (Ia), borne by Q$_1$ and/or (iii) in claims 1 or 2 Q$_1$ does not bear any of the additional two further substituents that are listed.

A further preferred compound of the invention is a pyrimidine derivative of the formula (I), or pharmaceutically-acceptable salt or in-vivo hydrolysable ester thereof, wherein:

Q$_1$ and Q$_2$ are both phenyl;

R$^1$ is hydrogen or (1–4C)alkyl substituted by one cyano group (especially cyanomethyl); or alternatively R$^1$ is —CH$_2$CH═CHBr or —CH$_2$CH$_2$CH$_2$CF$_3$ (especially —CH$_2$CH$_2$CH$_2$CF$_3$) or —CH$_2$CH═CH-phenyl;

Q$_1$ bears one substituent of formula (Ia) (especially 3-dimethylamino-2-hydroxypropoxy), preferably in the para-position;

Q$_2$ bears one or two substituents independently selected from halo, morpholino and (1–4C)alkyl (especially methyl).

A specific preferred compound of the invention is the following pyrimidine derivative of the formula (I):

2-{4-[3-(N,N-Dimethyl)amino-2-hydroxy-propoxy]anilino}-4-(2-bromo-4-methylanilino)pyrimidine 2-{4-[3-(N,N-Dimethyl)amino-2-hydroxy-propoxy]anilino}-4-(2,5-dichloroanilino)pyrimidine; or pharmaceutically-acceptable salt or in-vivo hydrolysable ester thereof.

Other specific preferred compounds of the invention are the pyrimidine derivatives of the formula (I), described in Examples 9, 20, 27, 29, 32, 56, 60, 37, 41, 42, 78, 80 and 82, or pharmaceutically-acceptable salts or in-vivo hydrolysable esters thereof.

Process Section

A pyrimidine derivative of the formula (I), or a pharmaceutically-acceptable salt or an in vivo hydrolysable ester thereof, may be prepared by any process known to be applicable to the preparation of chemically-related compounds. Such processes, when used to prepare a pyrimidine derivative of the formula (I), or a pharmaceutically-acceptable salt or an in vivo hydrolysable ester thereof, are provided as a further feature of the invention and are illustrated by the following representative examples in which, unless otherwise stated R$^1$, Q$_1$, Q$_2$, X, Y, Z, m and n have any of the meanings defined hereinbefore for a pyrimidine derivative of the formula (I) and unless another substituent is drawn on ring Q$_1$ or Q$_2$ the ring may bear any of the substituents described hereinbefore (optionally protected as necessary). Where a substituent is drawn on ring Q$_1$, this includes (unless stated otherwise) the possibilities of the substituent/s being on ring Q$_2$ in addition to, or instead of the substituent being on ring Q$_1$. Where X is defined in this process section as NH it is to be understood that this also includes the possibility of X as NRx.

Necessary starting materials may be obtained by standard procedures of organic chemistry (see, for example, Advanced Organic Chemistry (Wiley-Interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

Thus, as a further feature of the invention there are provided the following processes which comprises of:

a) reacting a pyrimidine of formula (II):

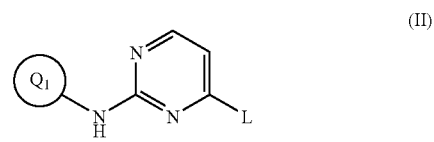

wherein L is a displaceable group as defined below, with a compound of formula (III):

b) reaction of a pyrimidine of formula (IV):

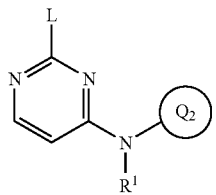
(IV)

wherein L is a displaceable group as defined below, with a compound of formula (V):

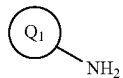
(V)

c) for compounds of formula (I) wherein n is 1, 2 or 3; m=1 and Y is OH, $NH_2$ or SH:

reaction of a 3-membered heteroalkyl ring of formula (VI):

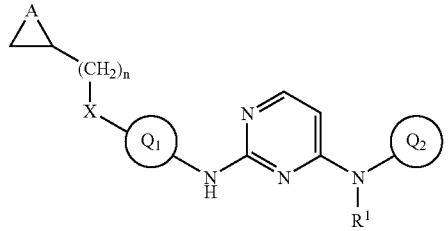
(VI)

wherein A is O, S or NH;

with a nucleophile of formula (VII):

Z—D  (VII)

wherein D is H or a suitable counter-ion;

d) for compounds of formula (I) where X is oxygen:

by reaction of an alcohol of formula (VIII):

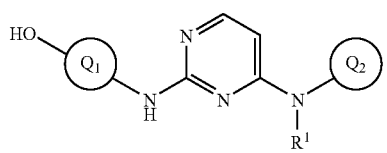
(VIII)

with an alcohol of formula (IX):

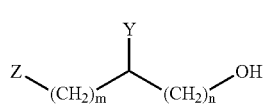
(IX)

e) for compounds of formula (I) wherein X is $CH_2$, O, NH or S; Y is OH and m is 2 or 3:

reaction of a compound of formula (X):

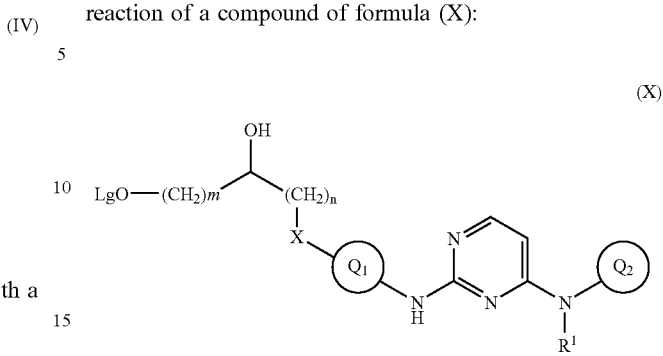
(X)

wherein —OLg is a leaving group such as mesylate or tosylate; with a nucleophile of formula Z—D (VII) wherein D is H or a suitable counter-ion;

f) for compounds of formula (I) wherein X is $CH_2$, O, NH or S; Y is H; n is 1, 2 or 3 and m is 1, 2 or 3:

reaction of a compound of formula (XI):

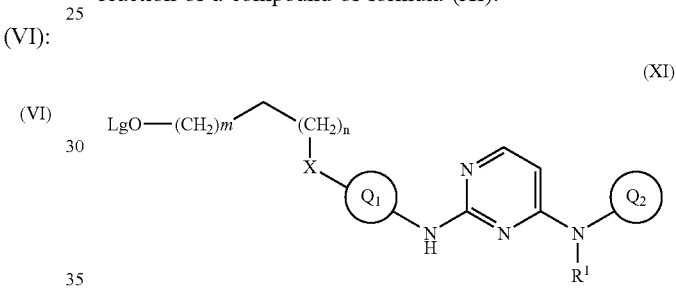
(XI)

wherein —OLg is a leaving group such as mesylate or tosylate; with a nucleophile of formula Z—D (VII) wherein D is H or a suitable counter-ion;

g) for compounds of formula (I) wherein X is O, NH or S; Y is H; n is 1, 2 or 3 and m is 1, 2 or 3:

reaction of a compound of formula (XII) with a compound of formula (XIII):

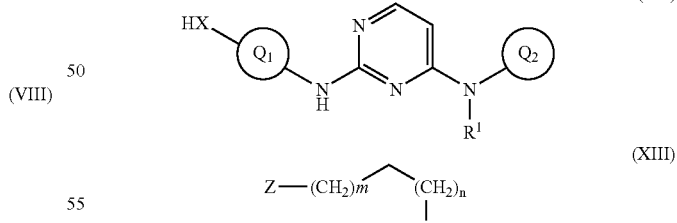
(XII)
(XIII)

(h) for compounds of formula (I) in which Z is SH, by conversion of a thioacetate group in a corresponding compound;

and thereafter if necessary:

i) converting a compound of the formula (I) into another compound of the formula (I);

ii) removing any protecting groups;

iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

D is hydrogen or a counter-ion. When D is a counter-ion, suitable values for D include sodium and potassium.

Specific reaction conditions for the above reactions are as follows:

Process a)

Pyrimidines of formula (II) and anilines of formula (III) may be reacted together i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2-dimethoxyethane, N,N-dimethylformamide, N,N-dimethylacetamide or N-methylpyrrolidin-2-one, and at a temperature in the range, for example, 0° to 150° C., conveniently at or near reflux temperature; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

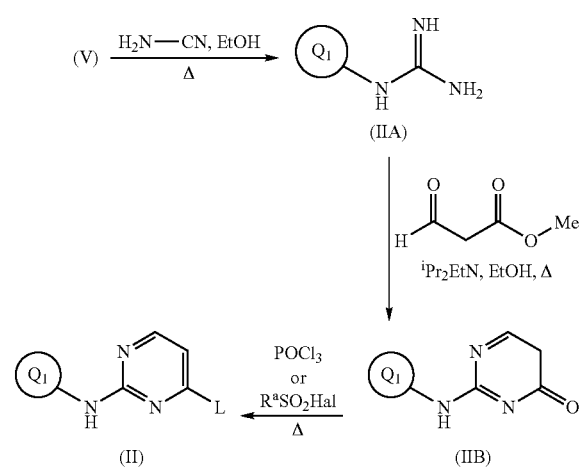

wherein $R^a$ is an optionally substituted alkyl or aryl group. Preferably $R^a$ is methyl, ethyl or p-tolyl.

Anilines of formula (III) are commercially available or are prepared by processes known in the art.

Process b)

Pyrimidines of formula (IV) and anilines of formula (V) may be reacted together, i) in the presence of a suitable solvent for example a ketone such as acetone or an alcohol such as ethanol or butanol or an aromatic hydrocarbon such as toluene or N-methyl pyrrolidine, optionally in the presence of a suitable acid such as those defined above (or a suitable Lewis acid) and at a temperature in the range of 0° C. to reflux, preferably reflux; or ii) under standard Buchwald conditions as described above.

Pyrimidines of formula (IV) are prepared according to the following scheme:

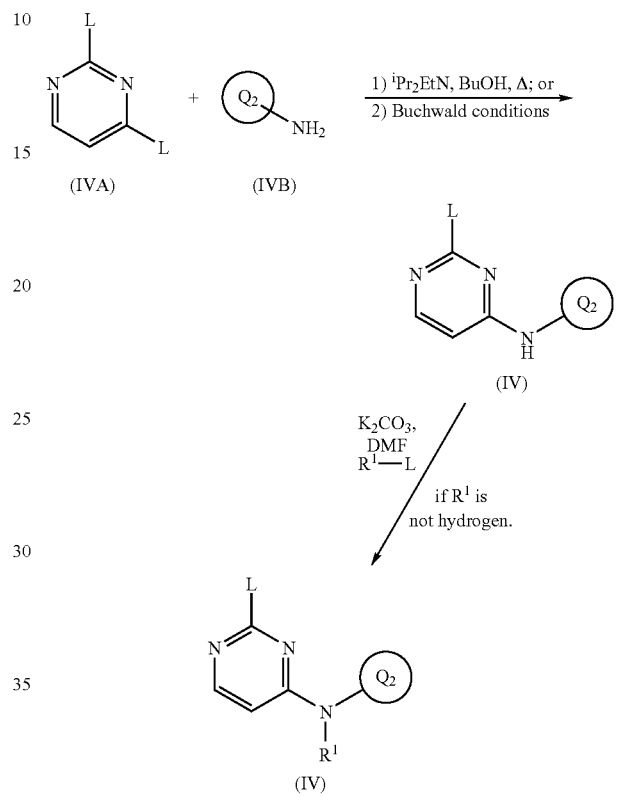

wherein L is a displaceable group as defined above and R1 is not hydrogen.

The anilines of formula (V) are commercially available or are prepared by processes known in the art.

Process c)

Three membered heteroalkyl rings of formula (VI) and nucleophiles of formula (VII) are reacted together at a temperature in the range of 20° to 100° C., preferably 20° to 50° C., optionally in the presence of a suitable solvent, for example N,N-dimethylformamide, dimethyl sulphoxide or tetrahydrofuran.

Compounds formula (VI) may be prepared according to the following schemes:

Scheme I) For compounds of formula (VI) where A is O, and X is not carbon:

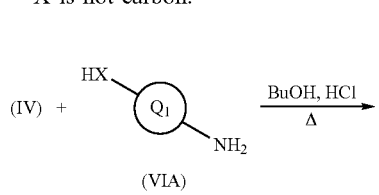

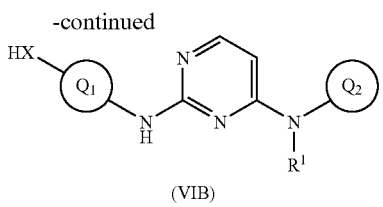

(VIB)

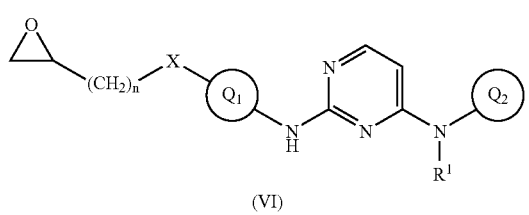

The conversion of (VIB) to (VI) may also be achieved by reaction with Br—(CH$_2$)$_n$—CHO, or an equivalent ester, in DMF and the presence of a base, followed by reaction with a sulfur ylide such as (Me$_2$SOCH$_2$) in an inert solvent such as THF (see Scheme V).

Scheme II For compounds of formula (VI) where A is NH, and X is not carbon:

(for PhINTs see, for example, Tet. Let., 1997, 38 (39), 6897–6900; compounds of formula (VIC) may also be oxidised to the epoxide using conditions similar to that in Scheme IV) below);

Scheme III) For compounds of formula (VI) where A is S, and X is not carbon:

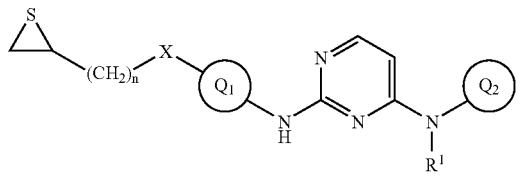

(for example see *Synlett*, 1994, 267–268);

Scheme IV For compounds of formula (VI) where X is carbon:

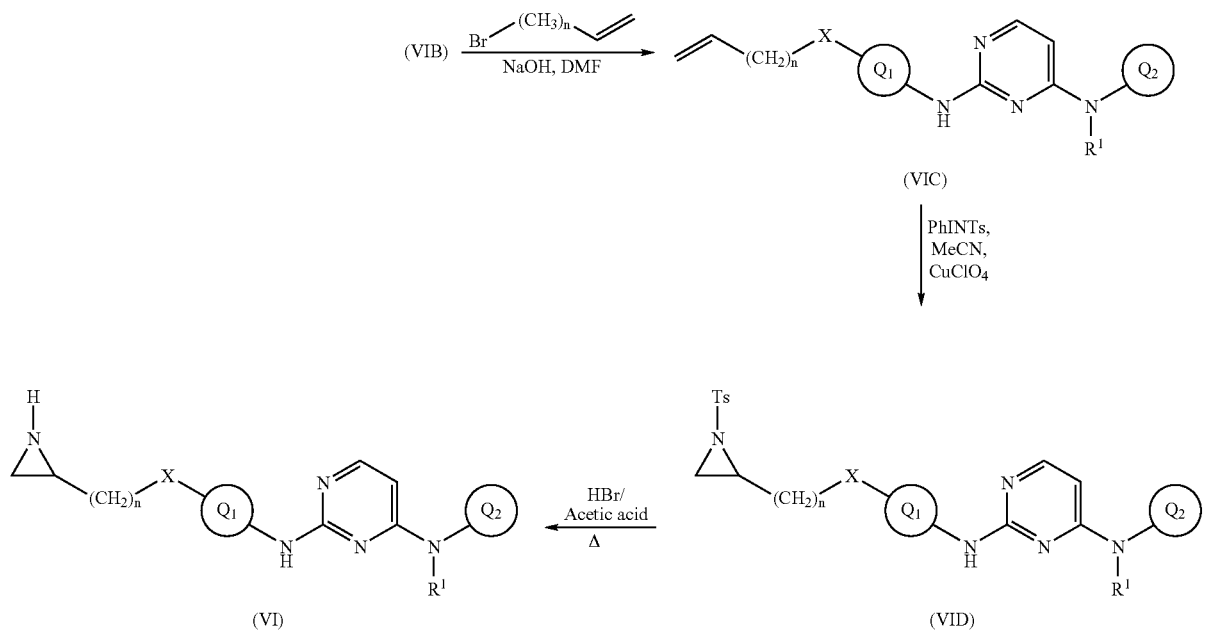

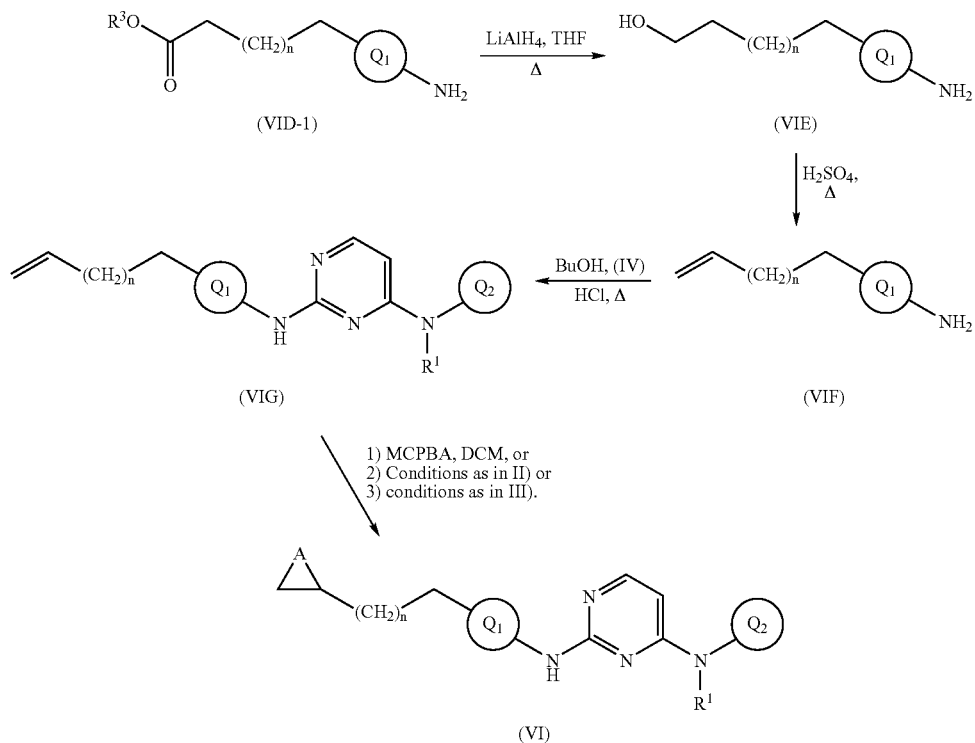

wherein R³ together with the —COO— group to which it is attached forms an ester moiety, for example a methyl ester or an ethyl ester.

Scheme V) For compounds of formula (VI) wherein X is CH₂, O, NH or S; Y is OH; n is 1, 2 or 3 and m is 1:

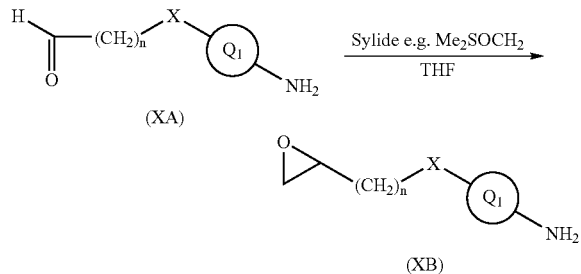

(XB) is reacted with (IV) (see Scheme I) to give (VI).

An equivalent ester of (XA) may also be used. See also Russ.Chem. Rev. 47, 975–990, 1978.

Compounds of formula (XA), (VII), (VIA) and (VID-1) are commercially available or are prepared by processes known in the art.

Process d)

Alcohols (eg. phenols) of formula (VIII) and alcohols of formula (IX) can be reacted together under standard Mitsunobu conditions. For example in the presence of diethyl azodicarboxylate and triphenyl phosphine, in a suitable solvent such as dichloromethane, toluene or tetrahydrofuran, and at a temperature in the range of 0° to 80° C., preferably in the range of 20° to 60° C.

Alcohols of formula (VIII) are made according to the process in I) above for the synthesis of intermediate (VIB) (where X is oxygen), Alcohols of formula (IX) are commercially available or are made by processes known in the art.

In a process analogous to process d), compounds in which X is S may be prepared by reaction of a compound of formula (VIII) in which the hydroxy group is —SH, with a compound of formula (IX) in which the hydroxy group is a leaving group such as mesylate or tosylate.

Process e)

Compounds of formula (X) wherein X is CH₂, O, NH or S; Y is OH and m is 2 or 3 and nucleophiles of formula (VII) are reacted together at a temperature in the range of 20° to 100° C., preferably 20° to 50° C., optionally in the presence of a suitable solvent, for example N,N-dimethylformamide, dimethyl sulphoxide or tetrahydrofuran, and optionally in the presence of a suitable base, such as potassium carbonate.

Compounds of formula (X) are prepared according to the following scheme (m is 2 or 3):

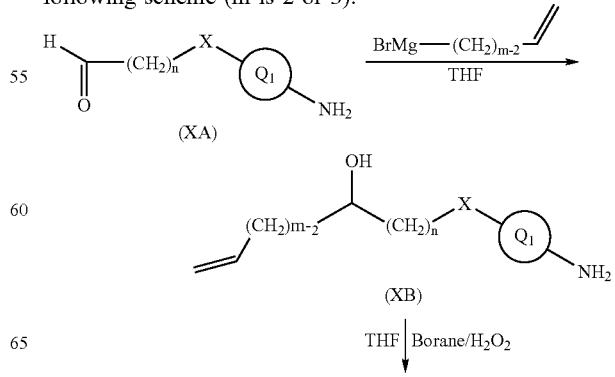

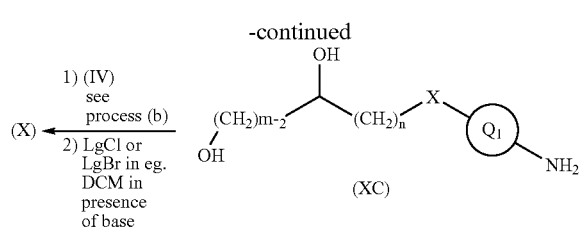

The steps 1) and 2) in the final step may be reversed. A suitable base for step 2) is triethylamine.

Compounds of formula (XA) and (VII) are commercially available or are prepared by processes known in the art. For example, compounds of formula (XA) in which X is NH, O or S may be prepared by reaction of a compound of formula (VIA) with a suitable haloaldehyde or equivalent ester under standard conditions for such reactions.

Process f)

Compounds of formula (XI) and nucleophiles of formula (VII) are reacted together as described for process e) above.

Compounds of formula (XI) are prepared in an analogous manner to step 2) in the final step of the process for preparing compounds of formula (X) above. The necessary primary alcohol starting materials are commercially available or are prepared by processes known in the art Process g)

Compounds of formula (XII) and (XIII) are reacted in an inert solvent such as DMF in the presence of a base such as potassium carbonate.

Compounds of formula (XII) are of the same generic formula as compounds of formula (VIB) described herein and are prepared as described for those compounds (see Scheme I). Compounds of formula (XIII) are commercially available or are prepared by processes known in the art.

Process h)

For the compounds of formula (I) in which Z is SH, the conversion of a thioacetate group in a corresponding compound is carried out as described herein for the conversion of compounds of formula (IJ) into (IK).

Suitable starting materials containing a thioacetate group are prepared from corresponding compounds containing a leaving group such as mesylate or tosylate (prepared using standard conditions from the corresponding hydroxy compound) using thiol acetic acid as described herein for the conversion of compounds of formula (IG) into (IJ).

Examples of conversions of a compound of formula (I) into another compound of formula (I) are:

Conversion i): conversion of $R^1$ as hydrogen into other $R^1$ for example:

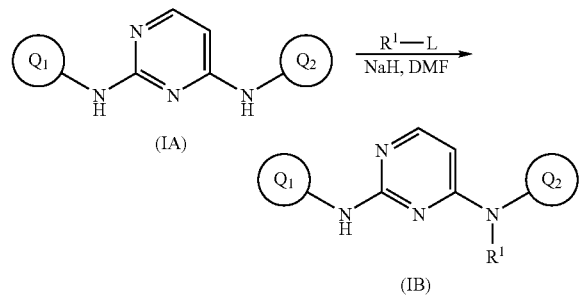

wherein L is a displaceable group as defined above and $R^1$ in the above diagram is not equal to hydrogen;

Conversion ii): conversion of $R^1$ as a substituted side chain into another substituted side chain, for example:

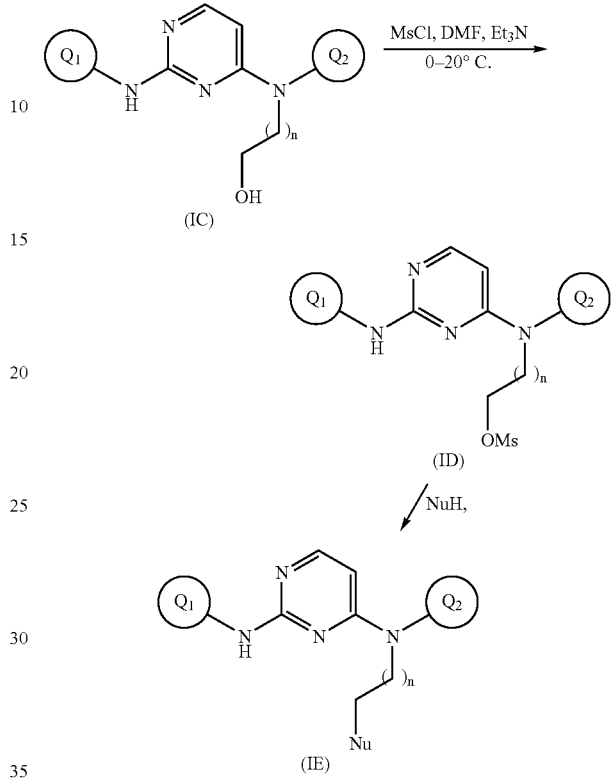

wherein Ms is methanesulphonyl, and Nu is a nucleophile that introduces a substituent that is an optional substituent for $R^1$ as defined in formula (I), such as Nu is —$NH_2$, —$NHC_{1-4}$alkyl, —$N(C_{1-4}$alkyl$)_2$ or —CN (NB the hydroxyl moiety does not necessarily have to be on the terminal carbon as depicted above);

Conversion iii): conversion of one side chain of formula (IA) into another side chain of formula (IA), for example:

Example I for compounds of formula (I) where Y is $NH_2$ (depicted below using ammonia), (1–4C)alkoxy, (1–4C)alkylthio, —NH(1–4C)alkyl, —N[(1–4C)alkyl]$_2$, —NH—(3–8)cycloalkyl, pyrrolidin-1-yl, piperidin-1-yl, piperazin-1-yl, morpholino dr thiomorpholino;

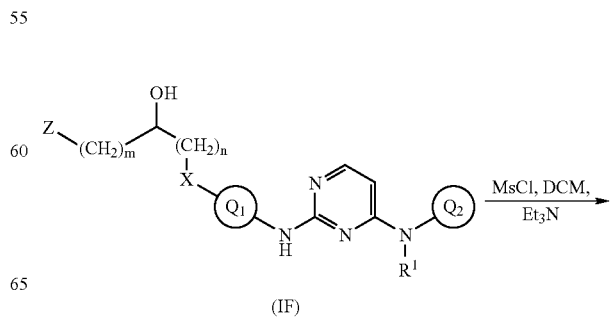

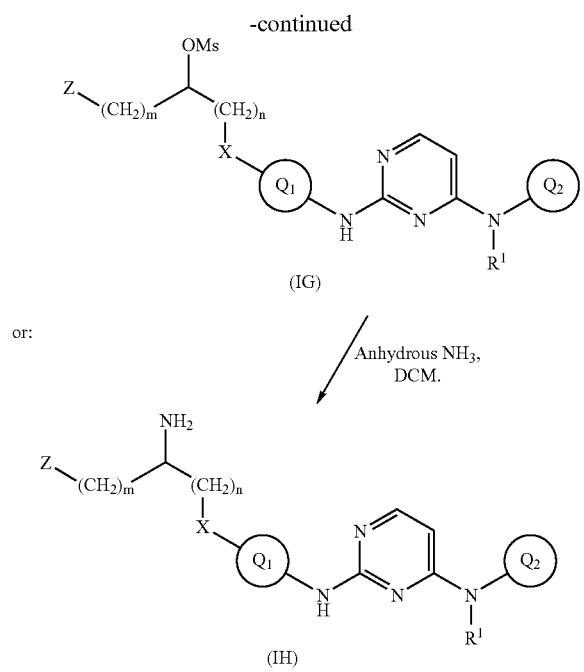

or:

Example II
for compounds of formula (I) where Y is S:

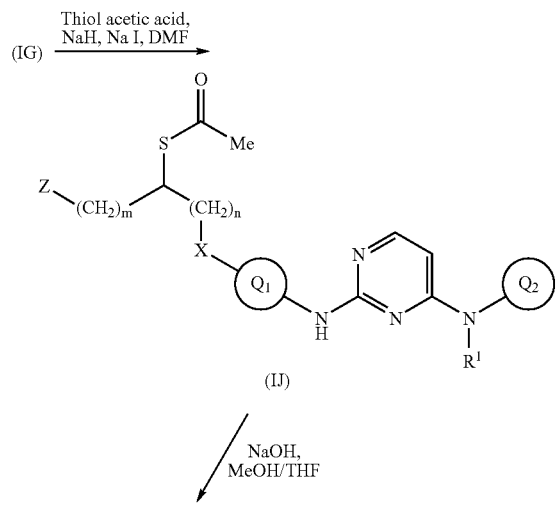

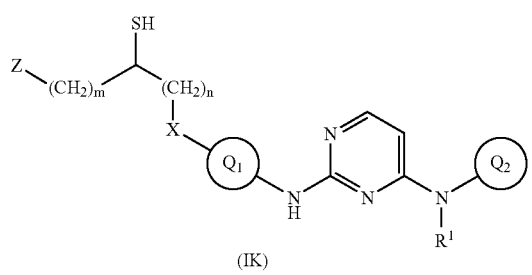

Example III
for compounds of formula (I) where Y is H:

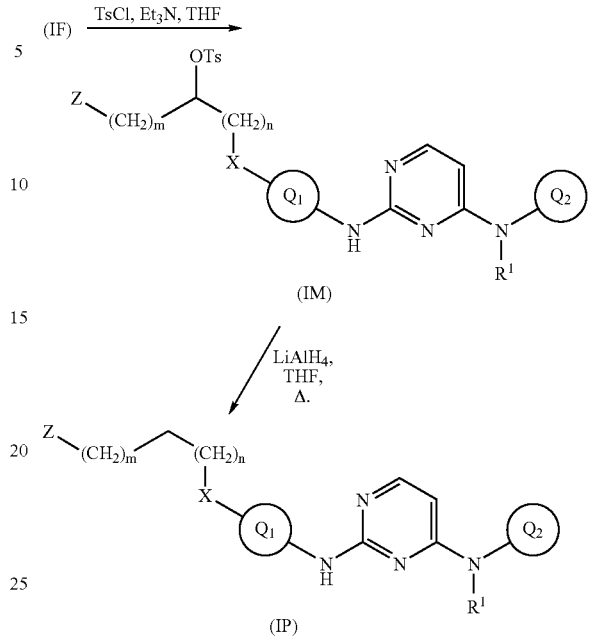

The skilled reader will appreciate that the manipulation of the side chain (IA) described in Processes c), d), e), f), g) and h) and Conversion iii) above and of the sidechain R¹ in Conversion i) and ii) above may also be performed on intermediates, for example, to make intermediates of formula (II), (IIA), (IIB), or (V). For example:

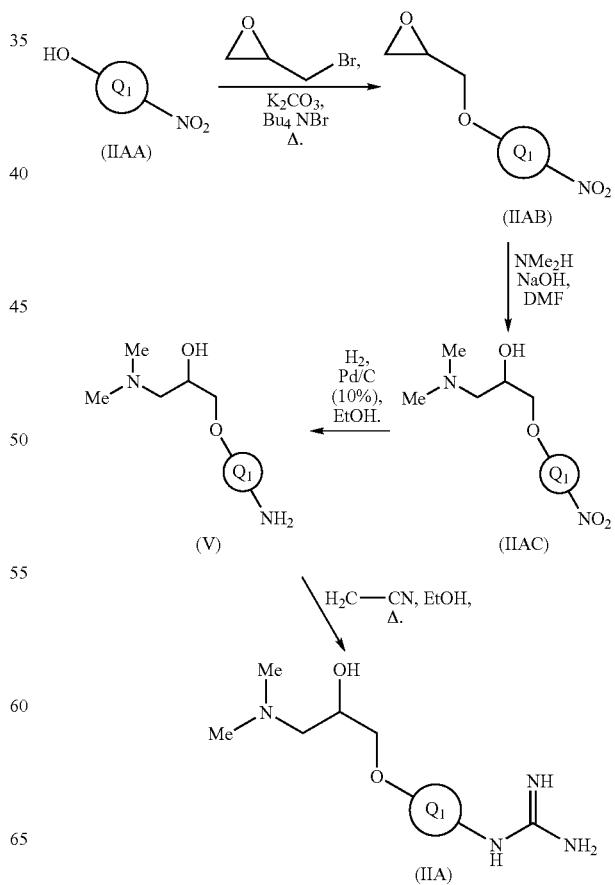

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula (II) and (IV) and these are provided as a further feature of the invention.

Assays

As stated hereinbefore the pyrimidine derivative defined in the present invention possesses anti-cell-proliferation activity such as anti-cancer activity which is believed to arise from the CDK and/or FAK inhibitory activity of the compound. These properties may be assessed, for example, using the procedure set out below:

CDK Inhibition Assay

The following abbreviations have been used:
HEPES is N-[2-Hydroxyethyl]piperazine-N'-[2-ethanesulfonic acid]
DTT is Dithiothretiol
PMSF is Phenylmethylsulfonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma). In each well was placed the compound to be tested (diluted in DMSO and water to correct concentrations) and in control wells either p16 as an inhibitor control or DMSO as a positive control.

Approximately 0.5 μl of CDK4/Cyclin D1 partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM $MnCl_2$, 1 mM DTT, 100 μM Sodium vanadate, 100 μM NaF, 10 mM Sodium Glycerophosphate, BSA (1 mg/ml final).

As a control, another known inhibitor of CDK4 may be used in place of p16.

Test Substrate

In this assay only part of the retinoblastoma (Science Mar. 13, 1987;235(4794):1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac I$^q$ gene for use in any E.Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in *E. Coli* (BL21 (DE3) pLysS cells) using standard inducible expression techniques, and purified as follows.

*E. coli* paste was resuspended in 10 ml/g of NETN buffer (50 mM Tris pH 7.5, 120 mM NaCl, 1 mM EDTA, 0.5% v/v NP-40, 1 mM PMSF, 1 µg/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, imM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from MCF-7 cell line (obtained from ATCC number: HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell 1992 Oct. 16; 71(2): 323–334; Matsushime H., Ewen M. E., Stron D. K., Kato J. Y., Hanks S. K., Roussel M. F., Sherr C. J. and Cyclin D1 amino acids 1–296; Ref. Cold Spring Harb. Symp. Quant. Biol., 1991; 56:93–97; Arnold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V1392-20). The PCR products were then dually expressed [using a standard virus Baculogold co-infection technique] into the insect SF21 cell system (Spodoptera Frugiperda cells derived from ovarian tissue of the Fall Army Worm—commercially available).

The following Example provides details of the production of Cyclin D1l/CDK4 in SF21 cells (in TC100+10% FBS (TCS)+0.2% Pluronic) having dual infection MOI 3 for each virus of Cyclin D1 & CDK4.

Example Production of Cyclin D1/CDK4

SF21 cells grown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

$$\text{Cyclin D1} \quad \frac{1.86 \times 10E6 \times 500 \times 3}{0.9 \times 10^8} = 31 \text{ ml of virus for each 500 ml. bottle.}$$

$$\text{CDK4} \quad \frac{1.86 \times 10E6 \times 500 \times 3}{1 \times 10^8} = 28 \text{ ml of virus for each 500 ml. bottle}$$

The viruses were mixed together before addition to the cultures, and the cultures returned to the roller rig 28° C.

After 3 days (72 hrs.) post infection the 5 Liters of culture was harvested. The total cell count at harvest was 1.58×10E6 cells/ml. (99% viable). The cells were spun out at 2500 rpm, 30 mins., 4° C. in Heraeus Omnifuge 2.0 RS in 250 mls. lots. The supernatant was discarded.

20 pellets of ~4×10E8 cells/pellet were snap frozen in $LN_2$ and stored at −80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, 0.1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.4/100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US).

p16 Control (Nature 366.:704–707: 1993: Serrano M, Hannon G J, Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref. Studier F. W. and Moffat B. A., J. Mol. Biol., 189, 113, 1986). A 1 liter culture was grown to the appropriate OD then induced with IPTG to express p16 overnight. The cells were then lysed by sonication in 50 mM sodium phoshate, 0.5M sodium chloride, PMSF, 0.5 µg/mL leupeptin and 0.5 µg/mL aprotinin. The mixture was spun down, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

pTB375

The background vector used for generation of pTB 375 was pZEN0042 (see UK patent 2253852) and contained the tetA/tetR inducible tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzymes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

If using CDK-2 with Cyclin E partial co-purification may be achieved as follows: Sf21 cells are resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant is loaded onto a Poros HQ/M 1.4/100 anion exchange column (PE Biosystems, Hertford, UK). CDK-2 and Cyclin E are coeluted at the beginning of a 0–1M NaCl gradient (run in lysis buffer minus protease inhibitors) over 20 column volumes. Co-elution is checked by western blot using both anti-CDK-2 and anti-Cyclin E antibodies (Santa Cruz Biotechnology, California, US).

FAK3 Kinase Inhibition Assay

This assay determines the ability of a test compound to inhibit tyrosine kinase activity of human Focal Adhesion Kinase (FAK).

DNA encoding FAK is obtained by total gene synthesis (Edwards M, International Biotechnology Lab 5(3), 19–25, 1987) or by cloning. These are then expressed in a suitable expression system to obtain polypeptide with tyrosine kinase activity. For example, FAK, obtained by expression of recombinant protein in insect cells, was found to display intrinsic tyrosine kinase activity.

FAK (full length human cDNA described by Andre et al (Biochemical and Biophysical Research Communications, 1993, 190 (1): 140–147; EMBL/GenBank Accession Number L05186)) was modified such that the resulting protein when translated had a 6-histidine tag at the N-terminus immediately preceding the start methionine. Active FAK protein has been previously expressed in a baculovirus system using a similar N-terminal 6-histidine tag (Protein Expression And Purification, 1996, 7: 12–18). The human FAK cDNA was cloned into the baculovirus transplacement vector, pFastbac 1 (Life Technologies), and the recombinant construct was co-transfected into insect cells (for example Spodoptera frugiperda 21(Sf21)) with viral DNA to prepare recombinant baculovirus (details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York. Details specific to the use of the pFastbac ('Bac to Bac') system are provided in Anderson et al., 1995, FOCUS (Life Technologies Bulletin Magazine), 17, p 53.)

For expression of biologically active human FAK protein, Sf21 cells were infected with plaque-pure FAK recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold lysis buffer (50 mM HEPES pH7.5, 1 mM Dithiothreitol, 100 uM Sodium Fluoride, 100 uM Sodium Orthovanadate, 10 mM Glycerophosphate, 100 uM Phenylmethylsulphonylfluoride (PMSF), 5 ug/ml Aprotinin, 5 ug/ml Leupeptin, 1% Tween; the PMSF being added just before use from a freshly-prepared 100 mM solution in methanol) using 250 ul lysis buffer per 10 million cells. The suspension was then incubated on ice for 15 minutes and centrifuged for 10 minutes at 13,000 rpm at 4° C. The supernatant (enzyme stock) was removed and aliquots made which were snap frozen in liquid nitrogen and then stored at −70° C. For a typical batch, stock enzyme was diluted 1 in 250 with enzyme diluent ((100 mM HEPES pH 7.4, 0.2 mM Dithiothreitol, 200 uM Sodium Orthovanadate, 0.1% Triton X-100) and 50 ml of freshly diluted enzyme was used for each assay well (see FAK3 protocol, below).

FAK3: In Vitro Enyme Assay Protocol

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Maxisorp 96 well immunoplates Life technologies, Cat. No. 439454A) which were sealed with plate sealers and left overnight at 4° C.

On the day of the assay the substrate solution was discarded and the assay plate wells were washed once with 200 ul PBST (PBS containing 0.05% v/v Tween 20) and once with 200 ul 50 mM Hepes pH7.4.

Test compounds were made up as 10 mM or 30 mM stocks in DMSO and then further diluted in glass distilled water diluted to a concentration 10 fold higher than the final assay concentration. 10 µl of diluted compound was transferred to wells in the washed assay plates. "No compound" control wells contained 10 ul glass distilled water instead of compound.

Forty microliters of 25 mM manganese chloride containing 6.25 µM adenosine-5'-triphosphate (ATP) was added to all test wells. To start the reactions 50 µl of freshly diluted enzyme was added to each well and the plates were incubated at 23C for 90 minutes. Then the reaction was stopped by adding 100 ul of PBS containing 20 mM EDTA. The liquid was then discarded and the wells were washed twice with PBST.

One hundred microliters of mouse HRP-linked anti-phosphotyrosine antibody (Santa Cruz, Product SC 7020-HRP), diluted 1 in 1500 with PBST containing 0.5% w/v bovine serum albumin (BSA), was added to each well and the plates were incubated for 1 hour at room temperature before discarding the liquid and washing the wells twice with 200 ul PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the absorbance value of the "no compound" control wells, measured at 405 nm using a plate reading spectrophotometer, was approximately 1.0.

Dose response curves were generated from the absorbance readings using Origin Software. Compounds were ranked for potency using the Inhibitory Concentration 50 (IC50), as defined by Origin Software analysis.

Although the pharmacological properties of the compounds of the formula (I) vary with structural change, in general activity possessed by compounds of the formula (I) in the above assays may be demonstrated at $IC_{50}$ concentrations or doses in the range 250 μM to 1 nM.

When tested in the above in-vitro assays the CDK4 and FAK inhibitory activities respectively of Example 3 were measured as $IC_{50}$=0.6 μM and $IC_{50}$=3.3 μM; and those of Example 11 as $IC_{50}$=0.53 μM and $IC_{50}$=3.1 μM.

The in-vivo activity of the compounds of the present invention may be assessed by standard techniques, for example by measuring inhibition of cell growth and assessing cytotoxicity. For example, further details may be found in the following references:

a) Attenution of the Expression of the Focal Adhesion Kinase induces Apoptosis in Tumor Cells. Xu L-h et al. Cell Growth & Differentiation (1996) 7, p 413–418;
b) The COOH-Terminal Domain of the Focal Adhesion Kinase Induces Loss of Adhesion and Cell Death in Human tumour Cells. Xu L-h et al. Cell Growth & Differentiation (1998) 9, p 999–1005;
c) Inhibition of pp125-FAK in Cultured Fibroblasts Results in Apoptosis. Hungerford J. E et al. The Journal of Cell Biology (1996) 135, p 1383–1390;
d) Inhibition of Focal Adhesion Kinase (FAK) Signalling in Focal Adhesions Decreases Cell Motility and Proliferation. Gilmore A. P and Romer L. H. Molecular Biology of the Cell (1996) 7, p 1209–1224.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 μl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 μl SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically-acceptable salt or in-vivo hydrolysable ester thereof, as defined hereinbefore in association with a pharmaceutically-acceptable diluent or carrier.

The composition may be in a form suitable for oral administration, for example as a tablet or capsule, for parenteral injection (including intraveous, subcutaneous, intramuscular, intravascular or infusion) as a sterile solution, suspension or emulsion, for topical administration as an ointment or cream or for rectal administration as a suppository.

In general the above compositions may be prepared in a conventional mariner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula (I), or a pharmaceutically-acceptable salt or in-vivo hydrolysable ester thereof, as defined hereinbefore for use in a method of treatment of the human or animal body by therapy.

We have found that the pyrimidine derivatives defined in the present invention, or a pharmaceutically-acceptable salt or in-vivo hydrolysable ester thereof, are effective cell cycle inhibitors (anti-cell proliferation agents), which property (without being bound by theory) is believed to arise from their (GI-S phase) CDK inhibitory properties. The compounds are also effective inhibitors of FAK. Accordingly the compounds of the present invention are expected to be useful in the treatment of diseases or medical conditions mediated alone or in part by CDK and/or FAK enzymes, i.e. the compounds may be used to produce a CDK and/or FAK inhibitory effect in a warm-blooded animal in need of such treatment. Thus the compounds of the present invention provide a method for treating the proliferation and/or migration of malignant cells characterised by inhibition of CDK and/or FAK enzymes, i.e. the compounds may be used to produce an anti-proliferative/migration effect mediated alone or in part by the inhibition of CDKs and/or FAK. The compounds may also be useful as FAK inhibitors by inducing cell-death (apoptosis). Such a pyrimidine derivative of the invention is expected to possess a wide range of anti-cancer properties as CDKs and/or FAK have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically-acceptable salt or in-vivo hydrolysable ester thereof, are expected to inhibit the growth of those primary and recurrent solid tumours which are associated with CDKs and/or FAK, especially those tumours which are significantly dependent on CDK and/or FAK for their growth and spread, including for example, certain tumours of the colon, breast, prostate, lung, vulva and skin.

It is further expected that a pyrimidine derivative of the present invention will possess activity against other cell-proliferation/migration diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I), or a pharmaceutically-acceptable salt or in-vivo hydrolysable ester thereof, as defined hereinbefore for use as a medicament; and the use of a pyrimidine derivative of the formula (I), or a pharmaceutically-acceptable salt or in-vivo hydrolysable ester thereof, as defined hereinbefore in the manufacture of a medicament for use in the production of an anti-cancer, cell cycle inhibitory (anti-cell-proliferation) effect and/or a FAK inhibitory (anti-cell migration and/or apoptosis inducing) effect in a warm-blooded animal such as man. Particularly, a cell cycle inhibitory effect is produced at the G1-S phase by inhibition of CDK2, CDK4 and/or CDK6, especially CDK4 and CDK6.

According to a further feature of this aspect of the invention there is provided a method for producing an anti-cancer, cell cycle inhibitory (anti-cell-proliferation) effect and/or a FAK inhibitory (anti-cell migration and/or apoptosis inducing) effect in a warm-blooded animal, such as man, in need of such treatment which comprises administering to said animal an effective amount of a pyrimidine derivative as defined immediately above. Particularly, an inhibitory effect is produced at the G1-S phase by inhibition of CDK2, CDK4 and/or CDK6, especially CDK4 and CDK6.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK and/or FAK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen,toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues. cytosine arabinoside); antitumour antibiotics (for example anthracyclines like doxorubicin, daunomycin, epirubicin and idarubicin. mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) as defined hereinbefore and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

EXAMPLES

The invention will now be illustrated in the following non-limiting Examples, in which standard techniques known to the skilled chemist and techniques analogous to those described in these Examples may be used where appropriate, and in which, unless otherwise stated:

(i) evaporations were carried out by rotary evaporation in vacuo and work-up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC), for example using an Anachem Sympur MPLC, were performed on Merck Kieselgel silica (Art. 9385) or Merck Lichroprep RP-18 (Art. 9303) reversed-phase silica obtained from E. Merck, Darmstadt, Germany; where a Mega Bond Elut column is referred to, this means a column containing 10 g or 20 g of silica of 40 micron particle size. the silica being contained in a 60 ml disposable syringe and supported by a porous disc, obtained from Varian, Harbor City, Calif., USA under the name "Mega Bond Elut SI"; "Mega Bond Elut" is a trademark;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSO (unless otherwise stated); at ambient temperature unless marked 373K; on the delta scale (ppm downfield from tetramethylsilane); using a Varian Gemini 2000 spectrometer operating at a field strength of 300 MHz or a Bruker DPX400 spectrometer operating at a field strength of 400 MHz; and peak multilicities are shown as follows: s, singlet; d, doublet; t, triplet; m, multiplet; br, broad; mass spectrometry (MS) was performed by electrospray on a VG platform;

(vi) intermediates were not generally fully characterised and purity was assessed by thin layer chromatography (TLC), high performance liquid chromatography (HPLC), infrared (IR), MS or NMR analysis;

(vii) it is to be understood that in this Examples section certain symbols, such as $R_1$ and $R_2$, have been used to describe certain Examples in Tables, and that the use of such symbols should be read in context with the Examples to which they refer;

(viii) certain geometric isomers (such as shown in Examples 38 & 42) may exist as E- and Z-isomers; it is to be understood that where one isomer, or no particular isomer, is shown this refers to a mixture of both isomers;

(ix) the following abbreviations may be used hereinbefore or hereinafter:

| | |
|---|---|
| DMF | N,N-dimethylformamide; |
| $CDCl_3$ | deuterated chloroform; |
| MeOH-$\delta_4$ | deuterated methanol; |
| EA | elemental analysis; |
| NMP | 1-methyl-2-pyrrolidinone; |
| DEAD | diethyl azodicarboxylate; |
| DTAD | ditertbutyl azodicarboxylate; |
| EtOH | ethanol; |
| DIPEA | diisopropylethylamine; |
| DCM | dichloromethane; |
| TFA | trifluoroacetic acid; |
| EtOAc | ethyl acetate; and |
| DMSO | dimethylsulphoxide. |

Example 1

2-{4-[3-(N,N-Dimethyl)amino-2-hydroxypropoxy]anilino}-4-(2,5-dimethylanilino)pyrimidine 2-Chloro-4-(2,5-dimethylanilino)pyrimidine (Reference Example A-1; 250 mg, 1.07 mmol) was dissolved in n-butanol (5 ml) and 4-[3-(N,N-dimethyl)amino-2-hydroxypropoxy]aniline hydrochloride (Reference Example D-1; 295 mg, 1.07 mmol) was added. The resulting suspension was treated with methanol until all the solid dissolved. The reaction mixture was heated at 100° C. for 8 hours and allowed to cool to ambient temperature. The reaction mixture was then basified to pH 9–10 using methanolic ammonia and then evaporated onto silica (5 ml). The residue was purified by column chromatography eluting with methanol (15%):DCM:aqueous ammonia (1%). The resulting gum was recrystallized from acetonitrile to give the title product as a solid (104 mg, 24%). NMR (300 MHz): 2.13 (s, 3H), 2.25 (s, 3H), 2.79 (s, 6H), 3.19 (m, 2H), 3.88 (m, 2H), 4.21 (m, 1H), 5.88 (brs, 1H), 6.05 (d, 1H), 6.73 (d, 2H), 6.93 (d, 1H), 7.12 (d, 1H), 7.26 (s, 1H), 7.55 (d, 2H), 7.9 (d, 1H), 8.6 (s, 1H), 8.88 (s, 1H); m/z: ($ES^+$) 408.4 ($MH^+$).

Method A: Displacement of 4-chloro from 2,4-dichloropyrimidine by an aniline

Reference Example A-1

2-Chloro-4-(2,5-dimethylanilino)pyrimidine 2,4-Dichloropyrimidine (500 mg, 3.36 mmol), 2,5-dimethylaniline (407 mg, 3.36 mmol) and triethylamine (0.51 ml, 3.69 mmol) were dissolved in EtOH (5 ml) with stirring. The reaction mixture was heated at reflux for 12 hours, cooled and evaporated onto silica (5 ml). The residue was purified by column chromatography and eluted with EtOAc (30%): isohexane to give the title product as a waxy solid on evaporation (514 mg, 66%). NMR (300 MHz): 2.1 (s, 3H), 2.27 (s, 3H), 6.42 (d. 1H), 6.99 (d, 1H), 7.08 (s, 1H). 7.18 (d, 1H), 8.03 (d, 1H), 9.45 (s, 1H); m/z: ($ES^+$) 234.3 ($MH^+$).

Example 2

2-{4-[3-(N,N-Dimethyl)amino-2-hydroxypropoxy]anilino}-4-(2,4-difluoroanilino)pyrimidine 2-Chloro-4-(2,4-difluoroanilino)pyrimidine (Reference Example A-2; 174 mg, 0.72 mmol) was dissolved in n-butanol (2 ml) and 4-[3-(N,N-dimethyl)amino-2-hydroxypropoxy]aniline hydrochloride (Reference Example D-1; 198 mg, 0.72 mmol) was added. The resulting suspension was treated with methanol until all the solid dissolved. The reaction mixture was heated at 100° C. for 12 hours and allowed to cool to ambient temperature. The reaction mixture was then basified to pH 9–10 using methanolic ammonia and evaporated onto silica (5 ml). The residue was purified by column chromatography eluting with methanol (15%): DCM:aqueous ammonia(1%). The resulting gum was recrystallized from acetonitrile to give the title product as a solid (124 mg, 41%). NMR (300 MHz): 2.18 (s, 6H), 2.34 (m, 2H), 3.78 (m, 1H), 3.88 (m, 2H), 4.75 (brd, 1H), 6.18 (d, 1H), 6.75 (d, 2H), 7.03 (t, 1H), 7.32 (t, 1H), 7.48 (d, 2H), 7.88 (dd, 1H), 7.95 (d, 1H), 8.88 (s, 1H), 8.95(s, 1H); m/z: ($ES^+$) 416.4 ($MH^+$).

Reference Example A-2

2-Chloro-4-(2,4-difluoroanilino)pyrimidine 2,4-Dichloropyrimidine (200 mg, 1.34 mmol), 2,4-difluoroaniline (173 mg, 1.34 mmol) and diisopropylethylamine (0.26 ml, 1.48 mmol) were dissolved in n-butanol (5 ml). The reaction mixture was heated at reflux for 12 hours, cooled and evaporated onto silica (5 ml). The residue was purified by column chromatography and eluted with EtOAc (30%): isohexane to give the title product as a solid on evaporation (174 mg, 54%). NMR (300 MHz): 6.70 (d, 1H), 7.12 (t, 1H), 7.38 (t, 1H), 7.70 (dd, 1H), 8.14 (d, 1H), 9.74 (brs, 1H); m/z: (ES$^+$) 242.1 (MH$^+$).

Method B: Formation of 4-(nitrophenoxy)epoxyalkyls

Reference Example B-1

1-(4-Nitrophenoxy)-2,3-epoxypropane 1-(4-Nitrophenoxy)-2,3-epoxypropane was prepared by an analogous method to that described by Zhen-Zhong Lui et. al. in Synthetic Communications (1994), 24, 833–838.

4-Nitrophenol (4.0 g), anhydrous potassium carbonate (8.0 g) and tetrabutylammonium bromide (0.4 g) were mixed with epibromohydrin (10 ml). The reaction mixture was heated at 100° C. for 1 hour. After cooling to ambient temperature, the reaction mixture was diluted with EtOAc and filtered. The filtrate was evaporated to dryness and the residue was co-distilled twice with toluene. The resulting oil was purified by column chromatography and eluted with EtOH (1.0%):DCM to give the title product on evaporation as an oil that crystallised (4.36 g, 77.7%). NMR (CDCl$_3$, 300 MHz): 2.78 (m, 1H), 2.95 (m, 1H), 3.38 (m, 1H), 4.02 (dd, 1H), 4.38 (dd, 1H), 7.00 (d, 2H), 8.20 (d, 2H); m/z: (ES$^+$) 196 (MH$^+$).

Method C: Epoxide Opening Reactions

Reference Example C-1

3-(N,N-Dimethyl)amino-2-hydroxy-1-(4-nitrophenoxy)propane 1-(4-Nitrophenoxy)-2,3-epoxypropane (Reference Example B-1, 4.3 g) was dissolved in methanol (30 ml) and DMF (10 ml). Dimethylamine (2M solution in methanol, 17 ml) was added and the mixture was stirred at ambient temperature overnight. The reaction mixture was evaporated to dryness and the residue was dissolved in saturated sodium bicarbonate solution and EtOAc. The EtOAc layer was separated and Washed twice with saturated brine, dried over anhydrous sodium sulphate, filtered and evaporated to give the title product as an oil that slowly crystallised under high vacuum (4.79 g, 89.9%). NMR (CDCl$_3$, 300 MHz): 2.33 (s, 6H), 2.98 (m, 1H), 2.54 (m, 1H), 4.00 (m, 3 H), 7.00 (d, 2H), 8.20 (d, 2H); m/z: (ES$^+$) 241 (MH$^+$).

Method D: Reduction of aromatic nitro moiety

Reference Example D-1

4-[3-(N,N-Dimethyl)amino-2-hydroxypropoxy]aniline 3-(N,N-Dimethyl)amino-2-hydroxy-3-(4-nitrophenoxy)propane (Reference Example C-1, 3.75 g) was dissolved in EtOH (40 ml). Under an atmosphere of nitrogen, 10% palladium-on-carbon (0.4 g) was added. The nitrogen atmosphere was replaced by one of hydrogen and the reaction mixture was stirred overnight. The catalyst was removed by filtration through diatomaceous earth and the filtrate was evaporated to dryness. The residue was dissolved in diethyl ether containing a small amount of isopropanol and hydrogen chloride solution (1M in ether, 16 ml) was added. The ether was evaporated and the solid residue was suspended in isopropanol. This mixture was heated on a steam bath for several minutes then allowed to cool to ambient temperature. The resulting powder was collected by filtration, washed with isopropanol, ether and dried to give the title product (3.04 g, 72.4%). NMR (300 MHz): 2.80 (s, 6H), 3.15 (m, 2H), 3.88 (m, 2H), 4.25 (m, 1H), 5.93 (br S, 1H), 6.88 (m, 4H); m/z: (ES$^+$) 211 (MH$^+$); EA: C$_{11}$H$_{18}$N$_2$O$_2$.1.6 HCl requires C; 49.2, H; 7.4, N; 10.4, Cl; 21.7%: found: C; 49.2, H; 7.2, N; 10.1; Cl; 19.1%.

Examples 3–11

Examples 3–11 of Formula (S1-2) were prepared by the method of Example 2 according to Scheme 1 below. They were prepared using 4-[3-(N,N-dimethyl)amino-2-hydroxypropoxy]aniline (Reference Example D-1) and the appropriate 2-chloro-4-anilinopyrimidine of Formula (S1-1). These 2-chloro-4anilinopyrimidines starting materials of Formula (S1-1) are either commercially available or are readily prepared by standard methods from known materials (by analogy to Method A and the corresponding Reference Examples A-1–A-10).

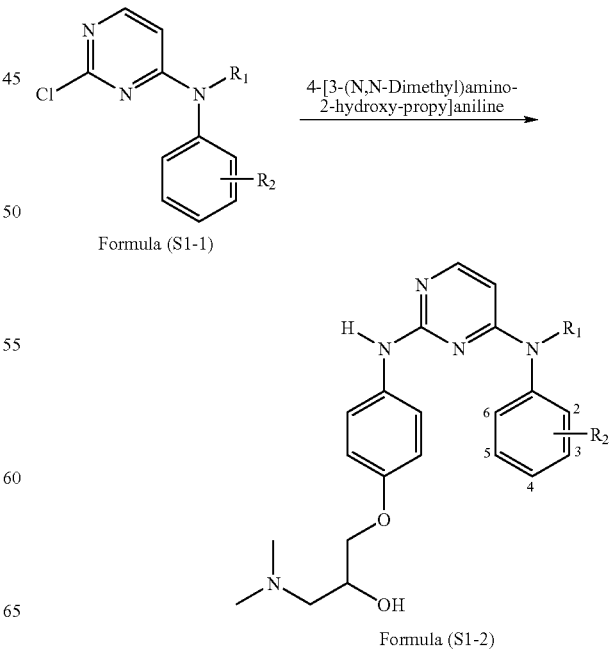

Scheme 1

| Ex No | R₁ | R₂ | NMR(300 MHz) | m/z (MH⁺) |
|---|---|---|---|---|
| 3 | H | 2-Br-4-CH$_3$ | 2.20(s, 6H), 2.38(m, 5H), 3.77(m, 1H), 3.88 (m, 2H), 4.79(s, 1H), 6.09(d, 1H), 6.7(d, 2H), 7.19(d, 1H), 7.49(m, 4H), 7.93(d, 1H), 8.67 (s, 1H), 8.80(s, 1H). | 472.4 |
| 4 | H | 2-CH$_3$-5-F | 2.19(s, 3H), 2.40(s, 6H), 2.66(m, 2H), 3.82 (m, 2H), 3.99(m, 1H), 6.20(d, 1H), 6.74(d, 2H), 6.88(t, 1H), 7.22(t, 1H), 7.52(d, 2H), 7.56(dd, 1H), 7.97(d, 1H), 8.59(s, 1H), 8.90 (s, 1H). | 412.4 |
| 5 | CH$_2$CH$_2$OH | 2-CH$_3$ | (373 K): 2.09(s, 3H), 2.20(s, 6H), 2.38(m, 2H), 3.66(m, 2H), 3.89(m, 5H), 4.30(s, 2H), 5.43(d, 1H), 6.78(d, 2H), 7.30(m, 4H), 7.50 (d, 2H), 7.79(d, 1H), 8.41(s, 1H). | 438.5 |
| 6 | H | 4-Cl | 2.19(s, 6H), 2.33(m, 2H), 3.86(m, 3H), 4.76 (d, 1H), 6.14(d, 1H), 6.85(d, 2H), 7.29(d, 2H), 7.54(d, 2H), 7.73(d, 2H), 7.98(d, 1H), 8.94(s, 1H), 9.39(s, 1H). | 414.5 |
| 7 | H | 4-OCH$_3$ | 2.17(s, 6H), 2.32(m, 2H), 3.71(s, 3H), 3.83 (m, 3H), 4.72(d, 1H), 6.06(d, 1H). 6.80(d, 2H), 6.87(d, 2H), 7.55(t, 4H), 7.89(d, 1H), 8.81(s, 1H), 9.03(s, 1H). | 410.5 |
| 8 | H | 4-CH$_3$ | 2.18(s, 6H), 2.24(s, 3H), 2.33(m, 2H), 3.83 (m, 3H), 4.74(d, 1H), 6.10(d, 1H), 6.81(d, 2H), 7.08(d, 2H), 7.55(t, 4H), 7.92(d, 1H), 8.84(s, 1H), 9.12(s, 1H). | 394.5 |
| 9 | H | 3,4-diCl | 2.18(s, 6H), 2.32(m, 2H), 3.85(m, 3H), 4.75 (d, 1H), 6.15(d, 1H), 6.85(d, 2H), 7.50(m, 4H), 8.00(d, 1H), 8.11(d, 1H), 9.02(s, 1H), 9.53(s, 1H). | 448.4 |
| 10 | H | 3-Cl | 2.16(s, 6H), 2.31(m, 2H), 3.83(m, 3H), 4.73 (d, 1H), 6.15(d, 1H), 6.83(d, 2H), 6.99(d, 1H), 7.28(t, 1H), 7.52(d, 3H), 7.89(s, 1H), 7.99(d, 1H), 8.99(s, 1H), 9.42(s, 1H). | 414.4 |
| 11 | H | 2,5-diCl | 2.17(s, 6H), 2.30(m, 2H), 3.76(m, 1H), 3.86 (m, 2H), 4.72(d, 1H), 6.35(d, 1H), 6.77(d, 2H), 7.19(dd, 1H), 7.47(d, 2H), 7.52(d, 1H), 8.01(d, 2H), 8.88(s, 1H), 8.99(s, 1H). | 448.4 |

Example 12

2-{4-[3-(N,N-Dimethyl)amino-2-hydroxypropoxy]anilino}-4-(N-(n-butyl)anilino)pyrimidine 2-Chloro-4-(N-(n-butyl)anilino)pyrimidine (570 mg, 2.18 mmol) was dissolved in n-butanol (4 ml) and 4-[3-(N,N-dimethyl)amino-2-hydroxypropoxy]aniline dihydrochloride (Reference Example D-1; 554 mg, 1.97 mmol) was added. The resulting suspension was treated with methanol until all the solid dissolved. The reaction mixture was heated at 95° C. for 12 hours and allowed to cool to ambient temperature. The reaction mixture was then basified to pH 9–10 using methanolic ammonia and then evaporated onto silica (5 ml). The residue was purified by column chromatography eluting with methanol (15%):DCM:aqueous ammonia (1%). The resulting gum was re-evaporated from EtOAc twice to give the title product as a foam (130 mg).

NMR: (353K, 400 MHz) 0.86 (t, 3H), 1.31 (m, 2H), 1.59 (m, 2H), 2.88 (s, 6H), 3.22 (m, 1H), 3.32 (dd, 1H), 3.94 (m, 2H), 4.00 (m, 2H), 4.34 (m, 1H), 5.85 (d, 1H), 6.98 (d, 2H), 7.38 (d, 2H), 7.49 (m, 3H), 7.58 (m, 2H), 7.89 (d, 1H), 10.47 (s, 1H); M.S.: (ES⁺) 436.5 (MH⁺).

Example 13

2-{4-[3-(N,N-Dimethyl)amino-2-hydroxypropoxy]anilino}-4-(N-(carbamoylmethyl)anilino)pyrimidine 2-Chloro-4-(N-(carbamoylmethyl)anilino)pyrimidine (prepared by analogy to Method A and the corresponding Reference Examples A-1–A-10) (390 mg, 1.49 mmol) was dissolved in NMP (3 ml) and 4-[3-(N,N-dimethyl)amino-2-hydroxypropoxy]aniline dihydrochloride (Reference Example D-1; 378 mg, 1.34 mmol) was added. The resulting suspension was heated at 120° C. which caused the solid to dissolve. The reaction mixture was heated at 120° C. for 12 hours and allowed to cool to ambient temperature. The reaction mixture was then basified to pH 9–10 using methanolic ammonia and then evaporated onto silica (5 ml). The residue was purified by column chromatography eluting with methanol (15%):DCM:aqueous ammonia (1%). The resulting gum was re-evaporated from EtOAc three times to give the title product as a foam (184 mg). NMR: (300 MHz) 2.31 (s, 6H), 2.49 (m, 2H), 3.8 (m, 1H), 3.92 (m, 2H), 4.42 (s, 2H), 5.68 (d, 1H), 6.79 (d, 2H), 7.4 (m, 5H), 7.58 (d, 2H), 7.82 (d, 1H), 8.93 (s, 1H); m/z: (ES⁺) 437.5 (MH⁺).

Examples 14–46

Examples 14–45 of Formula (S1-2) were prepared by the method of Example 12, and Example 46 by the method of Example 13, according to Scheme 1, using 4-[3-(N,N-dimethyl)amino-2-hydroxypropoxy]aniline (Reference Example D-1) and the appropriate 2-chloro-4-(N-alkylated)anilinopyrimidine intermediate of Formula (S1-1), (or, for Example 18, 2-chloro-4-[indan-5-yl(N-cyanomethyl)amino]pyrimidine). These 2-chloro-4-(N-alkylated)anilinopyrimidine intermediates of Formula (S1-1) were prepared according to Scheme 2 by analogy to Method E described below, using the appropriate 2-chloro-4-anilinopyrimidine intermediate (prepared by analogy to Method A and the corresponding Reference Examples A-1–A-10) and the appropriate alkylating agent.

For Example 18, the appropriate intermediate was prepared by analogy with Example 70, followed by N-alkylation with Cl—CH$_2$—CN.

| Ex No | R₁ | R₂ | NMR 300 MHz | m/z (MH⁺) |
|---|---|---|---|---|
| 14 | CH₂-cyclopropyl | H | 0.02 (m, 2H), 0.31 (m, 2H), 0.99 (m, 1H), 2.71 (s, 6H), 3.12 (m, 2H), 3.71 (d, 2H), 3.81 (m, 2H), 4.18 (m, 1H), 5.48 (d, 1H), 5.81 (d, 1H), 6.75 (d, 2H), 7.28 (m, 3H), 7.41 (m, 2H), 7.51 (d, 2H), 7.70 (d, 1H), 8.86 (s, 1H). | 434.5 |
| 15 | CH₂-phenyl | H | 2.72 (s, 6H), 3.08 (m, 2H), 3.86 (d, 2H), 4.17 (m, 1H), 5.19 (s, 2H), 5.72 (d, 2H), 6.71 (d, 2H), 7.28 (m, 8H), 7.44 (m, 4H), 7.86 (d, 1H), 8.98 (s, 1H). | 470.5 |
| 16 | (CH₂)₃CN | H | 2.82 (s, 6H), 2.89 (m, 2H), 3.21 (m, 2H), 3.91 (m, 2H), 4.14 (t, 2H), 4.28 (m, 1H), 5.66 (d, 1H), 5.97 (d, 1H), 6.90 (d, 2H), 7.37 (d, 2H), 7.42 (m, 1H), 7.54 (m, 4H), 7.86 (d, 1H), 9.47 (brs, 1H). | 433.5 |
| 17 | CH₂CN | H | 2.21 (s, 6H), 2.36 (m, 2H), 3.80 (m, 1H), 3.90 (m, 2H), 4.86 (brs, 1H), 4.95 (s, 2H), 5.71 (d, 1H), 6.83 (d, 2H), 7.38 (d, 2H), 7.44 (m, 1H), 7.58 (m, 4H), 7.96 (d, 1H), 9.23 (s, 1H). | 419.5 |
| 18 | CH₂CN | cyclopentyl So that Q2 is (indanyl) | 2.8 (m, 2H), 2.82 (brs, 6H), 2.91 (t, 4H), 3.22 (m, 2H), 3.92 (m, 2H), 4.25 (m, 1H), 4.89 (s, 2H), 5.69 (d, 1H), 5.93 (d, 1H), 6.88 (d, 2H), 7.09 (dd, 1H), 7.20 (s, 1H), 7.38 (d, 1H), 7.63 (d, 2H), 7.92 (d, 1H), 9.27 (s, 1H). | 459.5 |
| 19 | CH₂CN | 4-Cl | 2.62 (s, 6H), 2.95 (m, 2H), 3.89 (d, 2H), 4.13 (m, 1H), 4.93 (s, 2H), 5.79 (d, 1H), 6.84 (d, 2H), 7.40 (d, 2H), 7.60 (m, 4H), 7.98 (d, 1H), 9.22 (s, 1H). | 453.4 |
| 20 | CH₂CN | 2,4-diF | 2.62 (s, 6H), 2.95 (m, 2H), 3.88 (d, 2H), 4.13 (m, 1H), 4.91 (s, 2H), 5.79 (brd, 1H), 6.83 (d, 2H), 7.28 (t, 1H), 7.54 (m, 4H), 8.01 (d, 1H), 9.23 (s, 1H). | 455.5 |
| 21 | CH₂CN | 3,4-diCl | 2.60 (s, 6H), 2.92 (m, 2H), 3.89 (d, 2H), 4.12 (m, 1H), 4.97 (s, 2H), 5.92 (d, 1H), 6.83 (d, 2H), 7.40 (dd, 1H), 7.57 (d, 2H), 7.73 (s, 1H), 7.80 (d, 1H), 8.01 (d, 1H), 9.24 (s, 1H). | 487.4 |
| 22 | CH₂CH₂F | H | 2.88 (s, 6H), 3.22 (m, 1H), 3.31 (dd, 1H), 4.00 (m, 2H), 4.26 (m, 2H), 4.32 (m, 1H), 4.62 (m, 1H), 4.73 (m, 1H), 5.81 (d, 1H), 6.93 (d, 2H), 7.38 (d, 2H), 7.49 (m, 3H), 7.56 (m, 2H), 7.89 (d, 1H), 9.78 (brs, 1H). | 426.5 |
| 23 | CH₂C≡CH | H | 2.88 (s, 6H), 3.22 (m, 2H), 3.33 (dd, 1H), 4.01 (m, 2H), 4.33 (m, 1H), 4.76 (s, 2H), 5.93 (d, 1H), 6.97 (d, 2H), 7.42 (d, 2H), 7.55 (m, 5H), 7.96 (d, 1H), 10.33 (s, 1H). | 418.4 |
| 24 | CH₂CN | 2-Br-4-CH₃ | 2.41 (s, 3H), 2.74 (s, 6H), 3.08 (m, 2H), 3.98 (m, 2H), 4.22 (m, 1H), 4.86 (brs, 2H), 5.57 (d, 1H), 6.89 (d, 2H), 7.39 (s, 2H), 7.61 (d, 1H), 7.69 (s, 1H), 7.98 (d, 1H), 8.81 (brs, 1H). | 511.5 |
| 25 | CH₂CN | 2-Cl-5-CH₃ | 2.39 (s, 3H), 2.76 (s, 6H), 3.06 (m, 1H), 3.17 (dd, 1H), 3.97 (m, 2H), 4.23 (m, 1H), 4.88 (s, 2H), 5.61 (d, 1H), 6.90 (d, 2H), 7.34 (m, 2H), 7.56 (d, 1H), 7.61 (d, 2H), 8.00 (d, 1H), 8.80 (s, 1H). | 467.5 |

| Ex No | R₁ | R₂ | NMR 300 MHz | m/z (MH⁺) |
|---|---|---|---|---|
| 26 | n-butyl branched | 2,5-diCl | 0.89 (t, 3H), 1.36 (m, 2H), 1.63 (m, 2H), 2.89 (s, 6H), 3.21 (m, 1H), 3.32 (dd, 1H), 3.85 (m, 2H), 4.00 (m, 2H), 4.34 (m, 1H), 5.96 (brs, 1H), 6.89 (d, 2H), 7.40 (d, 2H), 7.60 (dd, 1H), 7.62 (s, 1H), 7.71 (d, 1H), 8.00 (d, 1H), 9.91 (brs, 1H). | 504.5 |
| 27 | -CH₂CH₂F branched | 2,5-diCl | 2.88 (s, 6H), 3.21 (m, 1H), 3.31 (dd, 1H), 3.99 (m, 2H), 4.19 (brd, 2H), 4.33 (m, 1H), 4.62 (m, 1H), 4.73 (m, 1H), 5.93 (brs, 1H), 6.88 (d, 2H), 7.42 (d, 2H), 7.58 (dd, 1H), 7.63 (s, 1H), 7.71 (d, 1H), 8.00 (d, 1H), 9.62 (brs, 1H). | 494.4 |
| 28 | cyclopropylmethyl branched | 2,5-diCl | 0.00 (m, 2H), 0.31 (m, 2H), 0.89 (m, 1H), 2.71 (s, 6H), 3.06 (m, 1H), 3.17 (dd, 1H), 3.63 (brd, 2H), 3.83 (m, 2H), 4.18 (m, 1H), 5.80 (brs, 1H), 6.74 (d, 2H), 7.22 (d, 2H), 7.43 (dd, 1H), 7.49 (s, 1H), 7.55 (d, 1H), 7.83 (d, 1H), 9.81 (brs, 1H). | 502.4 |
| 29 | propargyl branched | 2,5-diCl | 2.70 (s, 6H), 2.98 (s, 1H), 3.04 (m, 1H), 3.17 (dd, 1H), 3.84 (m, 2H), 4.17 (m, 1H), 4.54 (s, 2H), 5.79 (d, 1H), 6.71 (d, 2H), 7.29 (d, 2H), 7.43 (dd, 1H), 7.46 (s, 1H), 7.56 (d, 1H), 7.89 (d, 1H), 9.50 (brs, 1H). | 486.4 |
| 30 | -(CH₂)₃CN branched | 2,5-diCl | 2.86 (s, 6H), 2.96 (m, 2H), 3.19 (m, 1H), 3.29 (dd, 1H), 3.98 (m, 2H), 4.09 (m, 2H), 4.28 (m, 1H), 5.66 (d, 1H), 6.87 (d, 2H), 7.54 (d, 2H), 7.58 (dd, 1H), 7.66 (s, 1H), 7.70 (d, 1H), 7.98 (d, 1H), 8.73 (s, 1H). | 504.1 |
| 31 | benzyl branched | 2,5-diCl | 2.79 (S, 6H), 3.13 (m, 1H), 3.24 (dd, 1H), 3.90 (m, 2H), 4.24 (m, 1H), 5.06 (brs, 2H), 5.90 (brd, 1H), 6.78 (d, 2H), 7.23 (m, 5H), 7.31 (m, 3H), 7.44 (dd, 1H), 7.58 (d, 1H), 7.97 (d, 1H), 9.69 (brs, 1H). | 538.5 |
| 32 | -CH₂CN branched | 2,5-diCl | 2.79 (s, 6H), 3.09 (m, 1H), 3.20 (dd, 1H), 3.98 (m, 2H), 4.25 (m, 1H), 4.91 (s, 2H), 5.74 (d, 1H), 6.88 (d, 2H), 7.58 (d, 2H), 7.60 (dd, 1H), 7.63 (s, 1H), 7.73 (d, 1H), 8.04 (d, 1H), 8.85 (brs, 1H). | 487.4 |
| 33 | isobutyl branched | 2,5-diCl | 0.89 (d, 6H), 1.53 (m, 2H), 1.62 (m, 1H), 2.89 (s, 6H), 3.23 (m, 1H), 3.34 (dd, 1H), 3.87 (m, 2H), 4.00 (m, 2H), 4.34 (m, 1H), 5.88 (d, 1H), 6.89 (d, 2H), 7.40 (d, 2H), 7.59 (dd, 1H), 7.62 (s, 1H), 7.71 (d, 1H), 7.99 (d, 1H), 9.75 (brs, 1H). | 518.5 |
| 34 | n-propyl branched | 2,5-diCl | 0.93 (t, 3H), 1.68 (m, 2H), 2.89 (s, 6H), 3.21 (m, 1H), 3.32 (dd, 1H), 3.81 (m, 2H), 4.00 (m, 2H), 4.33 (m, 1H), 5.96 (d, 1H), 6.88 (d, 2H), 7.39 (d, 2H), 7.59 (dd, 1H), 7.61 (s, 1H), 7.70 (d, 1H), 7.99 (d, 1H), 9.89 (brs, 1H). | 490.4 |
| 35 | phthalimidopropyl branched | 2,5-diCl | 1.85 (m, 2H), 2.72 (s, 6H), 3.06 (m, 1H), 3.18 (dd, 1H), 3.52 (t, 2H), 3.80 (m, 2H), 3.86 (m, 2H), 4.18 (m, 1H), 5.73 (brd, 1H), 6.73 (d, 2H), 7.27 (d, 2H), 7.39 (dd, 1H), 7.48 (s, 1H), 7.50 (d, 1H), 7.68 (s, 4H), 7.83 (d, 1H), 9.39 (brs, 1H). | 635.5 |
| 36 | -CH₂CH(OH)CF₂ branched | 2,5-diCl | 2.86 (s, 6H), 3.19 (m, 1H), 3.30 (dd, 1H), 3.98 (m, 2H), 4.30 (m, 2H), 4.48 (m, 1H), 5.63 (d, 1H), 6.83 (d, 2H), 7.51 (m, 3H), 7.67 (d, 1H), 7.69 (s, 1H), 7.95 (d, 1H), 8.72 (brs, 1H). | 560.4 |

| Ex No | R₁ | R₂ | NMR 300 MHz | m/z (MH⁺) |
|---|---|---|---|---|
| 37 | CH₂-CH(F)-CH₂F group | 2,5-diCl | 2.89 (s, 6H), 3.21 (m, 1H), 3.32 (dd, 1H), 3.97 (m, 2H), 4.29 (m, 3H), 5.79 (s, 1H), 6.34 (brt, 1H), 6.88 (d, 2H), 7.48 (d, 2H), 7.59 (d, 1H), 7.62 (s, 1H), 7.70 (d, 1H), 8.00 (d, 1H), 9.28 (brs, 1H). | 512.4 |
| 38 | CH₂-CH=CH-Br group | 2,5-diCl | 2.78 (s, 6H), 3.08 (m, 1H), 3.19 (dd, 1H), 3.95 (m, 2H), 4.24 (m, 1H), 4.52 (brdd, 2H), 5.70 (d, 1H), 6.48 (m, 1H), 6.59 (d, 1H), 6.82 (d, 2H), 7.52 (m, 4H), 7.68 (d, 1H), 7.97 (d, 1H), 8.66 (brs, 1H). | 566.4 |
| 39 | CH₂CH₂-C(F)=CF₂ group | 2,5-diCl | 2.79 (m, 2H), 2.89 (s, 6H), 3.21 (m, 1H), 3.30 (dd, 1H), 3.98 (m, 2H), 4.09 (m, 2H), 4.31 (m, 1H), 5.86 (brs, 1H), 6.89 (d, 2H), 7.42 (d, 2H), 7.62 (m, 2H), 7.72 (d, 1H), 8.00 (d, 1H), 9.72 (brs, 1H). | 556.4 |
| 40 | CH₂CH₂-CF₃ group | 2,5-diCl | 2.72 (m, 2H), 2.86 (s, 6H), 3.19 (m, 1H), 3.30 (dd, 1H), 3.98 (m, 2H), 4.07 (m, 2H), 4.29 (m, 1H), 5.60 (d, 1H), 6.86 (d, 2H), 7.55 (m, 3H), 7.66 (s, 1H), 7.70 (d, 1H), 7.95 (d, 1H), 8.72 (brs, 1H). | 544.4 |
| 41 | CH₂CH₂CH₂-CF₃ group | 2,5-diCl | 1.87 (m, 2H), 2.31 (m, 2H), 2.87 (s, 6H), 3.21 (m, 1H), 3.31 (dd, 1H), 3.96 (m, 2H), 4.07 (m, 2H), 4.32 (m, 1H), 5.94 (brs, 1H), 6.88 (d, 2H), 7.39 (d, 2H), 7.60 (d, 1H), 7.71 (m, 2H), 8.00 (d, 1H). 9.80 (brs, 1H). | 558.4 |
| 42 | CH₂-CH=CH-Ph group | 2,5-diCl | 2.85 (s, 6H), 3.17 (m, 1H), 3.29 (dd, 1H), 3.95 (m, 2H), 4.29 (m, 1H), 4.62 (d, 2H), 5.86 (d, 1H), 6.35 (m, 1H), 6.59 (d, 1H), 6.80 (d, 2H), 7.30 (m, 5H), 7.45 (d, 2H), 7.51 (dd, 1H), 7.60 (s, 1H), 7.6 (d, 1H), 7.98 (d, 1H), 9.08 (brs, 1H). | 564.4 |
| 43 | n-hexyl group | 2,5-diCl | 0.86 (t, 3H), 1.28 (m, 6H), 1.60 (m, 2H), 2.85 (s, 6H), 3.19 (m, 1H), 3.30 (dd, 1H), 3.83 (m, 2H), 3.98 (m, 2H), 4.32 (m, 1H), 5.98 (brs, 1H), 6.87 (d, 2H), 7.37 (d, 2H), 7.58 (dd, 1H), 7.60 (s, 1H), 7.69 (d, 1H), 7.99 (d, 1H), 10.12 (brs, 1H). | 532.5 |
| 44 | CH₂CH₂-S-Ph group | 2,5-diCl | 2.80 (s, 6H), 3.10 (m, 1H), 3.20 (dd, 1H), 3.31 (t, 2H), 3.94 (m, 2H), 4.00 (m, 2H), 4.27 (m, 1H), 5.62 (d, 1H), 6.82 (d, 2H), 7.20 (m, 1H), 7.30 (m, 4H), 7.50 (d, 2H), 7.52 (dd, 1H), 7.62 (s, 1H), 7.67 (d, 1H), 7.94 (d, 1H), 8.59 (s, 1H). | 584.4 |
| 45 | CH₂-(2-CN-phenyl) group | 2,5-diCl | 2.88 (s, 6H), 3.20 (m, 1H), 3.30 (dd, 1H), 3.99 (m, 2H), 4.33 (m, 1H), 5.31 (s, 2H), 5.95 (d, 1H), 6.86 (d, 2H), 7.38 (d, 2H), 7.51 (m, 3H), 7.66 (m, 3H), 7.78 (d, 1H), 8.05 (d, 1H), 9.79 (brs, 1H). | 563.4 |
| 46 | CH₂-C(=O)-NH₂ group | 2,5-diCl | 2.99 (s, 6H), 3.32 (m, 1H), 3.45 (dd, 1H), 4.10 (m, 2H), 4.47 (m, 2H), 4.54 (m, 1H), 5.87 (d, 1H), 6.98 (d, 2H), 7.22 (brs, 2H), 7.60 (d, 2H), 7.67 (dd, 1H), 7.79 (d, 1H), 7.90 (s, 1H), 8.09 (d, 1H), 9.04 (brs, 1H). | 505.5 |

Preparation of Starting Materials for Examples 12–46

The appropriate 2-chloro-4-(N-alkylated)anilinopyrimidine intermediates of Formula (S1-1) for Examples 12–17 and 19–46 above are either commercially available or are readily prepared by standard methods from known materials, according to Scheme 2. For example, the following reactions (Methods A and E) are illustrations, but not limitations, of the preparation of some of the starting materials used in the above Examples.

49

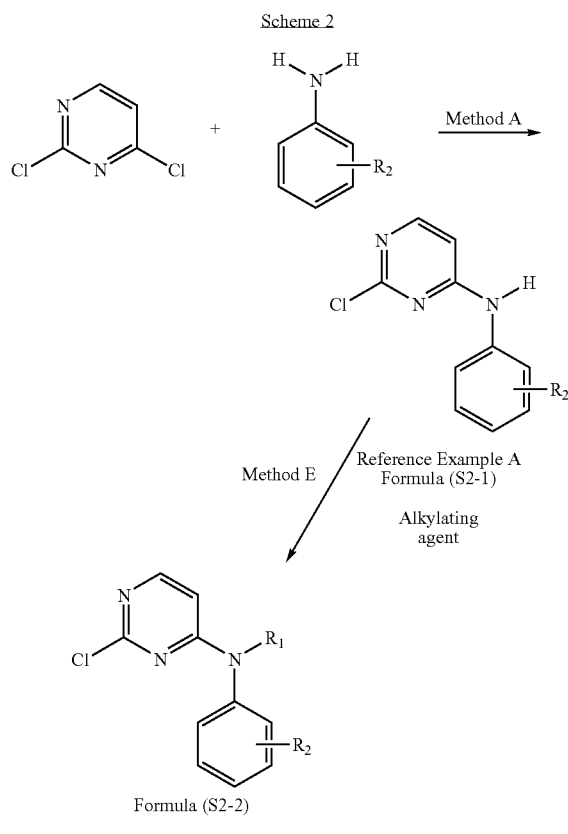

Reference Example A-3

2-Chloro-4-(2-bromo-4-methylanilino)pyrimidine 2,4-Dichloropyrimidine (1 g, 6.71 mmol), 2-bromo-4-methylaniline (1.25 g, 6.71 mmol) and di-isopropylethylamine (1.29 ml, 7.38 mmol) were dissolved in n-butanol (5 ml). The reaction mixture was heated at 120° C. for 12 hours, cooled and evaporated onto silica (5 ml). The residue was purified by column chromatography and eluted with EtOAc (30%):isohexane to give the title product as a solid on evaporation (1.01 g). NMR (300 MHz): 2.31 (s, 3H), 6.50 (d, 1H), 7.22 (dd, 1H), 7.36 (d, 1H), 7.55 (s, 1H), 8.09 (d, 1H), 9.61 (s, 1H); m/z: (ES$^+$) 298.1 (MH$^+$).

Reference Example A-4

2-Chloro-4-(2,5-dichloroanilino)pyrimidine 2,4-Dichloropyrimidine (50 g, 0.34 mol), 2,5-dichloroaniline (54.38 g, 0.34 mol) and concentrated hydrochloric acid (cat. amount) were dissolved in n-butanol (250 ml). The reaction mixture was stirred at room temperature for 12 hours after which the solid that had formed was collected by filtration. The organics were allowed to stand for 48 hours and the solid that formed was collected by filtration, washed with EtOAc and dried to give the title product as a white solid (18.65 g). NMR (300 MHz): 6.82 (d, 1H), 7.31 (dd, 1H), 7.58 (d, 1H), 7.82 (s, 1H), 8.19 (d, 1H), 9.82 (s, 1H); m/z: (ES$^+$) 273.9 (MH$^+$).

50

Method E: N-alkylation of 2-chloro-4-anilinopyrimidines

A suitable alkylating agent (commercially available) is of the formula R$_1$—X where X is a leaving group, such as chloro or bromo.

Reference Example E-1

2-Chloro-4-(N-cyanomethyl-2-bromo-4-methylanilino)pyrimidine

2-Chloro-4-(2-bromo-4-methylanilino)pyrimidine (500 mg, 1.68 mmol), chloroacetonitrile (0.13 ml, 2.02 mmol) and potassium carbonate (279 mg, 2.02 mmol) were dissolved in DMF (3 ml). The reaction mixture was stirred at room temperature for 12 hours. Chloroacetonitrile (0.13 ml, 2.02 mmol) and potassium carbonate (279 mg, 2.02 mmol) were again added, and the reaction mixture was stirred at room temperature for a further 48 hours. The reaction mixture was evaporated onto silica (5 ml) and purified by column chromatography eluting with EtOAc (0–40%):isohexane to give the title product as a solid on evaporation (537 mg). NMR (300 MHz): 2.38 (s, 3H), 4.82 (d, 1H), 4.99 (d, 1H), 6.09 (brs, 1H), 7.41 (m, 2H), 7.71 (s, 1H), 8.16 (brd, 1H); M.S. (ES$^+$) 337.2 (MH$^+$).

For Example 18, 2-chloro-4-[indan-5-yl(N-cyanomethyl)amino]pyrimidine) was prepared by reaction of 2,4-dichloropyrimidine with 5-aminoindane by analogy with Method A above, followed by N-alkylation using chloroacetonitrile (by analogy with Reference Example E-1 above).

Example 47

2-{4-[3-(N,N-Dimethyl)amino-2-hydroxypropoxy]anilino}-4-(2-ethylanilino)pyrimidine 2-Chloro-4-(2-ethylanilino)pyrimidine (Reference Example A-5; 210 mg, 0.90 mmol) was dissolved in n-butanol (20 ml). To this solution was added a hot solution of 4-[3-(N,N-dimethyl)amino-2-hydroxypropoxy]aniline hydrochloride (Reference Example D-1; 229 mg, 0.81 mmol) in methanol (2 ml). The reaction mixture was heated at 100° C. for 18 hours, allowed to cool to ambient temperature and then evaporated onto silica (3 ml). The residue was purified by column chromatography eluting with 0–5% 2.0M methanolic ammonia solution in DCM to give the title product as a colourless solid (201 mg, 61%). NMR (300 MHz): 1.09 (t, 3H), 2.17 (s, 6H), 2.31 (m, 2H), 2.58 (q, 2H), 3.80 (m, 3H), 5.96 (d, 1H), 6.72 (d, 2H), 7.20 (m, 3H), 7.36 (d, 1H), 7.53 (d, 2H), 7.89 (d, 1H), 8.56 (s, 1H), 8.76 (s, 1H); m/z: (ES$^+$) 408.3 (MH$^+$)

Examples 48–66

Examples 48–66 of Formula (S1-2) wherein R$_1$ is hydrogen, were prepared by the method of Example 47 according to Scheme 1, using 4-[3-(N,N-dimethyl)amino-2-hydroxypropoxy]aniline (Reference Example D-1) and the appropriate 2-chloro-4-anilinopyrimidine of Formula (S1-1) wherein R$_1$ is hydrogen. The appropriate 2-chloro-4-anilinopyrimidine starting materials of Formula (S1-1) wherein R$_1$ is hydrogen are either commercially available or are readily prepared by standard methods from known materials (by analogy to Method A and the corresponding Reference Examples A-1–A-10).

| Ex No | R₂ | NMR(300 MHz) | m/z (MH⁻) |
|---|---|---|---|
| 48 | 2-(CH$_2$)$_5$CH$_3$ | 0.77(t, 3H), 1.18(m, 6H) 1.44(m, 2H), 2.18(s, 6H), 2.30(m, 2H), 3.80(m, 3H), 5.98(d, 1H), 6.69(d, 2H), 7.20(m, 3H), 7.37(d, 1H), 7.50(d, 2H), 7.87(d, 1H), 8.57(s, 1H), 8.76(s, 1H). | 464.4 |
| 49 | 2-Cl | 2.19(s, 6H), 2.31(m, 2H), 3.75(m, 1H), 3.83(m, 2H), 6.21(d, 1H), 6.72(d, 2H), 7.18(m, 1H), 7.33(m, 1H), 7.50(m, 2H), 7.82(m, 1H), 7.96(m, 1H), 8.78(s, 1H), 8.86(s, 1H). | 414.3 |
| 50 | 2-morpholino | 2.18(s, 6H), 2.31(m, 2H), 2.81(m, 4H), 3.72(m, 4H), 3.78(m, 1H), 3.88(m, 2H), 4.85(br, 1H), 6.31(d, 1H), 6.80(d, 2H), 7.1(m, 3H), 7.58(d, 2H), 7.98(d, 2H), 8.24(s, 1H), 8.88(s, 1H). | 465.5 |
| 51 | 2-CO$_2$Me | 2.19(s, 6H), 2.31(m, 2H), 3.82(m, 6H), 4.75(br, 1H), 6.28(d, 1H), 6.82(d, 2H), 7.10(t, 1H), 7.56(d, 2H), 7.96(d, 1H), 8.04(d, 1H), 8.54(d, 1H), 9.04(s, 1H). | 438.3 |
| 52 | 2-SMe | 2.17(s, 6H), 2.31(m, 2H), 2.39(s, 3H), 3.80(m, 3H), 4.72(br, 1H), 6.02(d, 1H), 6.70(d, 2H), 7.22(m, 2H), 7.37(m, 1H), 7.49(m, 3H) 7.92(d, 1H), 8.58(s, 1H), 8.79(s, 1H). | 426.3 |
| 53 | 4-NMe$_2$ | 2.18(s, 6H), 2.32(m, 2H), 2.84(s, 6H), 3.83(m, 3H), 4.75(br, 1H), 6.01(d, 1H), 6.70(d, 2H), 6.80(d, 2H), 7.40(d, 2H), 7.59(d, 2H) 7.86(d, 1H), 8.77(s, 1H), 8.87(s, 1H). | 423.3 |
| 54 | 2-(CH$_2$)$_2$CH$_3$ | 0.82(t, 3H), 1.49(sextuplet, 2H), 2.18(s, 6H), 2.32(m, 2H), 2.58(t, 2H), 3.80(m, 3H), 4.74(br, 1H), 5.98(d, 1H), 6.68(d, 2H), 7.20(m, 3H), 7.38(d, 1H), 7.51(d, 2H) 7.88(d, 1H), 8.57(s, 1H), 8.77(s, 1H). | 422.3 |
| 55 | 4-Br | 2.18(s, 6H), 2.33(m, 2H), 3.83(m. 3H), 4.76(br, 1H), 6.17(d, 1H), 6.83(d, 2H), 7.41(d, 2H), 7.52(d, 2H), 7.68(d, 2H) 7.98(d, 1H), 8.96(s, 1H), 9.40(s, 1H). | 460.4 |
| 56 | 2-F-5-Me | 2.18(s, 6H), 2.31(m, 5H), 3.81(m, 3H), 4.74(br, 1H), 6.22(d, 1H), 6.78(d, 2H), 6.90(m, 1H), 7.12(m, 1H), 7.51(d, 2H) 7.77(d, 1H), 7.98(d, 1H), 8.88(s, 1H). | 412.4 |
| 57 | 2-I | 2.18(s, 6H), 2.31(m, 2H), 3.80(m, 3H), 4.74(br, 1H), 6.04(d, 1H), 6.67(d, 2H), 7.00(m, 1H), 7.47(m, 4H), 7.95(m, 2H), 8.72(s, 1H), 8.82(s, 1H). | 506.4 |
| 58 | 2-F-4-Me | 2.19(s, 6H), 2.31(m, 5H), 3.83(m, 3H), 4.76(br, 1H), 6.19(d, 1H), 6.77(d, 2H), 6.98(d, 1H), 7.09(d, 1H), 7.52(d, 2H) 7.78(t, 1H), 7.96(d, 1H), 8.83(s, 1H). | 412.4 |
| 59 | 4-F | 2.19(s, 6H), 2.32(m, 2H), 3.82(m, 3H), 4.77(br, 1H), 6.14(d, 1H), 6.82(d, 2H), 7.10(t, 2H), 7.57(d, 2H), 7.66(t, 2H) 7.97(d, 1H), 8.92(s, 1H), 9.25(s, 1H). | 398.4 |
| 60 | 2-CN | 2.18(s, 6H), 2.31(m, 2H), 3.81(m, 3H), 4.74(br, 1H), 6.22(d, 1H), 6.71(d, 2H), 7.32(t, 1H), 7.44(d, 2H), 7.76(m, 3H), 8.02(d, 1H), 8.96(s, 1H), 9.41(s, 1H). | 405.4 |
| 61 | 4-COMe | (MeOK-δ$_4$): 2.36(s, 6H), 2.54(m, 5H), 4.00(m, 3H), 6.20(d, 1H), 6.96(d, 2H), 7.43(d, 2H), 7.81(d, 2H), 7.89(d, 2H) 7.95(d, 1H). | 422.4 |
| 62 | 2-Br | 2.19(s, 6H), 2.31(m, 2H), 3.80(m, 3H), 4.77(br, 1H), 6.20(d, 1H), 6.76(d, 2H), 7.16(m, 1H), 7.42(m, 1H), 7.52(d, 2H) 7.74(m, 2H), 7.99(d, 1H), 8.79(s, 1H), 8.90(s, 1H). | 458.3 |
| 63 | 2-Cl-5-Me | 2.20(s, 6H), 2.29(s, 3H), 2.30(m, 1H), 2.41(dd, 1H), 3.77(m, 1H), 3.88(m, 2H), 4.79(br, 1H), 6.20(d, 1H), 6.72(d, 2H), 6.99(d, 1H), 7.37(d, 1H), 7.50(d, 2H) 7.62(s, 1H), 7.95(d, 1H), 8.72(s, 1H), 8.89(s, 1H). | 428.5 |
| 64 | 2-OEt | 1.34(t, 3H), 2.19(s, 6H), 2.34(m, 2H), 3.80(m, 1H), 3.88(m, 2H), 4.09(q, 2H), 4.78(m, 1H), 6.27(d, 1H), 6.78(d, 2H), 6.92(m, 1H), 7.05(m, 2H), 7.56(d, 2H), 7.95(m, 2H), 8.32(s, 1H), 8.88(s, 1H). | 424.5 |
| 65 | 2-F-5-CF$_3$ | 2.17(s, 6H), 2.31(m, 2H), 3.77(m, 1H), 3.83(m, 2H), 4.73(d, 1H), 6.32(d, 1H), 6.74(d, 2H), 7.45(m, 4H), 8.02(d, 1H), 8.32(m, 1H), 8.97(s, 1H), 9.12(s, 1H). | 466.5 |
| 66 | 2-OMe | 2.19(s, 6H), 2.33(m, 2H), 3.83(m, 6H), 4.77(br, 1H), 6.27(d, 1H), 6.78(d, 2H), 6.92(m, 1H), 7.02(m, 2H), 7.56(d, 2H), 7.93(d, 1H), 8.01(d, 1H), 8.42(s, 1H), 8.92(s, 1H). | 410.4 |

Preparation of Starting Materials for Examples 47–66

The 2-chloro-4-anilinopyrimidine starting materials for Examples 47–66 above are either commercially available or are readily prepared by standard methods from known materials. For example, the following reactions (Method A of Scheme 2) are illustrations, but not limitations, of the preparation of some of the starting materials used in the above Examples.

Reference Example A-5

2-Chloro-4-(2-ethylanilino)pyrimidine 2,4-Dichloropyrimidine (596 mg, 4 mmol), 2-ethylaniline (494 ml, 4 mmol) and N,N-diisopropylethylamine (695 ml, 4 mmol) were dissolved in n-butanol (20 ml) with stirring. The reaction mixture was heated to 100° C. for 18 hours, allowed to cool to ambient temperature and evaporated onto silica (3 ml). The residue was purified by column chromatography eluting with EtOAc (0–20%): isohexane to give the title product as a colourless solid on evaporation (215 mg, 23%). NMR (CDCl$_3$, 300 MHz): 1.20 (t, 3H), 2.61 (q, 2H), 6.26 (d, 1H), 6.80 (br, 1H) 7.31 (m, 4H), 8.04 (d, 1H); m/z: (ES$^-$) 234.2 (MH$^+$).

Reference Example A-6

2-Chloro-4-(2-methoxycarbonylanilino)pyrimidine 2,4-Dichloropyrimidine (596 mg, 4 mmol), methyl 2-aminobenzoate (517 ml, 4 mmol) and 2,6-lutidine (465 ml, 4 mmol) were dissolved in n-butanol (20 ml) with stirring. The reaction mixture was heated to 120° C. for 24 hours, allowed to cool to ambient temperature and evaporated onto silica (3 ml). The residue was purified by column chromatography eluting with EtOAc (0–20%): isohexane to give the title product as a colourless solid on evaporation (137 mg, 13%). NMR (CDCl$_3$, 300 MHz): 3.97 (s, 3H), 6.63 (d, 1H), 7.09 (t, 1H) 7.61 (m, 1H), 8.05 (d, 1H), 8.19 (d, 1H), 8.74 (d, 1H); m/z: (ES$^+$) 264.3 (MH$^+$).

Reference Example A-7

2-Chloro-4-(2-cyanoanilino)pyrimidine 2,4-Dichloropyrimidine (149 mg, 1 mmol), 2-cyanoaniline (118 mg, 1 mmol) and 2 drops conc. HCl were dissolved in water (20 ml). The reaction mixture was stirred at ambient temperature for 18 hours. The resulting precipitate was filtered off and dried under vacuum to give the title product as a colourless solid (84 mg, 36%). NMR (300 MHz) 6.79 (d, 1H), 7.42 (m, 1H), 7.62 (m, 1H), 7.75 (m, 1H), 7.89 (m, 1H), 8.24 (d, 1H), 10.23 (br, 1H); m/z: (ES$^+$) 231.1 (MH$^+$).

Reference Example A-8

2-Chloro-4-(2-fluoro-5-trifluoromethyl)anilinopyrimidine 2,4-Dichloropyrimidine (596 mg, 4 mmol), 2-fluoro-5-trifluoromethylaniline (520 µl, 4 mmol) and 2 drops conc. HCl were dissolved in n-butanol (20 ml) with stirring. The reaction mixture was stirred at ambient temperature for 18 hours and then evaporated onto silica (3 ml). The residue was purified by column chromatography eluting with EtOAc (5–50%): isohexane to give the title product as a colourless solid on evaporation (93 mg, 8%). NMR (CDCl$_3$, 300 MHz): 6.60 (d, 1H), 6.99 (br, 1H), 7.27 (m, 1H), 7.42 (m, 1H), 8.25 (d, 1H), 8.41 (m, 1H); m/z: (ES$^+$) 292.1 (MH$^+$).

Example 67

2-Anilino-4-{4-[3-(N,N-dimethyl)amino-2-hydroxypropoxy]anilino}pyrimidine

2-Anilino-4-chloropyrimidine (145 mg, 0.71 mmol) was dissolved in n-butanol (20 ml). To this solution was added a hot solution of 4-[3-(N,N-dimethyl)amino-2-hydroxy-propoxy]aniline hydrochloride (Reference Example D-1; 178 mg, 0.63 mmol) in methanol (2 ml). The reaction mixture was heated at 80° C. for 18 hours, allowed to cool to ambient temperature and then evaporated onto silica (3 ml). The residue was purified by column chromatography eluting with 0–8% 2.0M methanolic ammonia solution in DCM to give the title product as a colourless solid (157 mg, 65%). NMR (300 MHz): 2.18 (s, 6H), 2.33 (m, 2H), 3.83 (m, 3H), 4.77 (d, 1H), 6.11 (d, 1H), 6.86 (m, 3H), 7.19 (m, 2H), 7.51 (d, 2H), 7.69 (d, 2H), 7.96 (d, 1H), 9.01 (s, 1H), 9.08 (s, 1H); m/z: (ES$^+$) 380.4 (MH$^+$).

Method F: Conversion of 2-anilino-4-hydroxypyrimidines to 2-anilino-4-chloropyrimidines

Reference Example F-1

2-Anilino-4-chlorolpyrimidine

2-Anilino-4-hydroxypyrimidine (Reference Example G-1) (750 mg, 4.01 mmol) was dissolved in phosphorus oxychloride (5 ml). To this solution was added phosphorus pentachloride (918 mg, 4.41 mmol) and the reaction mixture heated to 110° C. for 18 hours. The reaction mixture was then allowed to cool to ambient temperature and slowly added to cool (20–30° C.) water (25 ml) with vigorous stirring. This was then left to stir for 60 mins before being extracted with EtOAc (2×15 ml). The organic layers were combined and washed with NaHCO$_3$ (aq) (2×10 ml), brine (10 ml) and then evaporated onto silica (3 ml). The residue was purified by column chromatography eluting with 0–20% EtOAc in isohexane to give the title product as a colourless solid (492 mg, 60%). NMR (CDCl$_3$, 300 MHz): 6.78 (m, 1H), 7.09 (m, 1H), 7.19 (br, 1H), 7.36 (m, 2H), 7.59 (d, 2H), 8.28 (d, 1H); m/z: (ES$^+$) 206.0 (MH$^+$).

Method G: Reaction of 2-methylthio-4-hydroxypyrimidine with an aniline

Reference Example G-1

2-Anilino-4-hydroxypyrimidine

2-Methylthio-4-hydroxypyrimidine (1.42 g, 10 mmol) was dissolved in 2-methoxyethylether (10 ml). To this solution was added aniline (910 µl, 10 mmol) and the reaction mixture heated at 160° C. for 18 hours. The resulting precipitate was filtered off and washed with diethyl ether (10 ml), water (10 ml), diethyl ether (2×10 ml) and dried under vacuum to give the title product as a colourless solid (1.296 g, 69%). NMR (300 MHz): 5.79, (d, 1H), 6.99 (t, 1H), 7.24 (m, 2H), 7.57 (m, 2H), 7.73 (m, 1H), 8.80 (br, 1H); m/z: (ES$^+$) 188.1 (MH$^+$).

Examples 68–73

Examples 68–73 of Formula (S1-2) were prepared by the method of Example 2 according to Scheme 1, using 4-[3-(N,N-dimethyl)amino-2-hydroxypropoxy]aniline (Reference Example D-1) and the appropriate 2-chloro-4-anilinopyrimidine intermediate of Formula (S1-1), 2-chloro-4-[indan-5-ylamino]pyrimidine (for Example 70) and 2-chloro-4-(N-methyl)anilinopyrimidine (for Example 73).

The appropriate 2-chloro-4-anilinopyrimidine starting materials of Formula (S1-1) are either commercially available or are readily prepared by standard methods from known materials (by analogy to Method A and the corresponding Reference Examples A-1–A-10).

For Example 70, 2-chloro-4-[indan-5-ylamino]pyrimidine was prepared by reaction of 2,4-dichloropyrimidine with 5-aminoindane (by analogy to Method A and the corresponding Reference Examples A-1–A-10).

For Example 73, 2-chloro-4-(N-methyl)anilinopyrimidine was prepared from 2,4-dichloropyrimidine and N-methylaniline (by analogy to Method A and the corresponding Reference Examples A-1–A-10).

(ii) operations were carried out using a Zymate XP robot with solution additions via a Zymate Master Laboratory Station and stirred in a Stem RS5000 Reacto-Station at 25° C.;

(iii) column chromatography was performed using either an Anachem Sympur MPLC or Jones Flashmaster MPLC systems on Silica using a Mega Bond Elut column (10 g);

(iv) the structures of the end products was confirmed by L.C.M.S. on a Micromass OpenLynx system using the following:

| Ex No | $R_1$ | $R_2$ | NMR (300 MHz) | m/z (MH$^+$) |
|---|---|---|---|---|
| 68 | H | 4-cyclohexyl | 1.3 (m, 6H), 1.8 (m, 5H), 2.6 (s, 6H), 2.9 (m, 2H), 3.9 (d, 2H), 4.1 (m, 1H), 6.1 (d, 1H) 6.8 (d, 2H), 7.1 (d, 2H), 7.6 (m, 4H), 7.9 (d, 1H), 8.9 (s, 1H), 9.2 (s, 1H). | 462 |
| 69 | H | 2-phenyl | 2.8 (s, 6H), 3.2 (m, 4H), 3.9 (m, 1H), 5.9 (d, 1H), 6.0 (d, 1H), 6.7 (d, 2H), 7.3–7.5 (m, 12H), 7.8 (d, 1H) | 456 |
| 70 | H | So that Q2 is  | 2.0 (m, 2H), 3.8 (s, 6H), 3.8 (m, 4H), 3.1 (m, 2H), 3.9 (d, 2H), 4.2 (m, 1H), 6.1 (d, 1H), 6.8 (d, 2H), 7.1 (d, 1H), 7.3 (d, 1H), 7.6 (m, 3H), 7.9 (d, 1H), 8.9 (s, 1H), 9.1 (s, 1H). | 420 |
| 71 | H | 3-SO$_2$CH$_2$—CH$_2$OH | 2.9 (s, 6H), 3.2 (m, 1H), 3.3 (m, 1H), 3.4 (m, 2H), 3.7 (m, 2H), 4.0 (m, 2H), 4.3 (m, 1H), 6.4 (d, 1H), 6.9 (d, 2H), 7.5 (m, 4H), 8.0 (q, 2H), 8.1 (m, 1H). | 488 |
| 72 | H | 2-S—F$_5$Ph | 2.2 (s, 6H), 3.7 (m, 1H), 3.8 (m, 3H), 4.7 (m, 1H), 6.0 (d, 1H), 6.6 (d, 2H), 7.2 (m, 1H), 7.4 (m, 5H), 7.9 (d, 1H), 8.8 (s, 1H), 9.0 (s, 1H). | 578 |
| 73 | Me | H | 2.2 (s, 6H), 2.3 (m, 2H), 3.4 (s, 3H), 3.8 (m, 3H), 4.7 (d, 1H), 5.7 (d, 1H), 6.8 (d, 2H), 7.3 (m, 3H), 7.4 (m, 2H), 7.6 (d, 2H), 7.8 (d, 1H), 8.9 (s, 1H). | 394 |

Examples 74–77

Examples 74–77 of Formula (S1-2) wherein $R_1$ is hydrogen, were prepared by using a the method of Example 2 according to Scheme 1, using 4-[3-(N,N-dimethyl)amino-2-hydroxypropoxy]aniline (Reference Example D-1) and the appropriate 2-chloro-4-anilinopyrimidine of Formula (S1-1) wherein $R_1$ is hydrogen. The appropriate 2-chloro-4-anilinopyrimidine starting materials of Formula (S1-1) wherein $R_1$ is hydrogen are either commercially available or are readily prepared by standard methods from known materials (by analogy to Method A and the corresponding Reference Examples A-1–A-10).

The following conditions were used:
(i) evaporations were carried out in vacuo using a Savant AES 2000;

| Column: | 4.6 mm × 10 cm Hichrom RPB 5 Å |
|---|---|
| Solvent: | A = 95% Water + 0.1% Formic acid, B = 95% Acetonitrile + 0.1% Formic acid |
| Run time: | 15 minutes with a 10 minute gradient from 5–95% B |
| Wavelength: | 254 nm, bandwidth 10 nm |
| Mass detector | Platform LC |

| Ex No | $R_2$ | m/z [MH$^+$] | HPLC retention time (min) |
|---|---|---|---|
| 74 | 3-acetamido | 437 | 2.20 |
| 75 | 2-benzimidazol-2-yl | 496 | 6.69 |
| 76 | 4-(2-chloro-1,1,2-trifluoroethoxy)- | 512 | 7.41 |
| 77 | 4-phenoxy | 472 | 7.47 |

Examples 78–85

Examples 78–85 of Formula (S1-2) were prepared by the method of Example 2, according to Scheme 1, using 4-[3-(N,N-dimethyl)amino-2-hydroxypropoxy]aniline (Reference Example D-1) and the appropriate 2-chloro-4-(N-alkylated)anilinopyrimidine intermediate of Formula (S1-1) or, for Example 84, 2-chloro-4-[indan-5-yl(N-3-phenylprop-2-enyl)amino]pyrimidine.

The appropriate 2-chloro-4-(N-alkylated)anilinopyrimidine intermediates of Formula (S1-1) were prepared according to Scheme 2 by analogy to Method E described above and further below, using the appropriate 2-chloro-4-anilinopyrimidine intermediate (prepared by analogy to Method A and the corresponding Reference Examples A-1–A-10) and the appropriate alkylating agent.

For Example 84, 2-chloro-4-[indan-5-yl(N-3-phenylprop-2-enyl)amino]pyrimidine was prepared by reaction of 2,4-dichloropyrimidine with 5-aminoindane (by analogy to Method A and the corresponding Reference Examples A-1–A-10), followed by reaction with 3-phenylprop-2-enyl-chloride or bromide by analogy with Method E.

| Ex No | $R_1$ | $R_2$ | NMR (400 MHz, 373K) | m/z (MH⁺) |
|---|---|---|---|---|
| 78 | —CH$_2$CH$_2$CH$_2$CF$_3$ | 2-F-5-CH$_3$ | 1.97 (m, 2H), 2.38 (m, 2H), 2.47 (s, 3H), 2.99 (s, 6H), 3.33 (m, 1H), 3.44 (dd, 1H), 4.09 (m, 4H), 4.43 (m, 1H), 5.98 (d, 1H), 7.02 (d, 2H), 7.41 (m, 3H), 7.57 (d, 2H), 8.06 (d, 1H), 9.73 (bs, 1H). | 522.6 |
| 79 | —CH$_2$CH$_2$CH$_2$CF$_3$ | 3,4-diCl | 1.82 (m, 2H), 2.29 (m, 2H), 2.85 (s, 6H), 3.19 (m, 1H), 3.30 (dd, 1H), 3.96 (m, 4H), 4.32 (m, 1H), 5.98 (d, 1H), 6.88 (d, 2H), 7.37 (dd, 1H), 7.42 (d, 2H), 7.67 (s, 1H), 7.73 (d, 1H), 7.94 (d, 1H), 9.56 (bs, 1H). | 558.6 |
| 80 | —CH$_2$CH=CHBr | 2-F-5-CH$_3$ | 2.25 (s, 6H), 2.34 (s, 3H), 2.37 (m, 1H), 2.46 (dd, 1H), 3.90 (m, 3H), 4.44 (d, 1H), 4.60 (d, 1H), 5.70 (d, 1H), 6.45 (bm, 2H), 6.80 (m, 2H), 7.51 (m, 2H), 7.92 (m, 1H), 8.57 (s, 1H). | 530.4 |
| 81 | —CH$_2$CH=CHPh | 2-F-4-CH$_3$ | 2.27 (s, 6H), 2.43 (m, 5H), 3.92 (m, 3H), 4.32 (bs, 1H), 4.66 (d, 2H), 5.77 (d, 1H), 6.39 (m, 1H), 6.59 (d, 1H), 6.81 (d, 2H), 7.19 (m, 2H), 7.27 (m, 1H), 7.35 (m, 5H), 7.54 (d, 2H), 7.95 (d, 1H), 8.56 (s, 1H). | 528.5 |
| 82 | —CH$_2$CH=CHPh | 2-F-5-CH$_3$ | 2.23 (s, 6H), 2.32 (s, 3H), 2.39 (m, 2H), 3.88 (m, 3H), 4.30 (bs, 1H), 4.63 (d, 2H), 5.77 (d, 1H), 6.32 (m, 1H), 6.59 (d, 1H), 6.78 (d, 2H), 7.27 (m, 8H), 7.50 (d, 2H), 7.91 (d, 1H), 8.51 (s, 1H). | 528.5 |
| 83 | —CH$_2$CH=CHPh | 2-CN | 2.23 (s, 6H), 2.33 (m, 1H), 2.44 (dd, 1H), 3.88 (m, 3H), 4.29 (bs, 1H), 4.70 (d, 2H), 5.83 (d, 1H), 6.37 (m, 1H), 6.60 (d, 1H), 6.75 (d, 2H), 7.21 (d, 1H), 7.31 (m, 4H), 7.44 (d, 2H), 7.58 (d, 2H), 7.82 (m, 1H), 7.91 (d, 1H), 7.99 (d, 1H), 8.59 (s, 1H). | 521.5 |
| 84 | —CH$_2$CH=CHPh | So that Q2 is  | 2.09 (m, 2H), 2.22 (s, 6H), 2.34 (m, 1H), 2.42 (dd, 1H), 2.93 (m, 4H), 3.89 (m, 3H), 4.28 (bs, 1H), 4.67 (d, 2H), 5.71 (d, 1H), 6.38 (m, 1H), 6.55 (d, 1H), 6.80 (d, 2H), 7.08 (d, 1H), 7.20 (m, 2H), 7.32 (m, 5H), 7.56 (d, 2H), 7.83 (d, 1H), 8.43 (s, 1H). | 536.6 |

-continued

| Ex No | R₁ | R₂ | NMR (400 MHz, 373K) | m/z (MH⁺) |
|---|---|---|---|---|
| 85 | —(CH₂)₆OH | 2,5-diCl | 1.35 (m, 4H), 1.44 (m, 2H), 1.63 (m, 2H), 2.86 (s, 6H), 3.20 (m, 1H), 3.32 (dd, 1H), 3.41 (t, 2H), 3.81 (t, 2H), 3.97 (m, 2H), 4.31 (m, 1H), 5.76 (d, 1H), 6.83 (d, 2H), 7.47 (d, 2H), 7.52 (m, 2H), 7.68 (d, 1H), 7.96 (d, 1H), 8.89 (bs, 1H). | 548.5 |

Preparation of Starting Materials for Examples 78–85

The appropriate 2-chloro-4-(N-alkylated)anilinopyrimidine intermediates of Formula (S1-1) for Examples 78–83 and 85 above are either commercially available or are readily prepared by standard methods from known materials, according to Scheme 2. For example, the following reactions are further illustrations, but not limitations, of the preparation of some of the starting materials used in the above Examples.

Reference Example E-2

2-Chloro-4-[N-(4,4,4-trifluorobutyl]-2-fluoro-5-methylanilino]pyrimidine 4-(2-Fluoro-5-methylanilino)-2chloropyrimidine (Reference Example A-10, 750 mg, 3.16 mmol), 4,4,4-trifluoro-1-bromobutane (725 mg, 3.80 mmol) and potassium carbonate (525 mg, 3.80 mmol) were dissolved in DMF (3 ml). The reaction mixture was stirred at room temperature for 12 hours and then evaporated onto silica (5 ml) and purified by column chromatography eluting with EtOAc (0–40%):isohexane to give the title product as a solid on evaporation (976 mg). NMR (300 MHz, 373K): 1.79 (m, 2H), 2.28 (m, 2H), 2.33 (s, 3H), 3.91 (t, 2H), 6.19 (d, 1H), 7.28 (m, 3H), 8.03 (d, 1H); m/z (EI⁺) 347 (M+).

The Table immediately below shows by analogy to a Reference Example how the various intermediates for Examples 78–85 were prepared. The appropriate Intermediate A (un-N-alkylated 2-chloropyrimidine) being prepared by the relevant Method A and the appropriate Intermediate E (N-alkylated 2-chloropyrimidine) being prepared by the relevant Method E.

| Methods used | Ex No | Intermediate A m/z (MH⁺) | Intermediate E m/z (MH⁺) |
|---|---|---|---|
| A-3 + E-2 | 78 | 238.1 | 348 |
| A-3 + E-2 | 79 | 274.1 | 384 |
| A-3 + E-2 | 80 | 238.1 | 356 |
| A-3 + E-2 | 81 | 238.1 | 354.3 |
| A-3 + E-2 | 82 | 238.1 | 354.3 |
| A-7 + E-2 | 83 | 231.1 | 347.2 |
| A-3 + E-2 | 84 | 246.2 | 362.3 |
| A-4 + E-1 | 85 | 273.9 | 374.2 |

Example 86

2-{4-[3-(N,N-Dimethyl)amino-2-hydroxypropoxy]anilino}-4-(N-(2-phenylethyl)anilino)pyrimidine 2-Chloro-4-(N-(2-phenylethyl)anilino)pyrimidine (Reference Example E-3; 270 mg, 0.87 mmol) was dissolved in NMP (2 ml), 4-[3-(N,N-dimethyl)amino-2-hydroxypropoxy]aniline hydrochloride (Reference Example D-1; 222 mg, 0.90 mmol) was added and the mixture heated at 120° C. for 12 hours. The solvent was evaporated, the residue was resolubilized in methanol/ammonia 6M and evaporated again to dryness. The resulting solid was purified by flash chromatography using increasingly polar solvent mixtures starting with DCM and ending with DCM/methanol with 10% ammonia (87.5/12.5). Evaporation of the solvent gave a foam which was triturated in ether to give the title product as a white solid (150 mg, 36%). NMR: (400 MHz, 353K) 2.30 (s, 6H), 2.50 (m, 2H), 2.90 (m, 2H), 3.80 (m, 1H), 3.85 (m, 1H), 3.95 (br s, 1H), 4.10 (m, 2H), 5.00 (br s, 1H), 5.50 (d, 1H), 6.70 (d, 2H), 7.15 (m, 3H), 7.25(m, 4H), 7.35 (t, 1H), 7.50 (t, 2H), 7.60 (d, 2H), 7.80 (d, 1H), 8.85 (s, 1H), M.S.: (ES⁺) 484 (MH⁺).

Reference Example E-3

2-Chloro-4-(N-(2-phenylethyl)anilino)pyrimidine

2-Chloro-4-anilinopyrimidine (Reference Example A-9, 600 mg, 2.9 mmol) was dissolved in anhydrous DMF (8 ml) and sodium hydride (140 mg, 3.5 mmol, 60% in oil) was added portion wise. 10 min later phenethylbromide (478 μl, 3.5 mmol) was added and the mixture was stirred at ambient temperature for 5 hours. More sodium hydride (140 mg, 3.5 mmol, 60% in oil) and phenethylbromide (478 μl, 3.5 mnmol) were added and stirring was maintained overnight. The solvent was evaporated off and the residue partitioned between water and DCM. The organic phase was dried (MgSO₄) the solvent evaporated. The crude product was purified by flash chromatography using first DCM then EtOAc/petroleum ether (25/75). The solvent was evaporated to give the title product as a white solid (530 mg, 59%). NMR (400 MHz, 353K): 2.90 (t, 2H), 4.10 (t, 2H), 6.15 (d, 1H), 7.25 (m, 7H), 7.45 (t, 1H), 7.65 (t, 2H), 8.00 (d, 1H); m/z: (ES⁺) 310 and 312 (MH⁺).

Example 87

2-{4-[3-(N,N-Dimethylamino)-2-hydroxypropoxy]anilino}-4-(N-(pyrid-4-ylmethyl)anilino)pyrimidine Using a procedure analogous to that described for Example 86, 2-chloro-4-(N-(pyrid-4-ylmethyl)anilino)pyrimidine (Reference Example E-4, 230 mg, 0.77 mmol) gave the title product as a greyish solid (124 mg, 34%). NMR (400 MHz, 353K): 2.25 (s, 6H), 2.40 (br m, 2H), 3.80 (m, 1H), 3.90 (m, 2H), 4.90 (br s, 1H), 5.25 (s, 2H), 5.80 (d, 1H), 6.70 (d, 1H), 7.30–7.50 (m, 10H), 7.90 (d, 1H), 8.50 (d, 2H), 9.00 (s, 1H); m/z: (ES⁺) 471 (MH⁺).

Reference Example E-4

2-Chloro-4-(N-(pyrid-4-ylmethyl)anilino)pyrimidine

Using a procedure similar to the one described for Reference Example E-3, 2-chloro-4-anilinopyrimidine (Reference Example A-9, 500 mg, 2.4 mmol) was reacted with 4-bromomethyl pyridine (7.38 mg, 1.2 mmol) to give, after work-up and purification, the the title product (230 mg, 32%). NMR (400 MHz, 353K): 5.20 (s, 2H), 6.35 (d, 1H), 7.30 (d, 2H), 7.40 (m, 3H), 7.50 (t, 2H), 8.10 (d, 1H), 8.50 (d, 2H); m/z (ES) 297 (MH$^+$).

Example 88

2-{4-[3-(N,N-Dimethyl)amino-2-hydroxypropoxy]anilino}-4-(N-(2-cyclohexylethyl)anilino)pyrimidine Using a procedure similar to the one described for Example 86, 2-chloro-4-(N-(2-cyclohexylethyl)anilino)pyrimidine (Reference Example E-5, 360 mg, 1.1 mmol) gave the title product as a greyish solid (211 mg, 40%). NMR (400 MHz, 353K): 0.90 (m, 2H), 1.20 (m, 3H), 1.30 (m, 1H), 1.50 (m, 2H), 1.65 (m, 5H), 2.65 (s, 3H), 3.00 (m, 2H), 3.90 (m, 4H), 4.15 (br s, 1H), 5.60 (d, 1H), 6.80 (d, 1H), 7.30 (d, 1H), 7.40 (t, 1H), 7.50 (t, 1H), 7.65 (d, 1H), 7.80 (d, 1H), 9.85 (s, 1H); m/z (ES$^+$) 490 (MH$^+$).

Reference Example E-5

2-Chloro-4-(N-(2-cyclohexylethyl)anilino)pyrimidine

2-Chloro-4-anilinopyrimidine (Reference Example A-9, 700 mg, 3.4 mmol) was dissolved in DCM (70 ml), triphenyl phosphine (1.07 g, 4.1 mmol) and 2-cyclohexyl ethanol (0.57 ml, 4.1 mmol) were added followed by dropwise addition of DEAD (0.646 ml, 4.1 mmol). After 1 hour additional triphenyl phosphine (0.5 g, 2 mmol), 2-cyclohexyl ethanol (0.28 ml, 2 mmol) and DEAD (0.320 ml, 2 mmol) were added and the reaction mixture was stirred overnight at ambient temperature. The solvent was evaporated off and the residue was purified by flash chromatography using EtOAc/petroleum ether (15/85, then 20/80) as the eluent. The solvent was evaporated to give the title product as a colourless oil (368 mg, 37%). NMR (400 MHz, 353K): 0.90 (m, 2H), 1.20 (m, 3H), 1.30 (m, 1H), 1.65 (m, 7H), 3.90 (t, 2H), 4.05 (m, 1H), 6.10 (d, 1H), 7.34 (d, 2H), 7.43 (t, 1H), 7.54 (t, 2H), 7.95 (d, 1H); m/z (ES$^+$) 316 and 318 (MH$^+$).

Example 89

2-{4-[3-(N,N-Dimethyl)amino-2-hydroxypropoxy]anilino}-4-(N-(3-morpholinopropyl)anilino)pyrimidine Using a procedure analogous to that described for Example 86 except that heating was at 100° C. for 7 hours. 2-chloro-4-(N-(3-morpholinopropyl)anilino)pyrimidine (Reference Example E-6, 280 mg, 0.84 mmol) gave the title product as a solid (38 mg, 7%). NMR (400 MHz, 353K): 2.00 (m, 2H), 2.80 (d, 3H), 2.85 (d, 3H), 3.0 (m, 4H), 3.30 (m, 4H), 3.7 (t, 2H), 4.0 (m, 6H), 4.30 (m, 1H), 5.7 (m, 1H), 7.10 (m, 3H), 7.3–7.6 (m, 6H), 7.85 (m, 1H); m/z: (ES$^+$) 507 (MH$^+$).

Reference Example E-6

2-Chloro-4-(N-(3-morpholinopropyl)anilino)pyrimidine

2-Chloro-4-anilinopyrimidine (Reference Example A-9, 400 mg, 1.9 mmol) was dissolved in DCM (23 ml), triphenyl phosphine (612 mg, 2.3 mmol) and 3-N-morpholinopropanol (0.1 mg, 2.1 mmol) were added followed by dropwise addition of DTAD (537 mg, 2.3 mmol). The reaction mixture was stirred overnight at ambient temperature. The solvent was evaporated off and the residue was purified by flash chromatography using first DCM then EtOAc as the eluent. The solvent was evaporated to give the title product as a colourless oil (560 mg, 88%). NMR (400 MHz, 353K): 1.70 (m, 2H), 2.30 (m, 6H), 3.55 (m, 4H), 3.90 (m, 2H), 6.15 (m, 1H), 7.35–7.70 (m, 5H), 7.95 (m, 1H); m/z (ES$^+$) 333 and 335 (MH$^+$).

Example 90

2-{4-[3-(N,N-Dimethyl)amino-2-hydroxypropoxy]anilino}-4-(N-(3-phenylprop-2-ynyl)anilino)pyrimidine Using a procedure analogous to the one described for Example 86 except that heating was at 120° C. for 2 hours. 2-chloro-4-(N-(3-phenylprop-2-ynyl)anilino)pyrimidine (Reference Example E-7, 440 mg, 1.3 mmol) gave the title product as a solid (250 mg, 39%). NMR (400 MHz, 353K): 2.20 (s, 6H), 2.25–2.40 (m, 2H), 3.80 (m, 1H), 3.90 (m, 2H), 4.80 (s, 1H), 4.95 (s, 2H), 5.75 (d, 1H), 6.80 (d, 2H), 7.35 (s, 5H), 7.45 (m, 3H), 7.55 (t, 2H), 7.70 (d, 2H), 7.90 (d, 1H), 9.10 (s, 1H); m/z: (ES$^+$) (MH$^+$).

Reference Example E-7

2-Chloro-4-(N-(3-phenylprop-2-ynyl)anilino)pyrimidine

Using a procedure analogous to that described for Reference Example E-6, 2-chloro-4-anilinopyrimidine (Reference Example A-9, 500 mg, 2.4 mmol) gave, after reaction with triphenylphosphine, DTAD and 3-phenyl-2-propyn-1-ol, the title product as a colourless gum (440 mg, 57%). NMR (400 MHz, 353K): 4.95 (s, 2H), 6.30 (d, 1H), 7.35 (s, 5H), 7.45 (m, 3H), 7.60 (m, 2H), 8.10 (d, 1H); m/z: (ES$^+$) 320 and 322 (MH$^+$).

Example 91

2-{4-[3-(N,N-Dimethyl)amino-2-hydroxypropoxy]anilino}-4-anilinopyrimidine

4-Anilino-2-(4-(2,3-epoxypropoxy)anilino)pyrimidine (Reference Example I-1, 0.61 g, 1.84 mmol) was dissolved in DMF (2 ml) and treated with dimethylamine (6 mmol, 3 ml of a 2M solution in EtOH). After stirring overnight at ambient temperature the reaction mixture was partitioned between EtOAc and water. The organic phase was washed with water, dried over MgSO$_4$ and evaporated at reduced pressure. The residue was purified by chromatography (0.1%NH$_3$ (aq), 3–10% MeOH in DCM as eluent). Upon evaporation of the fractions, an oily product was obtained, this was triturated with ether to give the title product as a white solid (0.126 g, 18%). NMR (300 MHz): 2.2 (s, 6H), 2.3–2.8 (m, 2H), 3.75–3.95 (m, 3H(, 4.82 (brs, 1H), 6.17 (d, 1H), 6.82 (d, 2H), 6.97 (t, 1H), 7.27 (t, 2H), 7.58 (d, 2H), 7.66 (d, 2H), 7.95 (d, 1H), 8.95 (s, 1H), 9.25 (s, 1H); m/z: (ES$^+$) 380.4 (MH$^+$).

Reference Example A-9

2-Chloro-4-anilinopyrimidine 2,4-Dichloropyrimidine (3.75 g, 25 mmol) was dissolved in EtOH (12 ml) and treated with aniline (2.27 ml, 25 mmol) and triethylamine (3.82 ml, 27.2 mmol). The reaction mixture was heated to reflux for 6 hours, partitioned between EtOAc and water. The organic phase was washed with 1M HCl, dried over MgSO$_4$ and evaporated to obtain a cream coloured solid. This material was purified by chromatography (25–50% EtOAc in isohexane) to give the title product as an off white solid. NMR (300 MHz) 6.73 (d, 1H), 7.08 (t, 1H), 7.35 (t, 2H), 7.57 (d, 2H), 8.12 (d, 1H), 9.95 (brs, 1H); m/z: (ES$^+$) 206 (MH$^+$).

Method H: Reaction of 4-anilino-2-chloropyrimidines with anilines

Reference Example H-1

4-Anilino-2-(4-hydroxyanilino)pyrimidine

4-Anilino-2-chloropyrimidine (Reference Example A-9, 0.921 g, 4.48 mmol) was dissolved in butanol (6 ml) and treated with 4-hydroxyaniline (0.489 g, 4.48 mmol) and conc. HCl (9 drops). The reaction was heated to 80° C. for 4 hours. The solvent was removed by evaporation at reduced pressure to give the title product as a solid which was used without further purification (1.4 g) NMR (300 MHz): 6.43 (d, 1H), 6.68 (d, 2H) 7.14 (t, 1H), 7.25 (m, 4H), 7.64 (m, 2H), 7.88 (s, 1H) 9.53 (brs, 1H), 10.27 (brs, 1H). 10.88 (brs, 1H); m/z: (ES$^-$) 279 (MH$^+$).

Method I: Reaction of 4-anilino-2-(4-hydroxyanilino)pyrimidines with bromoalkylepoxides Reference Example I-1

4-Anilino-2-[4-(2,3-epoxypropoxy)anilino]pyrimidine

4-Anilino-2-(4-hydroxyanilino)pyrimidine (Reference Example H-1, 0.541 g, 1.95 mmol) was dissolved in DMSO (2 ml) and treated with K$_2$CO$_3$ (0.537 g, 3.89 mmol) and epibromohydrin (0.33 ml, 0.53 g, 3.9 mmol). The reaction was allowed to stir at ambient temperature overnight. After warming to 40° C. for 5 hours the reaction was partitioned between EtOAc and water. The organic phase was washed four times with water, dried over MgSO$_4$ and evaporated at reduced pressure. The residue was purified by chromatography (1–5% MeOH in DCM) to give the title product as an oil (0.614 g, 94%). NMR (300 MHz): 2.69 (m, 1H), 2.83 (m, 1H), 3.88 (m, 1H), 4.25 (m, 1H), 6.15 (d, 1H), 6.85 (d, 2H), 7.97 (t, 1H), 7.27 (t, 2H), 7.58 (d, 2H), 7.66 (d, 2H), 7.95 (d, 1H), 8.9 (s, 1H), 9.23 (s, 1H); m/z: (ES$^+$) 335 (MH$^+$).

Example 92

2-{4-[3-(N,N-Dimethyl)aminopropoxy]anilino}-4-(2-fluoro-5-methylanilino)pyrimidine 4-(2-fluoro-5-methylanilino)-2-(4-hydroxyanilino)pyrimidine (Reference Example H-2, 250 mg, 0.57 mmol) was dissolved in DMSO (2 ml) and K$_2$CO$_3$ (205 mg, 1.5 mmol) was added. The resulting suspension was stirred for 30 mins to give a turquoise solution. 3-(N,N-Dimethylamino)propyl chloride HCl (122 mg, 0.77 mmol) was added and the mixture stirred at 100° C. for 3 hours. To this brown solution was added DCM (20 ml) and silica (3 g). The mixture was evaporated to dryness under high vacuum and the residue loaded onto a Mega Bond Elute column (10 g) which was eluted with DCM (2×25 ml), 2% NH$_3$ in MeOH (3×25 ml), 4% NH$_3$ in MeOH (3×25 ml), 6% NH$_3$ in MeOH (3×25 ml) and 10% NH$_3$ in MeOH (9×25 ml) to give the title product as a colourless gum (75 mg, 29%). M/z (ES$^+$) 396 (MH$^+$), HPLC (Hypersil 10 cm base deactivated) (60% MeCN/H$_2$O/0.2% TFA) Retention time: 4.60 min.

Reference Example H-2

4-(2-Fluoro-5-methylanilino)-2-(4-hydroxyanilino) pyrimidine 4-(2-Fluoro-5-methylanilino)-2-chloropyrimidine (Reference Example A-10, 1.00 g, 4.2 mmol) was dissolved in NMP (5 ml) and 4-hydroxyaniline (0.41 g, 3.7 mmol) and 1M HCl in diethyl ether (4.22 ml, 4.2 mmol) was added. The reaction mixture was heated at 100° C. for 15 hours, and then allowed to cool to ambient temperature. The mixture was evaporated under high vacuum to give the title product as a brown oil. The residue was purified by chromatography on a Mega Bond Elute column (10 g) eluting with DCM (4×25 ml), 2% NH$_3$/MeOH in DCM (3×25 ml), 4% NH$_3$/MeOH in DCM (3×25 ml), 6% NH$_3$/MeOH in DCM (10×25 ml to give the title product as a white solid (0.80 g, 61%). NMR (300 MHz): 2.2 (s, 3H), 6.2 (d, 1H), 6.6 (d, 2H), 6.9 (m, 1H), 7.1 (m, 1H), 7.4 (d, 2H), 7.8 (d, 1H), 7.9 (d, 1H), 8.7 (s, 1H), 8.8 (s, 1H), 8.9 (s, 1H); m/z: (ES$^+$) 311.0 (MH$^+$).

Reference Example H-3

4-(2-Fluoro-5-methylanilino)-2-(3-hydroxyanilino) pyrimidine

The title compound was prepared by an analogous method to Reference Example H-2 using 3-hydroxyaniline instead of 4-hydroxyaniline. NMR (300 MHz): 2.2 (s, 3H), 6.4 (m, 2H), 6.8–7.2 (m, 5H), 7.8 (d, 1H), 8.0 (d, 1H), 9.1 (m, 3H); m/z: (ES$^+$) 311.0 (MH$^+$).

Reference Example A-10

4-(2-Fluoro-5-methylanilino)-2-chloropyrimidine 2,4-Dichloropyrimidine (7.0 g, 47 mmol) was dissolved in n-butanol (5 ml), followed by addition of DIPEA (9.0 ml, 51.7 mmol), then 2-fluoro-5-methylaniline (5.3 ml, 47 mmol). The mixture was heated at 100° C. overnight, and then allowed to cool to ambient temperature. The mixture was evaporated to give an oil, which was taken up in DCM (250 ml) and washed with water (3×50 ml), brine (50 ml), dried over MgSO$_4$ and evaporated to give an orange oil. This was purified by column chromatography eluting with EtOAc:isohexane (10:90) to give the title product as a white solid (2.40 g, 21%). NMR (300 MHz): 2.3 (s, 3H), 6.7 (d, 1H), 7.0 (m, 1H), 7.2 (m, 1H), 7.5 (d, 1H), 8.1 (d, 1H), 9.7 (s, 1H); m/z: (ES$^+$) 237.9 (MH$^+$).

Examples 93–95

Examples 93–95 were prepared, according to Scheme 3, by an analogous procedure to that used for Example 92, using the appropriate 4-(2-fluoro-5-methylanilino)-2-(3- or 4-hydroxyanilino)pyrimidine of Formula (S3–1) and the appropriate commercially available haloalkylamine HCl salt.

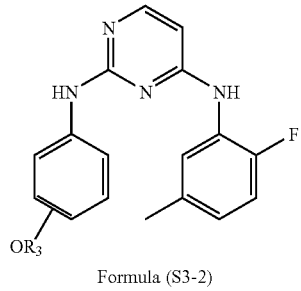

Formula (S3-2)

| Ex No | OR$_3$ | m/z (MH$^+$) | HPLC (Hypersil 10 cm base deactivated) Retention time 60% MeCN/H$_2$O/0.2% TFA |
|---|---|---|---|
| 93 | 4- —O—CH$_2$CH$_2$—N(CH$_2$CH$_2$)$_2$N—Me | 451.3 | 3.35 min. |
| 94 | 4- —O—CH$_2$CH$_2$—N(Me)$_2$ | 396.2 | 3.85 min. |
| 95 | 3- —O—CH$_2$CH$_2$—N(CH$_2$CH$_2$)$_2$N—Me | 451.3 | 3.55 min. |

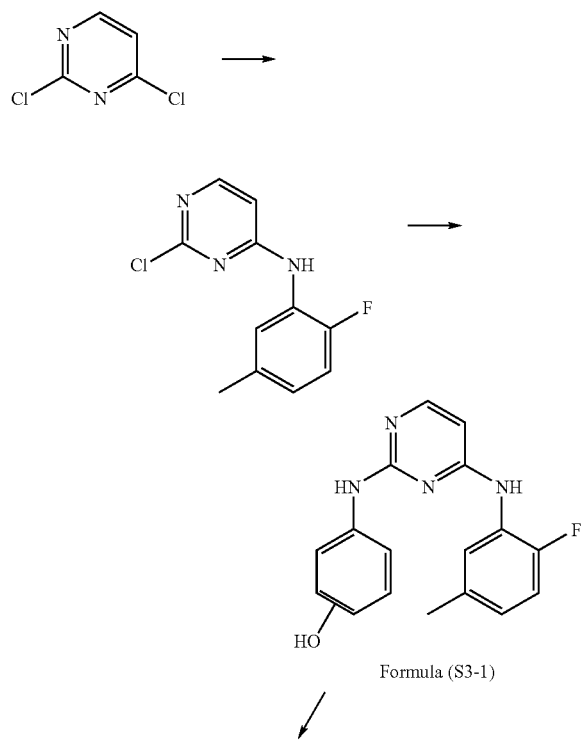

Scheme 3

Formula (S3-1)

Example 96

4-(2-Fluoro-5-methylanilino)-2-[4-(3-morpholinopropoxy)anilino]pyrimidine 4-(2-Fluoro-5-methylanilino)-2-chloropyrimidine (Reference Example A-10, 140 mg, 0.6 mmol) was dissolved in dry NMP (2 ml) and 4-(3-morpholinopropoxy)aniline.2.HBr salt (see CAS Registry No. 100800–40–6; J.Am.Chem.Soc., 76, 1954, 4396; 188 mg, 0.5 mmol) added. The mixture was stirred at ambient temperature for 5 minutes, then checked to ensure the reaction mixture was acidic (pH 1) and heated at 100° C. for 3 hours. The mixture was allowed to cool and evaporated to dryness to give an oil. Silica (2 g) and DCM (10 ml) were added and the mixture then re-evaporated to dryness and purified by chromatography on a Mega Bond Elute column (10 g) (eluting with DCM (2×25 ml), 2% NH$_3$ in MeOH (3×25 ml), 4% NH$_3$ in MeOH (3×25 ml), 6% NH$_3$ in MeOH (3×25 ml), 10% NH$_3$ in MeOH (9×25 ml)) to give the title product as a colourless oil, which was triturated with diethyl ether to give a white solid (95 mg, 46%). NMR (300 MHz): 1.8 (m, 2H), 2.2 (s, 3H), 2.4 (m, 4H), 2.4 (m, 2H), 3.6 (t, 3H), 3.9 (t, 2H), 6.2 (d, 1H), 6.8 (d, 2H), 6.9 (m, 1H), 7.1 (m, 1H), 7.5 (d, 2H), 7.8 (d, 1H), 8.0 (d, 1H), 8.9 (s, 2H); m/z: (ES$^+$) 438.2 (MH$^+$).

Example 97

2-{4-[3-(N,N-Dimethyl)amino-2-hydroxypropyl(N-methyl)amino]anilino}-4-(2-fluoro-5-methylanilino) pyrimidine By a procedure analogous to Example 96, 4-(2-fluoro-5-methylanilino)-2-chloropyrimidine (Reference Example A-10) and 4-[3-(N,N-dimethyl)amino-2-hydroxypropyl(N-methyl)amino]aniline (Reference Example D-2) were reacted to give the title product as a brown oil (60 mg, 17%). M/z: (ES$^+$) 425.3 (MH$^+$). HPLC (Hypersil 10 cm base deactivated) 60% MeCN/H$_2$O/0.2% TFA. Retention time: 2.66 min.

Method J: Reaction of Anilines with Bromoalkylepoxides Followed by Opening of the Epoxide with an Amine.

Reference Example J-1

4-[3-(N,N-dimethyl)amino-2-hydroxypropyl(N-methyl)amino]nitrobezene

4-Nitro-N-methylaniline (1.00 g, 6.6 mmol) was dissolved in DMF (50 ml) and cooled to 0° C. in an ice bath. Sodium hydride (290 mg, 7.2 mmol, 60% dispersion in mineral oil) was added portion wise over 30 mins to give an orange/brown solution. To this was added epibromohydrin (0.62 ml, 7.2 mmol) dropwise and the mixture left to stir at ambient temperature for 12 hours. The mixture was evaporated to give a yellow oily residue, to which was added dimethylamine 2.0 M in MeOH (66 ml, 0.13 mol) and left to stir at ambient temperature for 12 hours. The mixture was evaporated to give a yellow solid, then taken up in DCM (100 ml), washed with H$_2$O (20 ml), brine (20 ml), dried over MgSO$_4$ and evaporated to dryness to give the title product as an orange solid (1.44 g, 86%). NMR (300 MHz): 2.2 (s, 6H), 2.3 (t, 2H), 3.1 (s, 3H), 3.3–3.6 (m, 2H), 3.8 (br s, 1H), 4.8 (d, 1H) 6.8 (d, 2H), 8.0 (d, 2H); m/z: (ES$^+$) 254.0 (MH$^+$).

Reference Example D-2

4-[3-(N,N-Dimethyl)amino-2-hydroxypropyl-(N-methyl)amino]aniline

4-[3-(N,N-Dimethyl)amino-2-hydroxypropyl-(N-methyl)amino]nitrobenzene (Reference Example J-1, 1.30 g, 5.1 mmol) was dissolved in EtOH (150 ml) and 10% Pd/C was added (130 mg, 10% b/w). The reaction was stirred under a hydrogen balloon for 3 hours. The reaction mixture was then filtered through a pad of celite and washed thoroughly with more EtOH. The solution was evaporated to give a brown oil. DCM was added to solubilise then 1M HCl in diethyl ether added to form the HCl salt, as a green solid in solution. The hygroscopic salt was filtered quickly, drying in a dessicator overnight to give the title product (0.80 g, 60%). M/z: (ES$^+$) 224.0 (MH$^+$).

Example 98

4-(2-Fluoro-5-methylanilino)-2-[4-(3-N-isopropylamino-2-hydroxypropoxy)anilino]pyrimidine To a suspension of 4-(2-fluoro-5-methylanilino)-2-chloropyrimidine (Reference Example A-10, 117 mg) and 4-(3-N-isopropylamino-2-hydroxypropoxy)aniline (224 mg) in n-butanol (1 ml) was added a 1M HCl solution in diethyl ether (0.4 ml) and the mixture warmed to remove ether, then heated at reflux for 1.5 hours. The mixture was cooled and 2M ammonia solution in methanol (2 ml) was added. The product was pre-loaded onto silica and purified by column chromatography, eluting with DCM: (2M) methanolic ammonia; 92:8, to give the title product as a white solid (170 mg, 89%). NMR (300 MHz): 0.97 (6H, d), 2.26 (3H, s), 2.43–2.78 (3H, m), 3.76–3.91 (3H, m), 4.05 (1H, brs), 4.90 (1H, br s), 6.24 (1H, d), 6.77 (2H, d), 6.84–6.93 (1H, m), 7.11 (1H, dd), 7.51 (2H, d), 7.75 (1H, d), 7.96 (1H, d), 8.89 (2H, s), m/z: (ES$^+$) 426 (MH$^+$).

4-(3-N-Isopropylamino-2-hydroxypropoxy)aniline was prepared by analogy with Reference Examples B-1, C-1 and D-1, but using isopropylamine in place of dimethylamine in Method C.

Examples 99–102

The following compounds were similarly prepared, according to Scheme 4, by an analogous procedure to that used for Example 98, using the appropriate anilines (prepared by analogy with the preparation of the 4-(3-N-isopropylamino-2-hydroxypropoxy)aniline starting material of Example 98, using the appropriate amine in Method C).

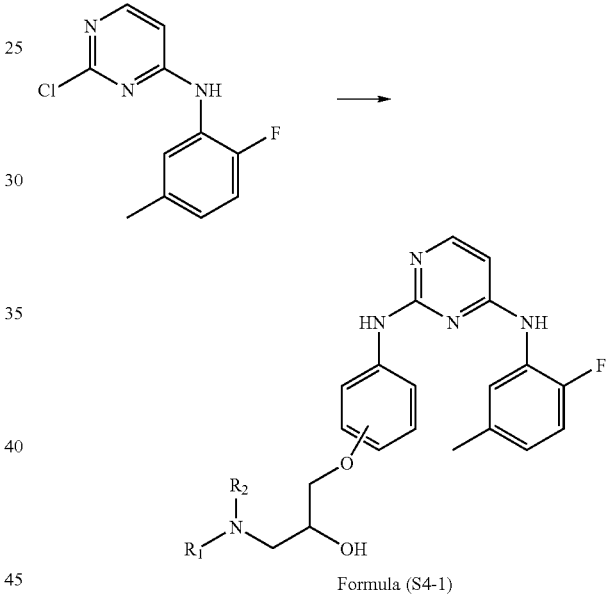

Scheme 4

Formula (S4-1)

| Ex No | 3 or 4 * | R$_1$ | R$_2$ | NMR (300 MHz) | m/z (MH$^+$) |
|---|---|---|---|---|---|
| 99 | 4 | H | cyclo-pentyl | 1.20–1.78 (8H, s), 2.26 (3H, s), 2.46–2.64 (2H, m), 2.98 (1H, m), 3.76–3.91 (3H, m), 4.86 (1H, br s), 6.24 (1H, d), 6.76 (2H, d), 6.87–6.93 (1H, m), 7.12 (1H, dd), 7.51 (2H, d), 7.74 (1H, d), 7.96 (1H, d), 8.88 (2H, s) | 452 |
| 100 | 4 | H | tert-butyl | 1.01 (9H, s), 2.26 (3H, s), 2.44–2.63 (2H, m), 3.70–3.92 (3H, m), 4.82 (1H, br s), 6.23 (1H, d), 6.76 (2H, d), 6.85–6.93 (1H, m), 7.11 (1H, dd), 7.51 (2H, d), 7.75 (1H, d), 7.96 (1H, d), 8.88 (2H, s) | 440 |

| Ex No | 3 or 4 * | $R_1$ | $R_2$ | NMR (300 MHz) | m/z (MH$^+$) |
|---|---|---|---|---|---|
| 101 | 4 | |  # | 1.59–1.74 (4H, m), 2.25 (3H, s), 2.38–2.63 (6H, m), 3.73–3.94 (3H, m), 4.76 (1H, d), 6.24 (1H, d), 6.76 (2H, d), 6.85–6.94 (1H, m), 7.11 (1H, dd), 7.50 (2H, d), 7.74 (1H, d), 7.96 (1H, d), 8.88 (2H, s) | 438 |
| 102 | 3 | H | isopropyl | 0.96 (6H, d), 2.26 (3H, s), 2.41–2.75 (3H, m), 3.71–3.86 (3H, m), 4.87 (1H, d), 6.28 (1H, d), 6.45 (1H, d), 6.86–6.95 (1H, m), 6.99–7.17 (2H, m), 7.22–7.34 (2H, m), 7.75 (1H, d), 8.01 (1H, d), 8.96 (1H, s), 9.03 (1H, s) | 426 |

\* Refers to position of side chain in Formula S4-1.
\# So that $R_1$, $R_2$ and the nitrogen atom to which they are attached form a pyrrolidin-1-yl ring.

Example 103

4-(2,5-Dichloroanilino)-2-[4-(3-N-isopropylamino-2-hydroxypropoxy)anilino]pyrimidine 2-Chloro-4-(2,5-dichloroanilino)pyrimidine (Reference Example A-4, 100 mg, 0.36 mmol) was dissolved in dry NMP (2 ml). 4-(2-Hydroxy-3-isopropylaminopropoxy)aniline hydrochloride (see Example 98; 90 mg, 0.35 mmol) and 1M ethereal HCl (0.8 ml) were added and the mixture heated to 100° C. for 3 hours. The brown solution was partitioned between EtOAc and saturated aqueous sodium bicarbonate solution. The organic layer was evaporated and the residue purified by column chromatography (7M NH$_3$/MeOH (4%): DCM). The resulting solid was broken up in isohexane, filtered and dried to give the title product (100 mg, 59%). NMR (300 MHz) 0.97 (d, 6H), 2.55–2.75 (m, 3H), 3.75–3.9 (m, 3H), 6.35 (d, 1H), 6.77 (d, 2H), 7.20 (q, 1H), 7.50 (m, 3H), 8.02 (m, 2H), 8.88 (brs, 1H), 8.99 (s, 1H); m/z (ES$^+$) 462 (MH$^+$).

Examples 104–107

The following compounds were similarly prepared, according to Scheme 5, by an analogous procedure to that used for Example 103, using the appropriate anilines (prepared by analogy with the preparation of the 4-(3-N-isopropylamino-2-hydroxypropoxy)aniline starting material of Example 98, using the appropriate amine in Method C).

Scheme 5

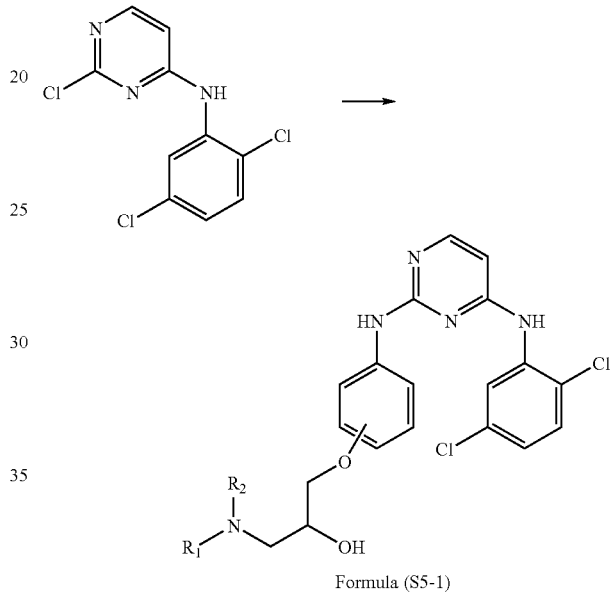

Formula (S5-1)

| Ex No | 3 or 4 * | $R_1$ | $R_2$ | NMR (300 MHz) | m/z (MH$^+$) |
|---|---|---|---|---|---|
| 104 | 4 | H | tert-butyl | 1.00 (s, 9H), 2.52–2.68 (m, 2H), 3.70–3.84 (m, 2H), 3.84–3.92 (m, 1H), 6.35 (d, 1H), 6.77 (d, 2H), 7.20 (q, 1H), 7.50 (m, 3H), 8.02 (m, 2H), 8.88 (brs, 1H), 8.99 (s, 1H) | 476 |
| 105 | 3 | H | isopropyl | 0.97 (d, 6H), 2.5–2.73 (m, 3H), 3.80 (m, 3H), 6.38 (d, 1H), 6.45 (dd, 1H), 7.04 (t, 1H), 7.10 (m, 2H), 7.29 (dd, 1H), 7.52 (d, 1H), 7.99 (d, 1H), 8.08 (d, 1H), 8.96 (brs, 1H), 9.13 (s, 1H) | 462 |
| 106 | 4 | |  # | 1.65 (m, 4H), 2.37–2.63 (m, 6H), 3.73–3.93 (m, 3H), 4.78 (brs, 1H), 6.35 (d, 1H), 6.77 (d, 2H), 7.20 (q, 1H), 7.50 (m, 3H), 8.02 (m, 2H), 8.88 (s, 1H), 8.99 (s, 1H) | 474 |
| 107 | 4 | H | cyclopentyl | 1.16 (m, 2H), 1.47 (m, 2H), 1.60 (m, 2H), 1.70 (m, 2H), 2.52–2.67 (m, 2H), 2.98 (m, 1H), 3.75–3.90 (m, 3H), 6.35 (d, 1H), 6.77 (d, 2H), 7.20 (q, 1H), 7.50 (m, 3H), 8.02 (m, 2H), 8.88 (s, 1H), 8.99 (s, 1H) | 488 |

\* Refers to position of side chain in Formula S4-1.
\# So that $R_1$, $R_2$ and the nitrogen atom to which they are attached form a pyrrolidin-1-yl ring.

Example 108

The following illustrate representative pharmaceutical dosage forms containing the compound of formula (I), or a pharmaceutically-acceptable salt or in-vivo hydrolysable ester thereof (hereafter compound X), for therapeutic or prophylactic use in humans:

| (a): Tablet I | mg/tablet |
| --- | --- |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
| --- | --- |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
| --- | --- |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
| --- | --- |
| Compound X | 10 |
| Lactose Ph.Eur | 488.5 |
| Magnesium stearate | 1.5 |

| (e): Injection I | (50 mg/ml) |
| --- | --- |
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | to 100% |

| (f): Injection II | 10 mg/ml |
| --- | --- |
| Compound X | 1.0% w/v |
| Sodium phosphate BP | 3.6% w/v |
| 0.1 M Sodium hydroxide solution | 15.0% v/v |
| Water for injection | to 100% |

| (g): Injection III | (1 mg/ml, buffered to pH6) |
| --- | --- |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What is claimed is:

1. A pyrimidine compound of the formula (I)

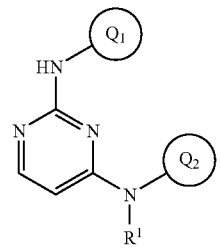

(I)

wherein $R^1$ is selected from (1–6C)alkyl [optionally substituted by one or two substituents independently selected from halo, amino, (1–4C)alkylamino, di-[(1–4C)alkyl]amino, hydroxy, cyano, (1–4C)alkoxy, (1–4C)alkoxycarbonyl, carbamoyl, —NHCO(1–4C)alkyl, trifluoromethyl, phenylthio, phenoxy, pyridyl, morpholino], benzyl, 2-phenylethyl, (3–5C)alkenyl [optionally substituted by up to three halo substituents, or by one trifluoromethyl substituent, or one phenyl substituent], N-phthalimido-(1–4C)alkyl, (3–5C)alkynyl [optionally substituted by one phenyl substituent] and (3–6C)cycloalkyl-(1–6C)alkyl;

wherein any phenyl or benzyl group in $R^1$ is optionally substituted by up to three substituents independently selected from halogeno, hydroxy, nitro, amino, (1–3C)alkylamino, di-[(1–3C)alkyl]amino, cyano, trifluoromethyl, (1–3C)alkyl [optionally substituted by 1 or 2 substituents independently selected from halogeno, cyano, amino, (1–3C)alkylamino, di-[(1–3C)alkyl]amino, hydroxy and trifluoromethyl], (3–5C)alkenyl [optionally substituted by up to three halo substituents, or by one trifluoromethyl substituent], (3–5C)alkynyl, (1–3C)alkoxy, —SH, —S-(1–3C)alkyl, carboxy, (1–3C)alkoxycarbonyl;

$Q_1$ and $Q_2$ are independently selected from phenyl, naphthyl, indanyl and 1,2,3,4-tetrahydronaphthyl;

and one or both of $Q_1$ and $Q_2$ bears on any available carbon atom one substituent of the formula (Ia) and $Q_2$ may optionally bear on any available carbon atom further substituents of the formula (Ia)

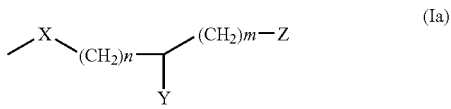

(Ia)

[provided that when present in Q₁ the substituent of formula (Ia) is not adjacent to the —NH— link];
wherein
X is O, S, NH or NRx [wherein Rx is (1–4C)alkyl, optionally substituted by one substituent selected from halo, amino, cyano, (1–4C)alkoxy or hydroxy];
Y is as defined for Z;
Z is OH, SH, NH₂, (1–4C)alkoxy, (1–4C)alkylthio, —NH(1–4C)alkyl, —N[(1–4C)alkyl]₂, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;
n is 1, 2 or 3; m is 1, 2 or 3;

and Q₁ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]- carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido (H₂N—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N—[(1–4C)alkyl]carbamoyl, N,N-di-[(1–4C)alkyl]carbamoyl, amino, (1–4C)alkylamino, di-[(1–4C)alkyl]amino, (2–4C)alkanoylamino;

and also independently, or in addition to, the above substituents, Q₁ may optionally bear on any available carbon atom up to two further substituents independently selected from (3–8C)cycloalkyl, phenyl-(1–4C)alkyl, phenylthio, phenyl, naphthyl, benzoyl, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenylthio substituents may optionally bear up to five substituents independently selected from halogeno, (1–4C)alkyl and (1–4C)alkoxy;

and Q₂ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, cyano-(1–4C)alkoxy, carbamoyl-(1–4C)alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido (H₂N—CO—NH—), (1–4C)alkylNH—CO—NH—, di-[(1–4C)alkyl]N—CO—NH—, (1–4C)alkylNH—CO—N[(1–4C)alkyl], di-[(1–4C)alkyl]N—CO—N[(1–4C)alkyl]-, carbamoyl, N—[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and wherein one of said four substituents may also be (1–4C)alkoxy;

and also independently, or in addition to, the above optional substituents, Q₂ may optionally bear on any available carbon atom up to two further substituents independently selected from (3–8C)cycloalkyl, phenyl-(1–4C)alkyl, phenyl-(1–4C)alkoxy, phenylthio, phenyl, naphthyl, benzoyl, phenoxy, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C)alkoxy substituents may optionally bear up to five substituents independently selected from halogeno, (1–4C)alkyl and (1–4C)alkoxy;

or a pharmaceutically-acceptable salt or in-vivo-hydrolysable ester thereof.

2. A pyrimidine compound of the formula (I) as claimed in claim 1, wherein
R¹ is benzyl, (3–5C)alkynyl, (3–6C)cycloalkyl-(1–6C)alkyl, (1–4C)alkyl [optionally substituted by one or two substituents independently selected from hydroxy, amino, halo, trifluoromethyl and cyano] or (3–5C)alkenyl substituted by one to three halo groups or one phenyl substituent;

$Q_1$ and $Q_2$ are independently selected from phenyl, naphthyl, indanyl and 1,2,3,4-tetrahydronaphthyl;

and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];

X is O, S, NH or NRx [wherein Rx is (1–4C)alkyl, optionally substituted by one substituent selected from halo, amino, cyano, (1–4C)alkoxy or hydroxy];

Y is as defined for Z;

Z is OH, SH, $NH_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;

n is 1, 2 or 3; m is 1, 2 or 3;

and $Q_1$ may optionally bear on any available carbon atom up to four substituents independently selected from halogen, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido ($H_2N$—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]—, carbamoyl, N—[(1–4C)alkyl]carbamoyl, N,N-di-[(1–4C)alkyl]carbamoyl, amino, (1–4C)alkylamino, di-[(1–4C)alkyl]amino, (2–4C)alkanoylamino;

and also independently, or in addition to, the above substituents, $Q_1$ may optionally bear on any available carbon atom up to two further substituents independently selected from (3–8C)cycloalkyl, phenyl-(1–4C)alkyl, phenylthio, phenyl, naphthyl, benzoyl, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl and phenylthio substituents may optionally bear up to five substituents independently selected from halogeno, (1–4C)alkyl and (1–4C)alkoxy;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino-(1–3C)alkyl, (1–4C)alkylamino-(1–3C)alkyl, di-[(1–4C)alkyl]amino-(1–3C)alkyl, cyano-(1–4C)alkyl, (2–4C)alkanoyloxy-(1–4C)-alkyl, (1–4C)alkoxy-(1–3C)alkyl, carboxy-(1–4C)alky, (1–4C)alkoxycarbonyl-(1–4C)alkyl, carbamoyl-(1–4C)alkyl, N-(1–4C)alkylcarbamoyl-(1–4C)alkyl, N,N-di-[(1–4C)alkyl]-carbamoyl-(1–4C)alkyl, pyrrolidin-1-yl-(1–3C)alkyl, piperidin-1-yl-(1–3C)alkyl, piperazin-1-yl-(1–3C)alkyl, morpholino-(1–3C)alkyl, thiomorpholino-(1–3C)alkyl, piperazin-1-yl, morpholino, thiomorpholino, cyano-(1–4C)alkoxy, carbamoyl-(1–4C)alkoxy, N-(1–4C)alkylcarbamoyl-(1–4C)alkoxy, N,N-di-[(1–4C)alkyl]-carbamoyl-(1–4C)alkoxy, 2-aminoethoxy, 2-(1–4C)alkylaminoethoxy, 2-di-[(1–4C)alkyl]aminoethoxy, (1–4C)alkoxycarbonyl-(1–4C)alkoxy, halogeno-(1–4C)alkoxy, 2-hydroxyethoxy, (2–4C)alkanoyloxy-(2–4C)alkoxy, 2-(1–4C)alkoxyethoxy, carboxy-(1–4C)alkoxy, (3–5C)alkenyloxy, (3–5C)alkynyloxy, (1–4C)alkylthio, (1–4C)alkylsulphinyl, (1–4C)alkylsulphonyl, hydroxy-(2–4C)alkylthio, hydroxy-(2–4C)alkylsulphinyl, hydroxy-(2–4C)alkylsulphonyl, ureido ($H_2N$—CO—NH—), (1–4C)alkylNH—CO—NH—, di-[(1–4C)alkyl]N—CO—NH—, (1–4C)alkylNH—CO—N[(1–4C)alkyl]-, di-[(1–4C)alkyl]N—CO—N[(1–4C)alkyl]-, carbamoyl, N—[(1–4C)alkyl]carbamoyl, N,N-di-[(1–4C)alkyl]carbamoyl, amino, (1–4C)alkylamino, di-[(1–4C)alkyl]amino, (2–4C)alkanoylamino, and wherein one of said four substituents may also be (1–4C)alkoxy; and also independently, or in addition to, the above optional substituents, $Q_2$ may optionally bear on any available carbon atom up to two further substituents independently selected from (3–8C)cycloalkyl, phenyl-(1–4C)alkyl, phenyl-(1–4C)alkoxy, phenylthio, phenyl, naphthyl, benzoyl, phenoxy, benzimidazol-2-yl and a 5- or 6-membered aromatic heterocycle (linked via a ring carbon atom and having one to three heteroatoms independently selected from oxygen, sulphur and nitrogen); wherein said naphthyl, phenyl, benzoyl, 5- or 6-membered aromatic heterocyclic substituents and the phenyl group in said phenyl-(1–4C)alkyl, phenylthio, phenoxy and phenyl-(1–4C)alkoxy substituents may optionally bear up to five substituents independently selected from halogeno, (1–4C)alkyl and (1–4C)alkoxy;

or a pharmaceutically-acceptable salt or in-vivo-hydrolysable ester thereof.

3. A pyrimidine compound of the formula (I) as claimed in claim 1, wherein $R^1$ is benzyl, (3–5C)alkynyl, (3–6C)cycloalkyl-(1–6C)alkyl, (1–4C)alkyl [optionally substituted by one or two substituents independently selected from hydroxy, amino, halo, trifluoromethyl and cyano] or (3–5C)alkenyl substituted by one to three halo groups or one phenyl substituent;

$Q_1$ and $Q_2$ are independently selected from phenyl or indanyl;

and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];

X is O, S, NH or NRx [wherein Rx is (1–4C)alkyl, optionally substituted by one substituent selected from halo, amino, cyano, (1–4C)alkoxy or hydroxy];

Y is as defined for Z;

Z is OH, SH, $NH_2$, (1–4C)alkoxy, (1–4C)alkylthio, —NH(1–4C)alkyl, —N[(1–4C)alkyl]$_2$, —NH-(3–8C)cycloalkyl, pyrrolidin-1-yl, piperidin-1-yl, piperazin-1-yl [optionally substituted in the 4-position by (1–4C)alkyl or (1–4C)alkanoyl], morpholino or thiomorpholino;

n is 1, 2 or 3; m is 1, 2 or 3;

and $Q_1$ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

4. A pyrimidine compound of the formula (I) as claimed in claim 1, wherein $R^1$ is benzyl, (3–5C)alkynyl, (3–6C)cycloalkyl-(1–6C)alkyl, (1–4C)alkyl [optionally substituted by one or two substituents independently selected from hydroxy, amino, halo, trifluoromethyl and cyano] or (3–5C)alkenyl substituted by one to three halo groups or one phenyl substituent;

$Q_1$ and $Q_2$ are independently selected from phenyl or indan-5-yl;

and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];

X is O;

Y is OH and

Z is —NH(1–4C)alkyl, —N[(1–4C)alkyl]$_2$, —NR-(3–8C)cycloalkyl, pyrrolidin-1-yl or piperazin-1-yl [optionally substituted in the 4-position by (1–4C)alkyl or (1–4C)alkanoyl];

n is 1 or 2 and m is 1 or 2;

and $Q_1$ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

5. A pyrimidine compound of the formula (I) as claimed in claim 1, wherein $R^1$ is —$CH_2CH=CHBr$, —$CH_2CH_2CH_2CF_3$ or —$CH_2CH=CH$-phenyl;

$Q_1$ and $Q_2$ are independently selected from phenyl or indan-5-yl;

and one or both of $Q_1$ and $Q_2$ bears on any available carbon atom one substituent of the formula (Ia) and $Q_2$ may optionally bear on any available carbon atom further substituents of the formula (Ia) [provided that when present in $Q_1$ the substituent of formula (Ia) is not adjacent to the —NH— link];

X is O;

Y is OH and

Z is —NH(1–4C)alkyl, —N[(1–4C)alkyl]$_2$, —NH-(3–8C)cycloalkyl, pyrrolidin-1-yl or piperazin-1-yl [optionally substituted in the 4-position by (1–4C)alkyl or (1–4C)alkanoyl];

n is 1 or 2 and m is 1 or 2;

and $Q_1$ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and $Q_2$ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, $Q_2$ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

6. A pyrimidine compound of the formula (I) as claimed in claim 1, wherein R¹ is —CH₂CH=CHBr, —CH₂CH₂CH₂CF₃ or —CH₂CH=CH-phenyl;

Q₁ and Q₂ are both phenyl;

Q₁ bears on any available carbon atom one substituent of the formula (Ia) [provided that the substituent of formula (Ia) is not adjacent to the —NH— link];

X is O;

Y is OH and

Z is —NH(1–4C)alkyl, —N[(1–4C)alkyl]₂, —NR-(3–8C)cycloalkyl, pyrrolidin-1-yl or piperazin-1-yl [optionally substituted in the 4-position by (1–4C)alkyl or (1–4C)alkanoyl];

n is 1 or 2 and m is 1 or 2;

and Q₁ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and Q₂ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, Q₂ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

7. A pyrimidine compound of the formula (I) as claimed in claim 1, wherein Q₁ and Q₂ are independently selected from phenyl or indan-5-yl;

and one or both of Q₁ and Q₂ bears on any available carbon atom one substituent of the formula (Ia) and Q₂ may optionally bear on any available carbon atom further substituents of the formula (Ia) [provided that when present in Q₁ the substituent of formula (Ia) is not adjacent to the —NH— link];

X is O;

Y is OH and

Z is —NH(1–4C)alkyl, —N[(1–4C)alkyl]₂, —NH-(3–8C)cycloalkyl, pyrrolidin-1-yl or piperazin-1-yl [optionally substituted in the 4-position by (1–4C)alkyl or (1–4C)alkanoyl];

n is 1 or 2 and m is 1 or 2;

and Q₁ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and Q₂ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)atkyl]amino, (2–4C)alkanoylamino, and also independently, or in addition to, the above optional substituents, Q₂ may optionally bear on any available carbon atom up to two further substituents independently selected from phenylthio, phenyl, phenoxy and benzimidazol-2-yl; or a pharmaceutically-acceptable salt or in-vivo-hydrolysable ester thereof.

8. A pyrimidine compound of the formula (I) as claimed in claim 1, wherein Q₁ and Q₂ are both phenyl;

Q₁ bears on any available carbon atom one substituent of the formula (Ia) [provided that the substituent of formula (Ia) is not adjacent to the —NH— link];

X is O;

Y is OH and

Z is —NH(1–4C)alkyl, —N[(1–4C)alkyl]₂, —NH-(3–8C)cycloalkyl, pyrrolidin-1-yl or piperazin-1-yl [optionally substituted in the 4-position by (1–4C)alkyl or (1–4C)alkanoyl];

n is 1 or 2 and m is 1 or 2;

and Q₁ may optionally bear on any available carbon atom up to four substituents independently selected from halogeno, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino;

and Q₂ may optionally bear on any available carbon atom up to four substituents independently selected from halogeno, hydroxy, thio, nitro, carboxy, cyano, (2–4C)alkenyl [optionally substituted by up to three halo substituents, or by one trifluoromethyl substituent], (2–4C)alkynyl, (1–5C)alkanoyl, (1–4C)alkoxycarbonyl, (1–6C)alkyl, hydroxy-(1–6C)alkyl, fluoro-(1–4C)alkyl, amino, (1–4C)alkylamino, di-[(1–4C)alkyl]amino, (2–4C)alkanoylamino, and also independently, or in addition to, the above optional substituents, Q₂ may optionally bear on any available carbon atom up to two further substituents independently selected from phenylthio, phenyl, phenoxy and benzimidazol-2-yl;

or a pharmaceutically-acceptable salt or in-vivo-hydrolysable ester thereof.

9. A pyrimidine compound of the formula (I) as claimed in claim 1,

2-{4-[3-(N,N-Dimethyl)amino-2-hydroxy-propoxy]anilino}-4-(2,4-difluoro-(N-cyanomethyl)anilino)pyrimidine;

2-{4-[3 -(N,N-Dimethyl)amino-2-hydroxy-propoxy]anilino}-4-(2,5-dichloro-(N-2-fluoroethyl)anilino)pyrimidine;

2-{4-[3-(N,N-Dimethyl)amino-2-hydroxy-propoxy]
    anilino}-4-(2,5-dichloro-(N-propyn-2-yl)anilino)pyrimidine;
2-{4-[3-(N,N-Dimethyl)amino-2-hydroxy-propoxy]
    anilino}-4-(2,5-dichloro-(N-cyanomethyl)anilino)pyrimidine;
2-{4-[3-(N,N-Dimethyl)amino-2-hydroxy-propoxy]
    anilino}-4-(2,5-dichloro-(N-2,2-difluoroethyl)anilino)pyrimidine;
2-{4-[3-(N,N-Dimethyl)amino-2-hydroxy-propoxy]
    anilino}-4-(2,5-dichloro-(N-4,4,4-trifluorobutyl)anhlino)pyrimidine;
2-{4-[3-(N,N-Dimethyl)amino-2-hydroxy-propoxy]
    anilino}-4-(2,5-dichloro-(N-3-phenylprop-2-enyl)anilino)pyrimidine;
2-{4-[3-(N,N-Dimethyl)amino-2-hydroxy-propoxy]
    anilino}-4-(2-fluoro-5-methyl-(N-4,4,4-trifluorobutyl)anilino)pyrimidine;
2-{4-[3-(N,N-Dimethyl)amino-2-hydroxy-propoxy]
    anilino}-4-(2-fluoro-5-methyl-(N-3-bromoprop-2-enyl)anilino)pyrimidine;
2-{4-[3-(N,N-Dimethyl)amino-2-hydroxy-propoxy]
    anilino}-4-(2-fluoro-5 -methyl-(N-3-phenylprop-2-enyl)anilino)pyrimidine;

or pharmaceutically-acceptable salt or in-vivo hydrolysable ester thereof.

10. A process for the preparation of a compound of the formula (I) as claimed in claim 1, which comprises of a) to h):

a) reacting a pyrimidine of formula (II):

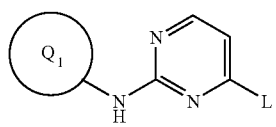

(II)

wherein L is a displaceable group, with a compound of formula (III):

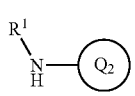

(III)

b) reaction of a pyrimidine of formula (IV):

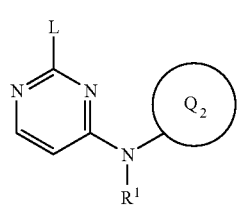

(IV)

wherein L is a displaceable group, with a compound of formula (V):

(V)

c) for compounds of formula (I) wherein n is 1, 2 or 3; m=1 and Y is OH, $NH_2$ or SH:
    reaction of a 3-membered heteroalkyl ring of formula (VI):

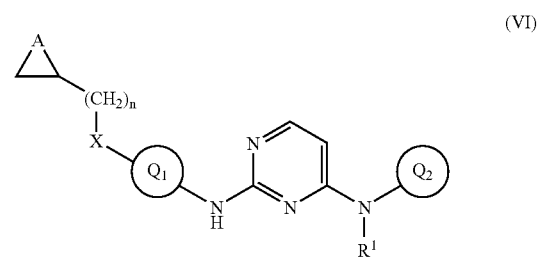

(VI)

wherein A is O, S or NH;
with a nucleophile of formula (VII):

 Z—D  (VII)

wherein D is H or a suitable counter-ion;

d) for compounds of formula (I) where X is oxygen:
    reaction of an alcohol of formula (VIII):

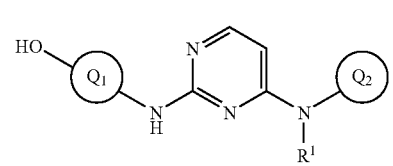

(VIII)

with an alcohol of formula (IX):

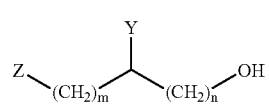

(IX)

e) for compounds of formula (I) wherein X is O, NH or S; Y is OH and m is 2 or 3:
    reaction of a compound of formula (X):

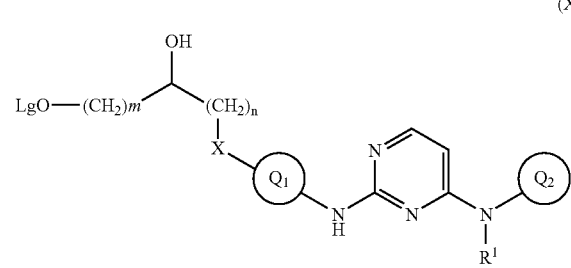

(X)

wherein —OLg is a leaving group; with a nucleophile of formula Z—D (VII) wherein D is H or a suitable counter-ion;

or f) for compounds of formula (I) in which Z is SH, by conversion of a thioacetate group in a corresponding compound;

and thereafter if necessary:

i) converting a compound of the formula (I) into another compound of the formula (I);

ii) removing any protecting groups;

iii) forming a pharmaceutically acceptable salt or in vivo hydrolysable ester; wherein L is a displaceable group and D is hydrogen or a counter-ion.

11. A pharmaceutical composition which comprises a compound of the formula (I) as claimed in any one of claims 1 to 9, or a pharmaceutically-acceptable salt or an in-vivo hydrolysable ester thereof, and a pharmaceutically acceptable diluent or carrier.

* * * * *